United States Patent
Bandiera et al.

(10) Patent No.: US 6,974,828 B2
(45) Date of Patent: Dec. 13, 2005

(54) PROPANOIC ACID DERIVATIVES AS INTERGRIN RECEPTOR ANTAGONISTS

(75) Inventors: Tiziano Bandiera, Gambolo (IT); Paola Vianello, Milan (IT); Paolo Cozzi, Milan (IT); Arturo Galvani, Parabiago (IT)

(73) Assignee: Pharmacia Italia S.p.A., Milan (IT)

( * ) Notice: Subject to any disclaimer, the term of this patent is extended or adjusted under 35 U.S.C. 154(b) by 147 days.

(21) Appl. No.: 10/258,584

(22) PCT Filed: Apr. 19, 2001

(86) PCT No.: PCT/EP01/04472

§ 371 (c)(1),
(2), (4) Date: Nov. 1, 2002

(87) PCT Pub. No.: WO01/87840

PCT Pub. Date: Nov. 22, 2001

(65) Prior Publication Data

US 2003/0144311 A1 Jul. 31, 2003

(30) Foreign Application Priority Data

May 16, 2000 (GB) .............................................. 0011817

(51) Int. Cl.$^7$ ...................... C07D 213/55; A61K 31/444
(52) U.S. Cl. ........................ 514/357; 514/562; 514/563; 514/564; 546/332; 562/426; 562/430; 564/439
(58) Field of Search .......................... 546/332; 562/426, 562/430; 564/439; 514/357, 562, 563, 564

(56) References Cited

FOREIGN PATENT DOCUMENTS

| WO | 97 36859 | | 10/1997 |
|----|----------|---|---------|
| WO | 97 36862 | | 10/1997 |
| WO | WO 98/04247 | * | 2/1998 |

OTHER PUBLICATIONS

Agrez et al., The alpha–v–beta–6 Integrin induces gelatinase B secretion in colon cancer cells, Int. J. Cancer, 81, pp. 90–97, 1999.*

Brooks et al., Integrin alpha–v–beta–3: A therapeutic target, DN&P, 10(8), pp. 456–461, Oct. 1997.*

Gladson et al., Vitronectin Expression in Differentiating Neuroblastic Tumors, American Journal of Pathology, vol. 150, No. 5, pp. 1631–1646, May 1997.*

Kim et al., Vitronectin–driven Human Keratinocyte Locomotion Is Mediated by the alpha–v–beta–5 Integrin Receptor, The Journal of Biological Chemistry, vol. 269, No. 43, pp. 26928–26932, Oct. 1994.*

Nip et al., The role of the Integrin vitronectin receptor, alpha–v–beta–3 in melanoma metastasis, Cancer and Metastasis Reviews, 14, pp. 241–252, 1995.*

Raynal et al., Bone Sialoprotein Stimulates in vitro Bone Resorption, Endocrinology, vol. 137, No. 6, pp. 2347–2354, 1996.*

Schvartz et al., Vitronectin, The International Journal of Biochemistry & Cell Biology, 31, pp. 539–544, 1999.*

Simone, Oncology: Introduction, Cecil Textbook of Medicine, 20$^{th}$ Edition, vol. 1, pp. 1004–1010, 1996.*

* cited by examiner

*Primary Examiner*—Deepak Rao
(74) *Attorney, Agent, or Firm*—Peter C. Richardson; Garth Butterfield; Adrian G. Looney

(57) ABSTRACT

Novel propanoic acid derivatives are integrin receptor antagonists or inhibitors, in particular of the avb3 integrin receptor. The compounds of the invention are for instance useful for the treatment of solid tumors by inhibition of angiogenic growth of tumor vessel network, thus promoting tumor regression, inhibition of metastatic spread, thus avoiding cancer metastases, inhibition of bone resorption, thus controlling osteoporosis, inhibition of smooth muscle cells migration into neointima, thus blocking restenosis after percutaneous coronary angioplasty and the treatment of other pathological conditions mediated by cell adhesion, cell migration or angiogenesis such e.g. diabetic retinopaty, rheumatoid arthritis and inflammation.

7 Claims, No Drawings

PROPANOIC ACID DERIVATIVES AS INTERGRIN RECEPTOR ANTAGONISTS

This application is a 371 of PCT/EP01/04472 filed Apr. 19, 2001.

The present invention relates to novel non-peptide compounds which bind to the integrin receptor αvβ3, to pharmaceutical compositions containing such compounds, processes for preparing such compounds, and to methods of using these compounds, alone or in combination with other therapeutic agents. Integrins are membrane-bound receptors that mediate cell-matrix and cell-cell adhesion interactions. The compounds of present invention are useful for the treatment of diseases in which the pathology arises from ligation of an integrin receptor, especially the vitronectin receptor, and therefore of diseases mediated by cell adhesion and angiogenesis. The compounds of present invention are useful in selectively inhibiting or antagonizing αvβ3 integrin and therefore are useful for the treatment of solid tumors by inhibition of angiogenic growth of tumor vessel network, thus promoting tumor regression, inhibition of metastatic spread, thus avoiding cancer metastases, inhibition of bone resorption, thus controlling osteoporosis, inhibition of smooth muscle cells migration into neointima, thus blocking restenosis after percutaneous coronary angioplasty and the treatment of other pathological conditions mediated by cell adhesion, cell migration or angiogenesis such e.g. diabetic retinopaty, rheumatoid arthritis and inflammation.

The utility of antagonists of the αvβ3 integrin and related cell surface adhesive protein receptors is well known in the art.

The present invention as a first object provides novel non-peptide compounds having the following formula (I)

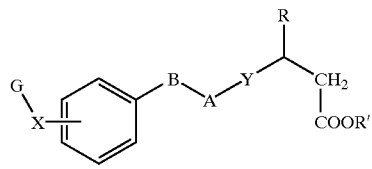

wherein:

G is a group selected among:

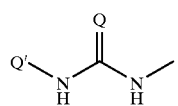

wherein Q is NH or O and Q' is H, C1–C6 alkyl, phenyl, or phenyl-C1–C4-alkyl;

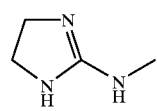

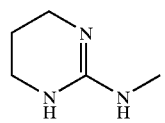

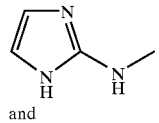

and

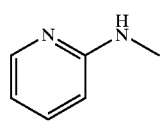

X is a direct linkage, $CH_2$—CONH, —$(CH_2)_m$— or $(CH_2)_m$—X' wherein X' is O, S or NH and m is an integer of 1 to 4;

B is CONH, $CH_2$—CONH, a $C_2$–$C_4$ alkylene or $C_2$–$C_4$ alkenylene chain or —$(CH_2)_m$—X', wherein X' and m are as defined above;

A is a phenyl or pyridine ring, unsubstituted or optionally substituted by one to three substituents chosen independently from halogen, $CF_3$, $C_1$–$C_4$ alkyl, OH and $C_1$–$C_4$ alkoxy;

Y is selected from O or $S(O)_n$ wherein n is zero, 1 or 2;

R is $C_1$–$C_6$ alkyl or a phenyl or $C_5$–$C_7$ monocyclic heteroaryl ring containing one to three heteroatoms chosen from O, S, and N, unsubstituted or optionally substituted by one to three substituents chosen independently from halogen, $CF_3$, $C_1$–$C_4$ alkyl, hydroxy and $C_1$–$C_4$ alkoxy;

R' is hydrogen, $C_1$–$C_6$ alkyl, $C_2$–$C_4$ alkenyl, $C_2$–$C_4$ alkynyl, aryl or aryl-$C_1$–$C_4$ alkyl;

and the pharmaceutically acceptable salts thereof.

The present invention includes within its scope all possible isomers, stereoisomers and optical isomers and their mixtures, and the metabolites and the metabolic precursors or bioprecursors of the compounds of formula (I).

A halogen atom is preferably chlorine or fluorine.

The alkyl, alkoxy, alkenyl and alkynyl groups and the alkylene and alkenylene chains may be branched or straight groups or chains, respectively.

A $C_5$–$C_7$ monocyclic heteroaryl ring is preferably a $C_5$–$C_6$ heteromonocyclic ring, in particular selected from pyridine, pyrazine, pyridazine, pyrimidine, thiophene, pyrrole, pyrazole, imidazole, oxazole and isoxazole.

An aryl group is, e.g., an aromatic $C_6$–$C_{20}$ mono- or poly-nuclear moiety, typically phenyl, unsubstituted or substituted by one to three substituents independently chosen from halogen, hydroxy, $CF_3$, $C_1$–$C_4$ alkyl and $C_1$–$C_4$ alkoxy.

Accordingly an aralkyl group is e.g. benzyl or phenethyl, in which the phenyl ring is optionally substituted by one to three substituents independently chosen from halogen, hydroxy, $CF_3$, $C_1$–$C_4$ alkyl and $C_1$–$C_4$ alkoxy.

A $C_2$–$C_4$ alkenyl group is preferably an allyl group.

A $C_1$–$C_6$ alkyl group is preferably a $C_1$–$C_4$ alkyl group.

A $C_1$–$C_4$ alkyl group is preferably a methyl or ethyl group.

A $C_2$–$C_4$ alkynyl group is preferably an ethynyl group.

A $C_1$–$C_4$ alkoxy group is preferably methoxy, ethoxy, propoxy and butoxy.

Examples of pharmaceutically acceptable salts of the compounds of the invention are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)- amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic and sulphuric acids and with organic acids, e.g. citric, tartaric, maleic, malic, fumaric, trifluoroacetic, methanesulphonic and ethanesulphonic acids.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are those wherein, in formula (I),

G is as defined above;
X is a direct linkage or $(CH_2)_m$—X', in which m is 1 or 2 and X' is as defined above;
B is CONH or CH=CH or $CH_2$—X', wherein X' is as defined above;
A is a phenyl ring unsubstituted or optionally substituted by one or two substituents selected from halogen, $CF_3$, $C_1$–$C_4$ alkyl, OH and $C_1$–$C_4$ alkoxy;
Y is as defined above;
R is a phenyl, pyridine, pyrazine, pyridazine, pyrimidine, thiophene, pyrrole, pyrazole, imidazole, oxazole or isoxazole ring, unsubstituded or optionally substituted by one or two substituents selected from halogen, $CF_3$, $C_1$–$C_4$ alkyl, OH and $C_1$–$C_4$ alkoxy;
R' is hydrogen, $C_1$–$C_6$ alkyl;
and the pharmaceutically acceptable salts thereof.

A further class of preferred compounds of the invention are those wherein, in formula (I), G and Y are as defined above;
X is CH2-CONH or $(CH_2)_m$—X', in which m and X' are as defined above;
A is a phenyl or pyridine ring, unsubstituted or optionally substituted by one to three substituents chosen independently from halogen, $CF_3$, $C_1$–$C_4$ alkyl, OH and $C_1$–$C_4$ alkoxy;
B is CONH or $CH_2$—CONH;
R is a phenyl, pyridine, pyrazine, pyridazine, pyrimidine, thiophene, pyrrole, pyrazole, imidazole, oxazole or isoxazole ring, unsubstituded or optionally substituted by one or two substituents selected from halogen, $CF_3$, $C_1$–$C_4$ alkyl, OH and $C_1$–$C_4$ alkoxy;
R' is hydrogen, $C_1$–$C_6$ alkyl;
and the pharmaceutically acceptable salts thereof.

Most preferred compounds of the invention are those wherein, in formula (I),

G and Y are as defined above;
X is a direct linkage or $(CH_2)_m$—X', in which m is 1 or 2 and X' is as defined above;
B is CONH or CH=CH or $CH_2$—X', wherein X' is as defined above;
A is a phenyl ring unsubstituted or optionally substituted by one or two substituents selected from halogen, $CF_3$, $C_1$–$C_4$ alkyl, OH and $C_1$–$C_4$ alkoxy;
R is a phenyl or pyridine ring, unsubstituded or optionally substituted by one or two substituents selected from halogen, $CF_3$, $C_1$–$C_4$ alkyl, OH and $C_1$–$C_4$ alkoxy;

R' is hydrogen, $C_1$–$C_6$ alkyl;
and the pharmaceutically acceptable salts thereof.

Examples of specific preferred compounds according to the invention are the following:

3-({2-[(3-{[amino(imino)methyl]amino}benzoyl)amino]phenyl}sulfanyl)-3-(3-pyridinyl)propanoic acid;
3-({3-[(3-{[amino(imino)methyl]amino}benzoyl)amino]phenyl}sulfanyl)-3-(3-pyridinyl)propanoic acid;
3-({4-[(3-{[amino(imino)methyl]amino}benzoyl)amino]phenyl}sulfanyl)-3-(3-pyridinyl)propanoic acid;
3-({2-[(3-{[(benzylamino)(imino)methyl]amino}benzoyl)amino]phenyl}sulfanyl)-3-(3-pyridinyl)propanoic acid;
3-({3-[(3-{[(benzylamino)(imino)methyl]amino}benzoyl)amino]phenyl}sulfanyl)-3-(3-pyridinyl)propanoic acid;
3-({4-[(3-{[(benzylamino)(imino)methyl]amino}benzoyl)amino]phenyl}sulfanyl)-3-(3-pyridinyl)propanoic acid;
3-{[2-({3-[(aminocarbonyl)amino]benzoyl}amino)phenyl]sulfanyl}-3-(3-pyridinyl)propanoic acid;
3-{[3-({3-[(aminocarbonyl)amino]benzoyl}amino)phenyl]sulfanyl}-3-(3-pyridinyl)propanoic acid;
3-{[4-({3-[(aminocarbonyl)amino]benzoyl}amino)phenyl]sulfanyl}-3-(3-pyridinyl)propanoic acid;
3-({2-[(3-{[(benzylamino)carbonyl]amino}benzoyl)amino]phenyl}sulfanyl)-3-(3-pyridinyl)propanoic acid;
3-({3-[(3-{[(benzylamino)carbonyl]amino}benzoyl)amino]phenyl}sulfanyl)-3-(3-pyridinyl)propanoic acid;
3-({4-[(3-{[(benzylamino)carbonyl]amino}benzoyl)amino]phenyl}sulfanyl)-3-(3-pyridinyl)propanoic acid;
3-[(2-{[3-(4,5-dihydro-1H-imidazol-2-ylamino)benzoyl]amino}phenyl)sulfanyl]-3-(3-pyridinyl)propanoic acid;
3-[(3-{[3-(4,5-dihydro-1H-imidazol-2-ylamino)benzoyl]amino}phenyl)sulfanyl]-3-(3-pyridinyl)propanoic acid;
3-[(4-{[3-(4,5-dihydro-1H-imidazol-2-ylamino)benzoyl]amino}phenyl)sulfanyl]-3-(3-pyridinyl)propanoic acid;
3-[(2-{[3-(1H-imidazol-2-ylamino)benzoyl]amino}phenyl)sulfanyl]-3-(3-pyridinyl)propanoic acid;
3-[(3-{[3-(1H-imidazol-2-ylamino)benzoyl]amino}phenyl)sulfanyl]-3-(3-pyridinyl)propanoic acid;
3-[(4-{[3-(1H-imidazol-2-ylamino)benzoyl]amino}phenyl)sulfanyl]-3-(3-pyridinyl)propanoic acid;
3-(3-pyridinyl)-3-[(2-{[3-(2-pyridinylamino)benzoyl]amino}phenyl)sulfanyl]propanoic acid;
3-(3-pyridinyl)-3-[(3-{[3-(2-pyridinylamino)benzoyl]amino}phenyl)sulfanyl]propanoic acid;
3-(3-pyridinyl)-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-(3-pyridinyl)propanoic acid;
3-({3-[(4-{[amino(imino)methyl]amino}benzoyl)amino]phonyl}sulfanyl)-3-(3-pyridinyl)propanoic acid;
3-({4-[(4-{[amino(imino)methyl]amino}benzoyl)amino]phenyl}sulfanyl)-3-(3-pyridinyl)propanoic acid;
3-({2-[(4-{[(benzylamino)(imino)methyl]amino}benzoyl)amino]phenyl}sulfanyl)-3-(3-pyridinyl)propanoic acid;
3-({3-[(4-{[(benzylamino)(imino)methyl]amino}benzoyl)amino]phenyl}sulfanyl)-3-(3-pyridinyl)propanoic acid;
3-({4-[(4-{[(benzylamino)(imino)methyl]amino}benzoyl)amino]phenyl}sulfanyl)-3-(3-pyridinyl)propanoic acid;
3-{[2-({4-[(aminocarbonyl)amino]benzoyl}amino)phenyl]sulfanyl}-3-(3-pyridinyl)propanoic acid;
3-{[3-({4-[(aminocarbonyl)amino]benzoyl}amino)phenyl]sulfanyl}-3-(3-pyridinyl)propanoic acid;
3-{[4-({4-[(aminocarbonyl)amino]benzoyl}amino)phenyl]sulfanyl}-3-(3-pyridinyl)propanoic acid;
3-({2-[(4-{[(benzylamino)carbonyl]amino}benzoyl)amino]phenyl}sulfanyl)-3-(3-pyridinyl)propanoic acid;
3-({3-[(4-{[(benzylamino)carbonyl]amino}benzoyl)amino]phenyl}sulfanyl)-3-(3-pyridinyl)propanoic acid;

3-({4-[(4-{[(benzylamino)carbonyl]amino}benzoyl)amino]phenyl}sulfanyl)-3-(3-pyridinyl)propanoic acid;
3-[(2-{[4-(4,5-dihydro-1H-imidazol-2-ylamino)benzoyl]amino}phenyl)sulfanyl]-3-(3-pyridinyl)propanoic acid;
3-[(3-{[4-(4,5-dihydro-1H-imidazol-2-ylamino)benzoyl]amino}phenyl)sulfanyl]-3-(3-pyridinyl)propanoic acid;
3-[(4-{[4-(4,5-dihydro-1H-imidazol-2-ylamino)benzoyl]amino}phenyl)sulfanyl]-3-(3-pyridinyl)propanoic acid;
3-[(2-{[4-(1H-imidazol-2-ylamino)benzoyl]amino}phenyl)sulfanyl]-3-(3-pyridinyl)propanoic acid;
3-[(3-{[4-(1H-imidazol-2-ylamino)benzoyl]amino}phenyl)sulfanyl]-3-(3-pyridinyl)propanoic acid;
3-[(4-{[4-(1H-imidazol-2-ylamino)benzoyl]amino}phenyl)sulfanyl]-3-(3-pyridinyl)propanoic acid;
3-(3-pyridinyl)-3-[(2-{[4-(2-pyridinylamino)benzoyl]amino}phenyl)sulfanyl]propanoic acid;
3-(3-pyridinyl)-3-[(3-{[4-(2-pyridinylamino)benzoyl]amino}phenyl)sulfanyl]propanoic acid;
3-(3-pyridinyl)-3-[(4-{[4-(2-pyridinylamino)benzoyl]amino}phenyl)sulfanyl]propanoic acid;
3-({3-[(3-{[amino(imino)methyl]amino}benzoyl)amino]phenyl}sulfanyl)-3-phenylpropanoic acid;
3-({2-[(3-{[amino(imino)methyl]amino}benzoyl)amino]phenyl}sulfanyl)-3-phenylpropanoic acid;
3-({4-[(3-{[amino(imino)methyl]amino}benzoyl)amino]phenyl}sulfanyl)-3-phenylpropanoic acid;
3-({2-[(3-{[(benzylamino)(imino)methyl]amino}benzoyl)amino]phenyl}sulfanyl)-3-phenylpropanoic acid;
3-({3-[(3-{[(benzylamino)(imino)methyl]amino}benzoyl)amino]phenyl}sulfanyl)-3-phenylpropanoic acid;
3-({4-[(3-{[(benzylamino)(imino)methyl]amino}benzoyl)amino]phenyl}sulfanyl)-3-phenylpropanoic acid;
3-{[2-({3-[(aminocarbonyl)amino]benzoyl}amino)phenyl]sulfanyl}-3-phenylpropanoic acid;
3-{[3-({3-[(aminocarbonyl)amino]benzoyl}amino)phenyl]sulfanyl}-3-phenylpropanoic acid;
3-{[4-({3-[(aminocarbonyl)amino]benzoyl}amino)phenyl]sulfanyl}-3-phenylpropanoicacid;
3-({2-[(3-{[(benzylamino)carbonyl]amino}benzoyl)amino]phenyl}sulfanyl)-3-phenylpropanoic acid;
3-({3-[(3-{[(benzylamino)carbonyl]amino}benzoyl)amino]phenyl}sulfanyl)-3-phenylpropanoic acid;
3-({4-[(3-{[(benzylamino)carbonyl]amino}benzoyl)amino]phenyl}sulfanyl)-3-phenylpropanoic acid;
3-[(2-{[3-(4,5-dihydro-1H-imidazol-2-ylamino)benzoyl]amino}phenyl)sulfanyl]-3-phenylpropanoic acid;
3-[(3-{[3-(4,5-dihydro-1H-imidazol-2-ylamino)benzoyl]amino}phenyl)sulfanyl]-3-phenylpropanoic acid;
3-[(4-{[3-(4,5-dihydro-1H-imidazol-2-ylamino)benzoyl]amino}phenyl)sulfanyl]-3-phenylpropanoicacid;
3-[(2-{[3-(1H-imidazol-2-ylamino)benzoyl]amino}phenyl)sulfanyl]-3-phenylpropanoic acid;
3-[(3-{[3-(1H-imidazol-2-ylamino)benzoyl]amino}phenyl)sulfanyl]-3-phenylpropanoic acid;
3-[(4-{[3-(1H-imidazol-2-ylamino)benzoyl]amino}phenyl)sulfanyl]-3-phenylpropanoic acid;
3-phenyl-3-[(2-{[3-(2-pyridinylamino)benzoyl]amino}phenyl)sulfanyl]propanoic acid;
3-phenyl-3-[(3-{[3-(2-pyridinylamino)benzoyl]amino}phenyl)sulfanyl]propanoic acid;
3-phenyl-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-phenylpropanoic acid;
3-({3-[(4-{[amino(imino)methyl]amino}benzoyl)amino]phenyl}sulfanyl)-3-phenylpropanoic acid;
3-({4-[(4-{[amino(imino)methyl]amino}benzoyl)amino]phenyl}sulfanyl)-3-phenylpropanoic acid;
3-({2-[(4-{[(benzylamino)(imino)methyl]amino}benzoyl)amino]phenyl}sulfanyl)-3-phenylpropanoic acid;
3-({3-[(4-{[(benzylamino)(imino)methyl]amino}benzoyl)amino]phenyl}sulfanyl)-3-phenylpropanoic acid;
3-({4-[(4-{[(benzylamino)(imino)methyl]amino}benzoyl)amino]phenyl}sulfanyl)-3-phenylpropanoic acid;
3-{[2-({4-[(aminocarbonyl)amino]benzoyl}amino)phenyl]sulfanyl}-3-phenylpropanoic acid;
3-{[3-({4-[(aminocarbonyl)amino]benzoyl}amino)phenyl]sulfanyl}-3-phenylpropanoic acid;
3-{[4-({4-[(aminocarbonyl)amino]benzoyl}amino)phenyl]sulfanyl}-3-phenylpropanoicacid;
3-({2-[(4-{[(benzylamino)carbonyl]amino}benzoyl)amino]phenyl}sulfanyl)-3-phenylpropanoic acid;
3-({3-[(4-{[(benzylamino)carbonyl]amino}benzoyl)amino]phenyl}sulfanyl)-3-phenylpropanoic acid;
3-({4-[(4-{[(benzylamino)carbonyl]amino}benzoyl)amino]phenyl}sulfanyl)-3-phenylpropanoic acid;
3-[(2-{[4-(4,5-dihydro-1H-imidazol-2-ylamino)benzoyl]amino}phenyl)sulfanyl]-3-phenylpropanoic acid;
3-[(3-{[4-(4,5-dihydro-1H-imidazol-2-ylamino)benzoyl]amino}phenyl)sulfanyl]-3-phenylpropanoic acid;
3-[(4-{[4-(4,5-dihydro-1H-imidazol-2-ylamino)benzoyl]amino}phenyl)sulfanyl]-3-phenylpropanoic acid;
3-[(2-{[4-(1H-imidazol-2-ylamino)benzoyl]amino}phenyl)sulfanyl]-3-phenylpropanoic acid;
3-[(3-{[4-(1H-imidazol-2-ylamino)benzoyl]amino}phenyl)sulfanyl]-3-phenylpropanoic acid;
3-[(4-{[4-(1H-imidazol-2-ylamino)benzoyl]amino}phenyl)sulfanyl]-3-phenylpropanoic acid;
3-phenyl-3-[(2-{[4-(2-pyridinylamino)benzoyl]amino}phenyl)sulfanyl]propanoic acid;
3-phenyl-3-[(3-{[4-(2-pyridinylamino)benzoyl]amino}phenyl)sulfanyl]propanoic acid;
3-phenyl-3-[(4-{[4-(2-pyridinylamino)benzoyl]amino}phenyl)sulfanyl]propanoic acid;
3-{2-[(4-{[amino(imino)methyl]amino}benzoyl)amino]phenoxy}-3-(3-pyridinyl)propanoic acid;
3-{3-[(4-{[amino(imino)methyl]amino}benzoyl)amino]phenoxy}-3-(3-pyridinyl)propanoic acid;
3-{4-[(4-{[amino(imino)methyl]amino}benzoyl)amino]phenoxy}-3-(3-pyridinyl)propanoic acid;
3-{2-[(4-{[(benzylamino)(imino)methyl]amino}benzoyl)amino]phenoxy}-3-(3-pyridinyl)propanoic acid;
3-{3-[(4-{[(benzylamino)(imino)methyl]amino}benzoyl)amino]phenoxy}-3-(3-pyridinyl)propanoic acid;
3-{4-[(4-{[(benzylamino)(imino)methyl]amino}benzoyl)amino]phenoxy}-3-(3-pyridinyl)propanoic acid;
3-[2-({4-[(aminocarbonyl)amino]benzoyl}amino)phenoxy]-3-(3-pyridinyl)propanoic acid;
3-[3-({4-[(aminocarbonyl)amino]benzoyl}amino)phenoxy]-3-(3-pyridinyl)propanoic acid;
3-[4-({4-[(aminocarbonyl)amino]benzoyl}amino)phenoxy]-3-(3-pyridinyl)propanoic acid;
3-{2-[(4-{[(benzylamino)carbonyl]amino}benzoyl)amino]phenoxy}-3-(3-pyridinyl)propanoic acid;
3-{3-[(4-{[(benzylamino)carbonyl]amino}benzoyl)amino]phenoxy}-3-(3-pyridinyl)propanoic acid;
3-{4-[(4-{[(benzylamino)carbonyl]amino}benzoyl)amino]phenoxy}-3-(3-pyridinyl)propanoic acid;
3-(2-{[4-(4,5-dihydro-1H-imidazol-2-ylamino)benzoyl]amino}phenoxy)-3-(3-pyridinyl)propanoic acid;
3-(3-{[4-(4,5-dihydro-1H-imidazol-2-ylamino)benzoyl]amino}phenoxy)-3-(3-pyridinyl)propanoic acid;
3-(4-{[4-(4,5-dihydro-1H-imidazol-2-ylamino)benzoyl]amino}phenoxy)-3-(3-pyridinyl)propanoic acid;
3-(2-{[4-(1H-imidazol-2-ylamino)benzoyl]amino}phenoxy)-3-(3-pyridinyl)propanoic acid;

3-(3-{[4-(1H-imidazol-2-ylamino)benzoyl]
   amino}phenoxy)-3-(3-pyridinyl)propanoic acid;
3-(4-{[4-(1H-imidazol-2-ylamino)benzoyl]
   amino}phenoxy)-3-(3-pyridinyl)propanoic acid;
3-(3-pyridinyl)-3-(2-{[4-(2-pyridinylamino)benzoyl]
   amino}phenoxy)propanoic acid;
3-(3-pyridinyl)-3-(3-{[4-(2-pyridinylamino)benzoyl]
   amino}phenoxy)propanoic acid;
3-(3-pyridinyl)-3-(4-{[4-(2-pyridinylamino)benzoyl]
   amino}phenoxy)propanoic acid;
3-{2-[(3-{[amino(imino)methyl]amino}benzoyl)amino]
   phenoxy}-3-(3-pyridinyl)propanoic acid;
3-{3-[(3-{[amino(imino)methyl]amino}benzoyl)amino]
   phenoxy}-3-(3-pyridinyl)propanoic acid;
3-{4-[(3-{[amino(imino)methyl]amino}benzoyl)amino]
   phenoxy}-3-(3-pyridinyl)propanoic acid;
3-{2-[(3-{[(benzylamino)(imino)methyl]amino}benzoyl)
   amino]phenoxy}-3-(3-pyridinyl)propanoic acid;
3-{3-[(3-{[(benzylamino)(imino)methyl]amino}benzoyl)
   amino]phenoxy}-3-(3-pyridinyl)propanoic acid;
3-{4-[(3-{[(benzylamino)(imino)methyl]amino}benzoyl)
   amino]phenoxy}-3-(3-pyridinyl)propanoic acid;
3-[2-({3-[(aminocarbonyl)amino]benzoyl}amino)
   phenoxy]-3-(3-pyridinyl)propanoic acid;
3-[3-({3-[(aminocarbonyl)amino]benzoyl}amino)
   phenoxy]-3-(3-pyridinyl)propanoic acid;
3-[4-({3-[(aminocarbonyl)amino]benzoyl}amino)
   phenoxy]-3-(3-pyridinyl)propanoic acid;
3-{2-[(3-{[(benzylamino)carbonyl]amino}benzoyl)amino]
   phenoxy}-3-(3-pyridinyl)propanoic acid;
3-{3-[(3-{[(benzylamino)carbonyl]amino}benzoyl)amino]
   phenoxy}-3-(3-pyridinyl)propanoic acid;
3-{4-[(3-{[(benzylamino)carbonyl]amino}benzoyl)amino]
   phenoxy}-3-(3-pyridinyl)propanoic acid;
3-(2-{[3-(4,5-dihydro-1H-imidazol-2-ylamino)benzoyl]
   amino}phenoxy)-3-(3-pyridinyl)propanoic acid;
3-(3-{[3-(4,5-dihydro-1H-imidazol-2-ylamino)benzoyl]
   amino}phenoxy)-3-(3-pyridinyl)propanoic acid;
3-(4-{[3-(4,5-dihydro-1H-imidazol-2-ylamino)benzoyl]
   amino}phenoxy)-3-(3-pyridinyl)propanoic acid;
3-(2-{[3-(1H-imidazol-2-ylamino)benzoyl]
   amino}phenoxy)-3-(3-pyridinyl)propanoic acid;
3-(3-{[3-(1H-imidazol-2-ylamino)benzoyl]
   amino}phenoxy)-3-(3-pyridinyl)propanoic acid;
3-(4-{[3-(1H-imidazol-2-ylamino)benzoyl]
   amino}phenoxy)-3-(3-pyridinyl)propanoic acid;
3-(3-pyridinyl)-3-(2-{[3-(2-pyridinylamino)benzoyl]
   amino}phenoxy)propanoic acid;
3-(3-pyridinyl)-3-(3-{[3-(2-pyridinylamino)benzoyl]
   amino}phenoxy)propanoic acid;
3-(3-pyridinyl)-3-(4-{[3-(2-pyridinylamino)benzoyl]
   amino}phenoxy)propanoic acid;
3-{2-[(3-{[amino(imino)methyl]amino}benzoyl)amino]
   phenoxy}-3-phenylpropanoic acid;
3-{3-[(3-{[amino(imino)methyl]amino}benzoyl)amino]
   phenoxy}-3-phenylpropanoic acid;
3-{4-[(3-{[amino(imino)methyl]amino}benzoyl)amino]
   phenoxy}-3-phenylpropanoic acid;
3-{2-[(3-{[(benzylamino)(imino)methyl]amino}benzoyl)
   amino]phenoxy}-3-phenylpropanoic acid;
3-{3-[(3-{[(benzylamino)(imino)methyl]amino}benzoyl)
   amino]phenoxy}-3-phenylpropanoic acid;
3-{4-[(3-{[(benzylamino)(imino)methyl]amino}benzoyl)
   amino]phenoxy}-3-phenylpropanoic acid;
3-[2-({3-[(aminocarbonyl)amino]benzoyl}amino)
   phenoxy]-3-phenylpropanoic acid;
3-[3-({3-[(aminocarbonyl)amino]benzoyl}amino)
   phenoxy]-3-phenylpropanoic acid;
3-[4-({3-[(aminocarbonyl)amino]benzoyl}amino)
   phenoxy]-3-phenylpropanoic acid;
3-{2-[(3-{[(benzylamino)carbonyl]amino}benzoyl)amino]
   phenoxy}-3-phenylpropanoic acid;
3-{3-[(3-{[(benzylamino)carbonyl]amino}benzoyl)amino]
   phenoxy}-3-phenylpropanoic acid;
3-{4-[(3-{[(benzylamino)carbonyl]amino}benzoyl)amino]
   phenoxy}-3-phenylpropanoic acid;
3-(2-{[3-(4,5-dihydro-1H-imidazol-2-ylamino)benzoyl]
   amino}phenoxy)-3-phenylpropanoic acid;
3-(3-{[3-(4,5-dihydro-1H-imidazol-2-ylamino)benzoyl]
   amino}phenoxy)-3-phenylpropanoic acid;
3-(4-{[3-(4,5-dihydro-1H-imidazol-2-ylamino)benzoyl]
   amino}phenoxy)-3-phenylpropanoic acid;
3-(2-{[3-(1H-imidazol-2-ylamino)benzoyl]
   amino}phenoxy)-3-phenylpropanoic acid;
3-(3-{[3-(1H-imidazol-2-ylamino)benzoyl]
   amino}phenoxy)-3-phenylpropanoic acid;
3-(4-{[3-(1H-imidazol-2-ylamino)benzoyl]
   amino}phenoxy)-3-phenylpropanoic acid;
3-phenyl-3-(2-{[3-(2-pyridinylamino)benzoyl]
   amino}phenoxy)propanoic acid;
3-phenyl-3-(3-{[3-(2-pyridinylamino)benzoyl]
   amino}phenoxy)propanoic acid;
3-phenyl-3-(4-{[3-(2-pyridinylamino)benzoyl]
   amino}phenoxy)propanoic acid;
3-{2-[(4-{[amino(imino)methyl]amino}benzoyl)amino]
   phenoxy}-3-phenylpropanoic acid;
3-{3-[(4-{[amino(imino)methyl]amino}benzoyl)amino]
   phenoxy}-3-phenylpropanoic acid;
3-{4-[(4-{[amino(imino)methyl]amino}benzoyl)amino]
   phenoxy}-3-phenylpropanoic acid;
3-{2-[(4-{[(benzylamino)(imino)methyl]amino}benzoyl)
   amino]phenoxy}-3-phenylpropanoic acid;
3-{3-[(4-{[(benzylamino)(imino)methyl]amino}benzoyl)
   amino]phenoxy}-3-phenylpropanoic acid;
3-{4-[(4-{[(benzylamino)(imino)methyl]amino}benzoyl)
   amino]phenoxy}-3-phenylpropanoic acid;
3-[2-({4-[(aminocarbonyl)amino]benzoyl}amino)
   phenoxy]-3-phenylpropanoic acid;
3-[3-({4-[(aminocarbonyl)amino]benzoyl}amino)
   phenoxy]-3-phenylpropanoic acid;
3-[4-({4-[(aminocarbonyl)amino]benzoyl}amino)
   phenoxy]-3-phenylpropanoic acid;
3-{2-[(4-{[(benzylamino)carbonyl]amino}benzoyl)amino]
   phenoxy}-3-phenylpropanoic acid;
3-{3-[(4-{[(benzylamino)carbonyl]amino}benzoyl)amino]
   phenoxy}-3-phenylpropanoic acid;
3-{4-[(4-{[(benzylamino)carbonyl]amino}benzoyl)amino]
   phenoxy}-3-phenylpropanoic acid;
3-(2-{[4-(4,5-dihydro-1H-imidazol-2-ylamino)benzoyl]
   amino}phenoxy)-3-phenylpropanoic acid;
3-(3-{[4-(4,5-dihydro-1H-imidazol-2-ylamino)benzoyl]
   amino}phenoxy)-3-phenylpropanoic acid;
3-(4-{[4-(4,5-dihydro-1H-imidazol-2-ylamino)benzoyl]
   amino}phenoxy)-3-phenylpropanoic acid;
3-(2-{[4-(1H-imidazol-2-ylamino)benzoyl]
   amino}phenoxy)-3-phenylpropanoic acid;
3-(3-{[4-(1H-imidazol-2-ylamino)benzoyl]
   amino}phenoxy)-3-phenylpropanoic acid;
3-(4-{[4-(1H-imidazol-2-ylamino)benzoyl]
   amino}phenoxy)-3-phenylpropanoic acid;
3-phenyl-3-(2-{[4-(2-pyridinylamino)benzoyl]
   amino}phenoxy)propanoic acid;
3-phenyl-3-(3-{[4-(2-pyridinylamino)benzoyl]
   amino}phenoxy)propanoic acid;
3-phenyl-3-(4-{[4-(2-pyridinylamino)benzoyl]
   amino}phenoxy)propanoic acid;

3-({2-[(3-{[amino(imino)methyl]amino}benzoyl)amino]phenyl}sulfinyl)-3-(3-pyridinyl)propanoic acid;
3-({3-[(3-{[amino(imino)methyl]amino}benzoyl)amino]phenyl}sulfinyl)-3-(3-pyridinyl)propanoic acid;
3-({4-[(3-{[amino(imino)methyl]amino}benzoyl)amino]phenyl}sulfinyl)-3-(3-pyridinyl)propanoic acid;
3-({2-[(3-{[(benzylamino)(imino)methyl]amino}benzoyl)amino]phenyl}sulfinyl)-3-(3-pyridinyl)propanoic acid;
3-({3-[(3-{[(benzylamino)(imino)methyl]amino}benzoyl)amino]phenyl}sulfinyl)-3-(3-pyridinyl)propanoic acid;
3-({4-[(3-{[(benzylamino)(imino)methyl]amino}benzoyl)amino]phenyl}sulfinyl)-3-(3-pyridinyl)propanoic acid;
3-{[2-({3-[(aminocarbonyl)amino]benzoyl}amino)phenyl]sulfinyl}-3-(3-pyridinyl)propanoic acid;
3-{[3-({3-[(aminocarbonyl)amino]benzoyl}amino)phenyl]sulfinyl}-3-(3-pyridinyl)propanoic acid;
3-{[4-({3-[(aminocarbonyl)amino]benzoyl}amino)phenyl]sulfinyl}-3-(3-pyridinyl)propanoic acid;
3-({2-[(3-{[(benzylamino)carbonyl]amino}benzoyl)amino]phenyl}sulfinyl)-3-(3-pyridinyl)propanoic acid;
3-({3-[(3-{[(benzylamino)carbonyl]amino}benzoyl)amino]phenyl}sulfinyl)-3-(3-pyridinyl)propanoic acid;
3-({4-[(3-{[(benzylamino)carbonyl]amino}benzoyl)amino]phenyl}sulfinyl)-3-(3-pyridinyl)propanoic acid;
3-[(2-{[3-(4,5-dihydro-1H-imidazol-2-ylamino)benzoyl]amino}phenyl)sulfinyl]-3-(3-pyridinyl)propanoic acid;
3-[(3-{[3-(4,5-dihydro-1H-imidazol-2-ylamino)benzoyl]amino}phenyl)sulfinyl]-3-(3-pyridinyl)propanoic acid;
3-[(4-{[3-(4,5-dihydro-1H-imidazol-2-ylamino)benzoyl]amino}phenyl)sulfinyl]-3-(3-pyridinyl)propanoic acid;
3-[(2-{[3-(1H-imidazol-2-ylamino)benzoyl]amino}phenyl)sulfinyl]-3-(3-pyridinyl)propanoic acid;
3-[(3-{[3-(1H-imidazol-2-ylamino)benzoyl]amino}phenyl)sulfinyl]-3-(3-pyridinyl)propanoic acid;
3-[(4-{[3-(1H-imidazol-2-ylamino)benzoyl]amino}phenyl)sulfinyl]-3-(3-pyridinyl)propanoic acid;
3-(3-pyridinyl)-3-[(2-{[3-(2-pyridinylamino)benzoyl]amino}phenyl)sulfinyl]propanoic acid;
3-(3-pyridinyl)-3-[(3-{[3-(2-pyridinylamino)benzoyl]amino}phenyl)sulfinyl]propanoic acid;
3-(3-pyridinyl)-3-[(4-{[3-(2-pyridinylamino)benzoyl]amino}phenyl)sulfinyl]propanoic acid;
3-({2-[(4-{[amino(imino)methyl]amino}benzoyl)amino]phenyl}sulfinyl)-3-(3-pyridinyl)propanoic acid;
3-({3-[(4-{[amino(imino)methyl]amino}benzoyl)amino]phenyl}sulfinyl)-3-(3-pyridinyl)propanoic acid;
3-({4-[(4-{[amino(imino)methyl]amino}benzoyl)amino]phenyl}sulfinyl)-3-(3-pyridinyl)propanoic acid;
3-({2-[(4-{[(benzylamino)(imino)methyl]amino}benzoyl)amino]phenyl}sulfinyl)-3-(3-pyridinyl)propanoic acid;
3-({3-[(4-{[(benzylamino)(imino)methyl]amino}benzoyl)amino]phenyl}sulfinyl)-3-(3-pyridinyl)propanoic acid;
3-({4-[(4-{[(benzylamino)(imino)methyl]amino}benzoyl)amino]phenyl}sulfinyl)-3-(3-pyridinyl)propanoic acid;
3-{[2-({4-[(aminocarbonyl)amino]benzoyl}amino)phenyl]sulfinyl}-3-(3-pyridinyl)propanoic acid;
3-{[3-({4-[(aminocarbonyl)amino]benzoyl}amino)phenyl]sulfinyl}-3-(3-pyridinyl)propanoic acid;
3-{[4-({4-[(aminocarbonyl)amino]benzoyl}amino)phenyl]sulfinyl}-3-(3-pyridinyl)propanoic acid;
3-({2-[(4-{[(benzylamino)carbonyl]amino}benzoyl)amino]phenyl}sulfinyl)-3-(3-pyridinyl)propanoic acid;
3-({3-[(4-{[(benzylamino)carbonyl]amino}benzoyl)amino]phenyl}sulfinyl)-3-(3-pyridinyl)propanoic acid;
3-({4-[(4-{[(benzylamino)carbonyl]amino}benzoyl)amino]phenyl}sulfinyl)-3-(3-pyridinyl)propanoic acid;
3-[(2-{[4-(4,5-dihydro-1H-imidazol-2-ylamino)benzoyl]amino}phenyl)sulfinyl]-3-(3-pyridinyl)propanoic acid;
3-[(3-{[4-(4,5-dihydro-1H-imidazol-2-ylamino)benzoyl]amino}phenyl)sulfinyl]-3-(3-pyridinyl)propanoic acid;
3-[(4-{[4-(4,5-dihydro-1H-imidazol-2-ylamino)benzoyl]amino}phenyl)sulfinyl]-3-(3-pyridinyl)propanoic acid;
3-[(2-{[4-(1H-imidazol-2-ylamino)benzoyl]amino}phenyl)sulfinyl]-3-(3-pyridinyl)propanoic acid;
3-[(3-{[4-(1H-imidazol-2-ylamino)benzoyl]amino}phenyl)sulfinyl]-3-(3-pyridinyl)propanoic acid;
3-[(4-{[4-(1H-imidazol-2-ylamino)benzoyl]amino}phenyl)sulfinyl]-3-(3-pyridinyl)propanoic acid;
3-(3-pyridinyl)-3-[(2-{[4-(2-pyridinylamino)benzoyl]amino}phenyl)sulfinyl]propanoic acid;
3-(3-pyridinyl)-3-[(3-{[4-(2-pyridinylamino)benzoyl]amino}phenyl)sulfinyl]propanoic acid;
3-(3-pyridinyl)-3-[(4-{[4-(2-pyridinylamino)benzoyl]amino}phenyl)sulfinyl]propanoic acid;
3-({2-[(3-{[amino(imino)methyl]amino}benzoyl)amino]phenyl}sulfonyl)-3-(3-pyridinyl)propanoic acid;
3-({3-[(3-{[amino(imino)methyl]amino}benzoyl)amino]phenyl}sulfonyl)-3-(3-pyridinyl)propanoic acid;
3-({4-[(3-{[amino(imino)methyl]amino}benzoyl)amino]phenyl}sulfonyl)-3-(3-pyridinyl)propanoic acid;
3-({2-[(3-{[(benzylamino)(imino)methyl]amino}benzoyl)amino]phenyl}sulfonyl)-3-(3-pyridinyl)propanoic acid;
3-({3-[(3-{[(benzylamino)(imino)methyl]amino}benzoyl)amino]phenyl}sulfonyl)-3-(3-pyridinyl)propanoic acid;
3-({4-[(3-{[(benzylamino)(imino)methyl]amino}benzoyl)amino]phenyl}sulfonyl)-3-(3-pyridinyl)propanoic acid;
3-{[2-({3-[(aminocarbonyl)amino]benzoyl}amino)phenyl]sulfonyl}-3-(3-pyridinyl)propanoic acid;
3-{[3-({3-[(aminocarbonyl)amino]benzoyl}amino)phenyl]sulfonyl}-3-(3-pyridinyl)propanoic acid;
3-{[4-({3-[(aminocarbonyl)amino]benzoyl}amino)phenyl]sulfonyl}-3-(3-pyridinyl)propanoic acid;
3-({2-[(3-{[(benzylamino)carbonyl]amino}benzoyl)amino]phenyl}sulfonyl)-3-(3-pyridinyl)propanoic acid;
3-({3-[(3-{[(benzylamino)carbonyl]amino}benzoyl)amino]phenyl}sulfonyl)-3-(3-pyridinyl)propanoic acid;
3-({4-[(3-{[(benzylamino)carbonyl]amino}benzoyl)amino]phenyl}sulfonyl)-3-(3-pyridinyl)propanoic acid;
3-[(2-{[3-(4,5-dihydro-1H-imidazol-2-ylamino)benzoyl]amino}phenyl)sulfonyl]-3-(3-pyridinyl)propanoic acid;
3-[(3-{[3-(4,5-dihydro-1H-imidazol-2-ylamino)benzoyl]amino}phenyl)sulfonyl]-3-(3-pyridinyl)propanoic acid;
3-[(4-{[3-(4,5-dihydro-1H-imidazol-2-ylamino)benzoyl]amino}phenyl)sulfonyl]-3-(3-pyridinyl)propanoic acid;
3-[(2-{[3-(1H-imidazol-2-ylamino)benzoyl]amino}phenyl)sulfonyl]-3-(3-pyridinyl)propanoic acid;
3-[(3-{[3-(1H-imidazol-2-ylamino)benzoyl]amino}phenyl)sulfonyl]-3-(3-pyridinyl)propanoic acid;
3-[(4-{[3-(1H-imidazol-2-ylamino)benzoyl]amino}phenyl)sulfonyl]-3-(3-pyridinyl)propanoic acid;
3-(3-pyridinyl)-3-[(2-{[3-(2-pyridinylamino)benzoyl]amino}phenyl)sulfonyl]propanoic acid;
3-(3-pyridinyl)-3-[(3-{[3-(2-pyridinylamino)benzoyl]amino}phenyl)sulfonyl]propanoic acid;
3-(3-pyridinyl)-3-[(4-{[3-(2-pyridinylamino)benzoyl]amino}phenyl)sulfonyl]propanoic acid;
3-({2-[(4-{[amino(imino)methyl]amino}benzoyl)amino]phenyl}sulfonyl)-3-(3-pyridinyl)propanoic acid;
3-({3-[(4-{[amino(imino)methyl]amino}benzoyl)amino]phenyl}sulfonyl)-3-(3-pyridinyl)propanoic acid;
3-({4-[(4-{[amino(imino)methyl]amino}benzoyl)amino]phenyl}sulfonyl)-3-(3-pyridinyl)propanoic acid;
3-({2-[(4-{[(benzylamino)(imino)methyl]amino}benzoyl)amino]phenyl}sulfonyl)-3-(3-pyridinyl)propanoic acid;
3-({3-[(4-{[(benzylamino)(imino)methyl]amino}benzoyl)amino]phenyl}sulfonyl)-3-(3-pyridinyl)propanoic acid;

3-({4-[(4-{[(benzylamino)(imino)methyl]amino}benzoyl)amino]phenyl}sulfonyl)-3-(3-pyridinyl)propanoic acid;
3-{[2-({4-[(aminocarbonyl)amino]benzoyl}amino)phenyl]sulfonyl}-3-(3-pyridinyl)propanoic acid;
3-{[3-({4-[(aminocarbonyl)amino]benzoyl}amino)phenyl]sulfonyl}-3-(3-pyridinyl)propanoic acid;
3-{[4-({4-[(aminocarbonyl)amino]benzoyl}amino)phenyl]sulfonyl}-3-(3-pyridinyl)propanoic acid;
3-({2-[(4-{[(benzylamino)carbonyl]amino}benzoyl)amino]phenyl}sulfonyl)-3-(3-pyridinyl)propanoic acid;
3-({3-[(4-{[(benzylamino)carbonyl]amino}benzoyl)amino]phenyl}sulfonyl)-3-(3-pyridinyl)propanoic acid;
3-({4-[(4-{[(benzylamino)carbonyl]amino}benzoyl)amino]phenyl}sulfonyl)-3-(3-pyridinyl)propanoic acid;
3-[(2-{[4-(4,5-dihydro-1H-imidazol-2-ylamino)benzoyl]amino}phenyl)sulfonyl]-3-(3-pyridinyl)propanoic acid;
3-[(3-{[4-(4,5-dihydro-1H-imidazol-2-ylamino)benzoyl]amino}phenyl)sulfonyl]-3-(3-pyridinyl)propanoic acid;
3-[(4-{[4-(4,5-dihydro-1H-imidazol-2-ylamino)benzoyl]amino}phenyl)sulfonyl]-3-(3-pyridinyl)propanoic acid;
3-[(2-{[4-(1H-imidazol-2-ylamino)benzoyl]amino}phenyl)sulfonyl]-3-(3-pyridinyl)propanoic acid;
3-[(3-{[4-(1H-imidazol-2-ylamino)benzoyl]amino}phenyl)sulfonyl]-3-(3-pyridinyl)propanoic acid;
3-[(4-{[4-(1H-imidazol-2-ylamino)benzoyl]amino}phenyl)sulfonyl]-3-(3-pyridinyl)propanoic acid;
3-(3-pyridinyl)-3-[(2-{[4-(2-pyridinylamino)benzoyl]amino}phenyl)sulfonyl]propanoic acid;
3-(3-pyridinyl)-3-[(3-{[4-(2-pyridinylamino)benzoyl]amino}phenyl)sulfonyl]propanoic acid;
3-(3-pyridinyl)-3-[(4-{[4-(2-pyridinylamino)benzoyl]amino}phenyl)sulfonyl]propanoic acid;
3-({3-[(3-{[amino(imino)methyl]amino}benzoyl)amino]phenyl}sulfinyl)-3-phenylpropanoic acid;
3-({2-[(3-{[amino(imino)methyl]amino}benzoyl)amino]phenyl}sulfinyl)-3-phenylpropanoic acid;
3-({4-[(3-{[amino(imino)methyl]amino}benzoyl)amino]phenyl}sulfinyl)-3phenylpropanoic acid;
3-({2-[(3-{[(benzylamino)(imino)methyl]amino}benzoyl)amino]phenyl}sulfinyl)-3-phenylpropanoic acid;
3-({3-[(3-{[(benzylamino)(imino)methyl]amino}benzoyl)amino]phenyl}sulfinyl)-3-phenylpropanoic acid;
3-({4-[(3-{[(benzylamino)(imino)methyl]amino}benzoyl)amino]phenyl}sulfinyl)-3-phenylpropanoic acid;
3-{[2-({3-[(aminocarbonyl)amino]benzoyl}amino)phenyl]sulfinyl}-3-phenylpropanoic acid;
3-{[3-({3-[(aminocarbonyl)amino]benzoyl}amino)phenyl]sulfinyl}-3-phenylpropanoic acid;
3-{[4-({3-[(aminocarbonyl)amino]benzoyl}amino)phenyl]sulfinyl}-3-phenylpropanoicacid;
3-({2-[(3-{[(benzylamino)carbonyl]amino}benzoyl)amino]phenyl}sulfinyl)-3-phenylpropanoic acid;
3-({3-[(3-{[(benzylamino)carbonyl]amino}benzoyl)amino]phenyl}sulfinyl)-3-phenylpropanoic acid;
3-({4-[(3-{[(benzylamino)carbonyl]amino}benzoyl)amino]phenyl}sulfinyl)-3-phenylpropanoic acid;
3-[(2-{[3-(4,5-dihydro-1H-imidazol-2-ylamino)benzoyl]amino}phenyl)sulfinyl]-3-phenylpropanoic acid;
3-[(3-{[3-(4,5-dihydro-1H-imidazol-2-ylamino)benzoyl]amino}phenyl)sulfinyl]-3-phenylpropanoic acid;
3-[(4-{[3-(4,5-dihydro-1H-imidazol-2-ylamino)benzoyl]amino}phenyl)sulfinyl]-3-phenylpropanoicacid;
3-[(2-{[3-(1H-imidazol-2-ylamino)benzoyl]amino}phenyl)sulfinyl]-3-phenylpropanoic acid;
3-[(3-{[3-(1H-imidazol-2-ylamino)benzoyl]amino}phenyl)sulfinyl]-3-phenylpropanoic acid;
3-[(4-{[3-(1H-imidazol-2-ylamino)benzoyl]amino}phenyl)sulfinyl]-3-phenylpropanoic acid;
3-phenyl-3-[(2-{[3-(2-pyridinylamino)benzoyl]amino}phenyl)sulfinyl]propanoic acid;
3-phenyl-3-[(3-{[3-(2-pyridinylamino)benzoyl]amino}phenyl)sulfinyl]propanoic acid;
3-phenyl-3-[(4-{[3-(2-pyridinylamino)benzoyl]amino}phenyl)sulfinyl]propanoic acid;
3-({2-[(4-{[amino(imino)methyl]amino}benzoyl)amino]phenyl}sulfinyl)-3-phenylpropanoic acid;
3-({3-[(4-{[amino(imino)methyl]amino}benzoyl)amino]phenyl}sulfinyl)-3-phenylpropanoic acid;
3-({4-[(4-{[amino(imino)methyl]amino}benzoyl)amino]phenyl}sulfinyl)-3-phenylpropanoic acid;
3-({2-[(4-{[(benzylamino)(imino)methyl]amino}benzoyl)amino]phenyl}sulfinyl)-3-phenylpropanoic acid;
3-({3-[(4-{[(benzylamino)(imino)methyl]amino}benzoyl)amino]phenyl}sulfinyl)-3-phenylpropanoic acid;
3-({4-[(4-{[(benzylamino)(imino)methyl]amino}benzoyl)amino]phenyl}sulfinyl)-3-phenylpropanoic acid;
3-{[2-({4-[(aminocarbonyl)amino]benzoyl}amino)phenyl]sulfinyl}-3-phenylpropanoic acid;
3-{[3-({4-[(aminocarbonyl)amino]benzoyl}amino)phenyl]sulfinyl}-3-phenylpropanoic acid;
3-{[4-({4-[(aminocarbonyl)amino]benzoyl}amino)phenyl]sulfinyl}-3-phenylpropanoicacid;
3-({2-[(4-{[(benzylamino)carbonyl]amino}benzoyl)amino]phenyl}sulfinyl)-3-phenylpropanoic acid;
3-({3-[(4-{[(benzylamino)carbonyl]amino}benzoyl)amino]phenyl}sulfinyl)-3-phenylpropanoic acid;
3-({4-[(4-{[(benzylamino)carbonyl]amino}benzoyl)amino]phenyl}sulfinyl)-3-phenylpropanoic acid;
3-[(2-{[4-(4,5-dihydro-1H-imidazol-2-ylamino)benzoyl]amino}phenyl)sulfinyl]-3-phenylpropanoic acid;
3-[(3-{[4-(4,5-dihydro-1H-imidazol-2-ylamino)benzoyl]amino}phenyl)sulfinyl]-3-phenylpropanoic acid;
3-[(4-{[4-(4,5-dihydro-1H-imidazol-2-ylamino)benzoyl]amino}phenyl)sulfinyl]-3-phenylpropanoicacid;
3-[(2-{[4-(1H-imidazol-2-ylamino)benzoyl]amino}phenyl)sulfinyl]-3-phenylpropanoic acid;
3-[(3-{[4-(1H-imidazol-2-ylamino)benzoyl]amino}phenyl)sulfinyl]-3-phenylpropanoic acid;
3-[(4-{[4-(1H-imidazol-2-ylamino)benzoyl]amino}phenyl)sulfinyl]-3-phenylpropanoic acid;
3-phenyl-3-[(2-{[4-(2-pyridinylamino)benzoyl]amino}phenyl)sulfinyl]propanoic acid;
3-phenyl-3-[(3-{[4-(2-pyridinylamino)benzoyl]amino}phenyl)sulfinyl]propanoic acid;
3-phenyl-3-[(4-{[4-(2-pyridinylamino)benzoyl]amino}phenyl)sulfinyl]propanoic acid;
3-({3-[(3-{[amino(imino)methyl]amino}benzoyl)amino]phenyl}sulfonyl)-3-phenylpropanoic acid;
3-({2-[(3-{[amino(imino)methyl]amino}benzoyl)amino]phenyl}sulfonyl)-3-phenylpropanoic acid;
3-({4-[(3-{[amino(imino)methyl]amino}benzoyl)amino]phenyl}sulfonyl)-3phenylpropanoic acid;
3-({2-[(3-{[(benzylamino)(imino)methyl]amino}benzoyl)amino]phenyl}sulfonyl)-3-phenylpropanoic acid;
3-({3-[(3-{[(benzylamino)(imino)methyl]amino}benzoyl)amino]phenyl}sulfonyl)-3-phenylpropanoic acid;
3-({4-[(3-{[(benzylamino)(imino)methyl]amino}benzoyl)amino]phenyl}sulfonyl)-3-phenylpropanoic acid;
3-{[2-({3-[(aminocarbonyl)amino]benzoyl}amino)phenyl]sulfonyl}-3-phenylpropanoic acid;
3-{[3-({3-[(aminocarbonyl)amino]benzoyl}amino)phenyl]sulfonyl}-3-phenylpropanoic acid;
3-{[4-({3-[(aminocarbonyl)amino]benzoyl}amino)phenyl]sulfonyl}-3-phenylpropanoicacid;
3-({2-[(3-{[(benzylamino)carbonyl]amino}benzoyl)amino]phenyl}sulfonyl)-3-phenylpropanoic acid;

3-({3-[(3-{[(benzylamino)carbonyl]amino}benzoyl)amino]
    phenyl}sulfonyl)-3-phenylpropanoic acid;
3-({4-[(3-{[(benzylamino)carbonyl]amino}benzoyl)amino]
    phenyl}sulfonyl)-3-phenylpropanoic acid;
3-[(2-{[3-(4,5-dihydro-1H-imidazol-2-ylamino)benzoyl]
    amino}phenyl)sulfonyl]-3-phenylpropanoic acid;
3-[(3-{[3-(4,5-dihydro-1H-imidazol-2-ylamino)benzoyl]
    amino}phenyl)sulfonyl]-3-phenylpropanoic acid;
3-[(4-{[3-(4,5-dihydro-1H-imidazol-2-ylamino)benzoyl]
    amino}phenyl)sulfonyl]-3-phenylpropanoicacid;
3-[(2-{[3-(1H-imidazol-2-ylamino)benzoyl]amino}phenyl)
    sulfonyl]-3-phenylpropanoic acid;
3-[(3-{[3-(1H-imidazol-2-ylamino)benzoyl]amino}phenyl)
    sulfonyl]-3-phenylpropanoic acid;
3-[(4-{[3-(1H-imidazol-2-ylamino)benzoyl]amino}phenyl)
    sulfonyl]-3-phenylpropanoic acid;
3-phenyl-3-[(2-{[3-(2-pyridinylamino)benzoyl]
    amino}phenyl)sulfonyl]propanoic acid;
3-phenyl-3-[(3-{[3-(2-pyridinylamino)benzoyl]
    amino}phenyl)sulfonyl]propanoic acid;
3-phenyl-3-[(4-{[3-(2-pyridinylamino)benzoyl]
    amino}phenyl)sulfonyl]propanoic acid;
3-({2-[(4-{[amino(imino)methyl]amino}benzoyl)amino]
    phenyl}sulfonyl)-3-phenylpropanoic acid;
3-({3-[(4-{[amino(imino)methyl]amino}benzoyl)amino]
    phenyl}sulfonyl)-3-phenylpropanoic acid;
3-({4-[(4-{[amino(imino)methyl]amino}benzoyl)amino]
    phenyl}sulfonyl)-3-phenylpropanoic acid;
3-({2-[(4-{[(benzylamino)(imino)methyl]amino}benzoyl)
    amino]phenyl}sulfonyl)-3-phenylpropanoic acid;
3-({3-[(4-{[(benzylamino)(imino)methyl]amino}benzoyl)
    amino]phenyl}sulfonyl)-3-phenylpropanoic acid;
3-({4-[(4-{[(benzylamino)(imino)methyl]amino}benzoyl)
    amino]phenyl}sulfonyl)-3-phenylpropanoic acid;
3-{[2-({4-[(aminocarbonyl)amino]benzoyl}amino)phenyl]
    sulfonyl}-3-phenylpropanoic acid;
3-{[3-({4-[(aminocarbonyl)amino]benzoyl}amino)phenyl]
    sulfonyl}-3-phenylpropanoic acid;
3-{[4-({4-[(aminocarbonyl)amino]benzoyl}amino)phenyl]
    sulfonyl}-3-phenylpropanoicacid;
3-({2-[(4-{[(benzylamino)carbonyl]amino}benzoyl)amino]
    phenyl}sulfonyl)-3-phenylpropanoic acid;
3-({3-[(4-{[(benzylamino)carbonyl]amino}benzoyl)amino]
    phenyl}sulfonyl)-3-phenylpropanoic acid;
3-({4-[(4-{[(benzylamino)carbonyl]amino}benzoyl)amino]
    phenyl}sulfonyl)-3-phenylpropanoic acid;
3-[(2-{[4-(4,5-dihydro-1H-imidazol-2-ylamino)benzoyl]
    amino}phenyl)sulfonyl]-3-phenylpropanoic acid;
3-[(3-{[4-(4,5-dihydro-1H-imidazol-2-ylamino)benzoyl]
    amino}phenyl)sulfonyl]-3-phenylpropanoic acid;
3-[(4-{[4-(4,5-dihydro-1H-imidazol-2-ylamino)benzoyl]
    amino}phenyl)sulfonyl]-3-phenylpropanoicacid;
3-[(2-{[4-(1H-imidazol-2-ylamino)benzoyl]amino}phenyl)
    sulfonyl]-3-phenylpropanoic acid;
3-[(3-{[4-(1H-imidazol-2-ylamino)benzoyl]amino}phenyl)
    sulfonyl]-3-phenylpropanoic acid;
3-[(4-{[4-(1H-imidazol-2-ylamino)benzoyl]amino}phenyl)
    sulfonyl]-3-phenylpropanoic acid;
3-phenyl-3-[(2-{[4-(2-pyridinylamino)benzoyl]
    amino}phenyl)sulfonyl]propanoic acid;
3-phenyl-3-[(3-{[4-(2-pyridinylamino)benzoyl]
    amino}phenyl)sulfonyl]propanoic acid;
3-phenyl-3-[(4-{[4-(2-pyridinylamino)benzoyl]
    amino}phenyl)sulfonyl]propanoic acid;
3-phenyl-3-[(2-{[4-(2-pyridinylamino)benzoyl]
    amino}phenyl)sulfonyl]propanoic acid;
3-phenyl-3-[(3-{[4-(2-pyridinylamino)benzoyl]
    amino}phenyl)sulfonyl]propanoic acid;
3-phenyl-3-[(4-{[4-(2-pyridinylamino)benzoyl]
    amino}phenyl)sulfonyl]propanoic acid;
3-(3-pyridinyl)-3-(2-{[3-(1,4,5,6-tetrahydro-2-
    pyrimidinylamino)benzoyl]amino}phenoxy)propanoic
    acid;
3-(3-pyridinyl)-3-(3-{[3-(1,4,5,6-tetrahydro-2-
    pyrimidinylamino)benzoyl]amino}phenoxy)propanoic
    acid;
3-(3-pyridinyl)-3-(4-{[3-(1,4,5,6-tetrahydro-2-
    pyrimidinylamino)benzoyl]amino}phenoxy)propanoic
    acid;
3-(3-pyridinyl)-3-(2-{[4-(1,4,5,6-tetrahydro-2-
    pyrimidinylamino)benzoyl]amino}phenoxy)propanoic
    acid;
3-(3-pyridinyl)-3-(3-{[4-(1,4,5,6-tetrahydro-2-
    pyrimidinylamino)benzoyl]amino}phenoxy)propanoic
    acid;
3-(3-pyridinyl)-3-(4-{[4-(1,4,5,6-tetrahydro-2-
    pyrimidinylamino)benzoyl]amino}phenoxy)propanoic
    acid;
3-phenyl-3-(2-{[3-(1,4,5,6-tetrahydro-2-pyrimidinylamino)
    benzoyl]amino}phenoxy)propanoic acid;
3-phenyl-3-(3-{[3-(1,4,5,6-tetrahydro-2-pyrimidinylamino)
    benzoyl]amino}phenoxy)propanoic acid;
3-phenyl-3-(4-{[3-(1,4,5,6-tetrahydro-2-pyrimidinylamino)
    benzoyl]amino}phenoxy)propanoic acid;
3-phenyl-3-(2-{[4-(1,4,5,6-tetrahydro-2-pyrimidinylamino)
    benzoyl]amino}phenoxy)propanoic acid;
3-phenyl-3-(3-{[4-(1,4,5,6-tetrahydro-2-pyrimidinylamino)
    benzoyl]amino}phenoxy)propanoic acid;
3-phenyl-3-(4-{[4-(1,4,5,6-tetrahydro-2-pyrimidinylamino)
    benzoyl]amino}phenoxy)propanoic acid;
3-(3-pyridinyl)-3-[(2-{[3-(1,4,5,6-tetrahydro-2-
    pyrimidinylamino)benzoyl]amino}phenyl)sulfanyl]
    propanoic acid;
3-(3-pyridinyl)-3-[(3-{[3-(1,4,5,6-tetrahydro-2-
    pyrimidinylamino)benzoyl]amino}phenyl)sulfanyl]
    propanoic acid;
3-(3-pyridinyl)-3-[(4-{[3-(1,4,5,6-tetrahydro-2-
    pyrimidinylamino)benzoyl]amino}phenyl)sulfanyl]
    propanoic acid;
3-(3-pyridinyl)-3-[(2-{[4-(1,4,5,6-tetrahydro-2-
    pyrimidinylamino)benzoyl]amino}phenyl)sulfanyl]
    propanoic acid;
3-(3-pyridinyl)-3-[(3-{[4-(1,4,5,6-tetrahydro-2-
    pyrimidinylamino)benzoyl]amino}phenyl)sulfanyl]
    propanoic acid;
3-(3-pyridinyl)-3-[(4-{[4-(1,4,5,6-tetrahydro-2-
    pyrimidinylamino)benzoyl]amino}phenyl)sulfanyl]
    propanoic acid;
3-phenyl-3-[(2-{[3-(1,4,5,6-tetrahydro-2-pyrimi-
    dinylamino)benzoyl]amino}phenyl)sulfanyl]propanoic
    acid;
3-phenyl-3-[(3-{[3-(1,4,5,6-tetrahydro-2-pyrimi-
    dinylamino)benzoyl]amino}phenyl)sulfanyl]propanoic
    acid;
3-phenyl-3-[(4-{[3-(1,4,5,6-tetrahydro-2-pyrimi-
    dinylamino)benzoyl]amino}phenyl)sulfanyl]propanoic
    acid;
3-phenyl-3-[(2-{[4-(1,4,5,6-tetrahydro-2-pyrimi-
    dinylamino)benzoyl]amino}phenyl)sulfanyl]propanoic
    acid;
3-phenyl-3-[(3-{[4-(1,4,5,6-tetrahydro-2-pyrimi-
    dinylamino)benzoyl]amino}phenyl)sulfanyl]propanoic
    acid;
3-phenyl-3-[(4-{[4-(1,4,5,6-tetrahydro-2-pyrimi-
    dinylamino)benzoyl]amino}phenyl)sulfanyl]propanoic
    acid;

3-(3-pyridinyl)-3-[(2-{[3-(1,4,5,6-tetrahydro-2-pyrimidinylamino)benzoyl]amino}phenyl)sulfinyl]propanoic acid;
3-(3-pyridinyl)-3-[(3-{[3-(1,4,5,6-tetrahydro-2-pyrimidinylamino)benzoyl]amino}phenyl)sulfinyl]propanoic acid;
3-(3-pyridinyl)-3-[(4-{[3-(1,4,5,6-tetrahydro-2-pyrimidinylamino)benzoyl]amino}phenyl)sulfinyl]propanoic acid;
3-(3-pyridinyl)-3-[(2-{[4-(1,4,5,6-tetrahydro-2-pyrimidinylamino)benzoyl]amino}phenyl)sulfinyl]propanoic acid;
3-(3-pyridinyl)-3-[(3-{[4-(1,4,5,6-tetrahydro-2-pyrimidinylamino)benzoyl]amino}phenyl)sulfinyl]propanoic acid;
3-(3-pyridinyl)-3-[(4-{[4-(1,4,5,6-tetrahydro-2-pyrimidinylamino)benzoyl]amino}phenyl)sulfinyl]propanoic acid;
3-phenyl-3-[(2-{[3-(1,4,5,6-tetrahydro-2-pyrimidinylamino)benzoyl]amino}phenyl)sulfinyl]propanoic acid;
3-phenyl-3-[(3-{[3-(1,4,5,6-tetrahydro-2-pyrimidinylamino)benzoyl]amino}phenyl)sulfinyl]propanoic acid;
3-phenyl-3-[(4-{[3-(1,4,5,6-tetrahydro-2-pyrimidinylamino)benzoyl]amino}phenyl)sulfinyl]propanoic acid;
3-phenyl-3-[(2-{[4-(1,4,5,6-tetrahydro-2-pyrimidinylamino)benzoyl]amino}phenyl)sulfinyl]propanoic acid;
3-phenyl-3-[(3-{[4-(1,4,5,6-tetrahydro-2-pyrimidinylamino)benzoyl]amino}phenyl)sulfinyl]propanoic acid;
3-phenyl-3-[(4-{[4-(1,4,5,6-tetrahydro-2-pyrimidinylamino)benzoyl]amino}phenyl)sulfinyl]propanoic acid;
3-(3-pyridinyl)-3-[(2-{[3-(1,4,5,6-tetrahydro-2-pyrimidinylamino)benzoyl]amino}phenyl)sulfonyl]propanoic acid;
3-(3-pyridinyl)-3-[(3-{[3-(1,4,5,6-tetrahydro-2-pyrimidinylamino)benzoyl]amino}phenyl)sulfonyl]propanoic acid;
3-(3-pyridinyl)-3-[(4-{[3-(1,4,5,6-tetrahydro-2-pyrimidinylamino)benzoyl]amino}phenyl)sulfonyl]propanoic acid;
3-(3-pyridinyl)-3-[(2-{[4-(1,4,5,6-tetrahydro-2-pyrimidinylamino)benzoyl]amino}phenyl)sulfonyl]propanoic acid;
3-(3-pyridinyl)-3-[(3-{[4-(1,4,5,6-tetrahydro-2-pyrimidinylamino)benzoyl]amino}phenyl)sulfonyl]propanoic acid;
3-(3-pyridinyl)-3-[(4-{[4-(1,4,5,6-tetrahydro-2-pyrimidinylamino)benzoyl]amino}phenyl)sulfonyl]propanoic acid;
3-phenyl-3-[(2-{[3-(1,4,5,6-tetrahydro-2-pyrimidinylamino)benzoyl]amino}phenyl)sulfonyl]propanoic acid;
3-phenyl-3-[(3-{[3-(1,4,5,6-tetrahydro-2-pyrimidinylamino)benzoyl]amino}phenyl)sulfonyl]propanoic acid;
3-phenyl-3-[(4-{[3-(1,4,5,6-tetrahydro-2-pyrimidinylamino)benzoyl]amino}phenyl)sulfonyl]propanoic acid;
3-phenyl-3-[(2-{[4-(1,4,5,6-tetrahydro-2-pyrimidinylamino)benzoyl]amino}phenyl)sulfonyl]propanoic acid;
3-phenyl-3-[(3-{[4-(1,4,5,6-tetrahydro-2-pyrimidinylamino)benzoyl]amino}phenyl)sulfonyl]propanoic acid; and
3-phenyl-3-[(4-{[4-(1,4,5,6-tetrahydro-2-pyrimidinylamino)benzoyl]amino}phenyl)sulfonyl]propanoic acid;

either as a single isomer or as a mixture thereof, or a pharmaceutically acceptable salt thereof, in particular the hydrochloride or the trifluoroacetate.

A further object of the present invention is to provide a compound of formula (I)

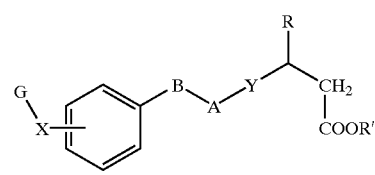

I wherein:

G is a group selected among:

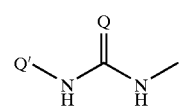

a)

wherein Q is NH or O and Q' is H, C1–C6 alkyl, phenyl, or phenyl-C1–C4-alkyl;

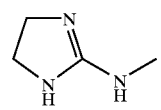

b)

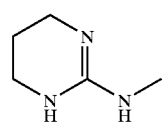

c)

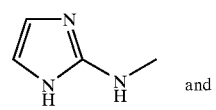

and d)

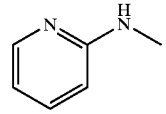

e)

X is a direct linkage, $CH_2$—CONH, —$(CH_2)_m$— or $(CH_2)_m$—X' wherein X' is O, S or NH and m is an integer of 1 to 4;

B is CONH, $CH_2$—CONH, a $C_2$–$C_4$ alkylene or $C_2$–$C_4$ alkenylene chain or —$(CH_2)_m$—X', wherein X' and m are as defined above;

A is a phenyl or pyridine ring, unsubstituted or optionally substituted by one to three substituents chosen independently from halogen, $CF_3$, $C_1$–$C_4$ alkyl, OH and $C_1$–$C_4$ alkoxy;

Y is selected from O or $S(O)_n$ wherein n is zero, 1 or 2;

R is $C_1$–$C_6$ alkyl or a phenyl or $C_5$–$C_7$ monocyclic heteroaryl ring containing one to three heteroatoms chosen from O, S, and N, unsubstituted or optionally substituted by one to three substituents chosen independently from halogen, $CF_3$, $C_1$–$C_4$ alkyl, hydroxy and $C_1$–$C_4$ alkoxy;

R' is hydrogen, $C_1$–$C_6$ alkyl, $C_2$–$C_4$ alkenyl, $C_2$–$C_4$ alkynyl, aryl or aryl-$C_1$–$C_4$ alkyl;

or a pharmaceutically acceptable salt thereof, for use in a method of treatment of the human or animal body by therapy, in particular for treating conditions mediated by the αvβ3 integrin.

Object of the present invention is also to provide a pharmaceutical composition comprising a pharmaceutically acceptable carrier and/or diluent and as an active principle, a compound of formula (I), as herein defined, or a pharmaceutically acceptable salt thereof.

The present invention also provides the use of a compound of formula (I), as defined above, in the preparation of a medicament having αvβ3 integrin inhibiting or antagonizing activity.

The present invention also provides a method for treating conditions mediated by the αvβ3 integrin in a mammal, including humans, in need of such treatment comprising administering to said mammal an effective αvβ3 inhibiting or antagonizing amount of a compound of formula (I)

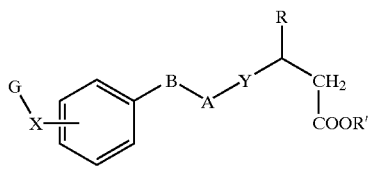

I wherein:

G is a group selected among:

a)

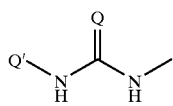

wherein Q is NH or O and Q' is H, C1–C6 alkyl, phenyl, or phenyl-C1–C4-alkyl;

b)

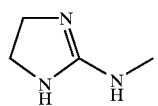

c)

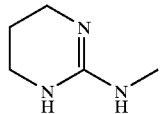

d)

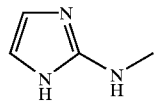

and e)

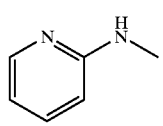

X is a direct linkage, $CH_2$—CONH, —$(CH_2)_m$— or $(CH_2)_m$—X' wherein X' is O, S or NH and m is an integer of 1 to 4;

B is CONH, $CH_2$—CONH, a $C_2$–$C_4$ alkylene or $C_2$–$C_4$ alkenylene chain or —$(CH_2)_m$—X', wherein X' and m are as defined above;

A is a phenyl or pyridine ring, unsubstituted or optionally substituted by one to three substituents chosen independently from halogen, $CF_3$, $C_1$–$C_4$ alkyl, OH and $C_1$–$C_4$ alkoxy;

Y is selected from O or $S(O)_n$ wherein n is zero, 1 or 2;

R is $C_1$–$C_6$ alkyl or a phenyl or $C_5$–$C_7$ monocyclic heteroaryl ring containing one to three heteroatoms chosen from O, S, and N, unsubstituted or optionally substituted by one to three substituents chosen independently from halogen, $CF_3$, $C_1$–$C_4$ alkyl, hydroxy and $C_1$–$C_4$ alkoxy;

R' is hydrogen, $C_1$–$C_6$ alkyl, $C_2$–$C_4$ alkenyl, $C_2$–$C_4$ alkynyl, aryl or aryl-$C_1$–$C_4$ alkyl;

or a pharmaceutically acceptable salt thereof.

More specifically, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

The compounds of the invention and the salt thereof can be prepared by and analogy process. Accordingly, the compounds of formula I and the salts thereof, can be for instance obtained by a process which comprises:

a) reacting a compound of formula II

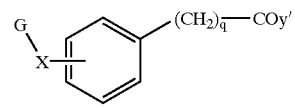

II where q is zero or 1, y' is a reactive function, preferably halogen, and G and X are as defined above, with a compound of formula III

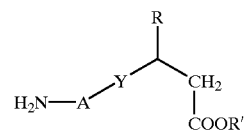

III where A, Y, R, and R' are as defined above, thus obtaining a compound of formula I where B is CONH or CH2—CONH; or b) reacting a compound of formula IV

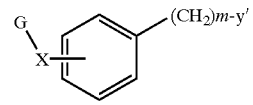

IV where y' is a reactive function, preferably halogen and G, X and m are as defined above, with a compound of formula V

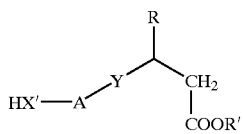

where X', A, Y, R, and R' are as defined above, thus obtaining a compound of formula I where B is —(CH$_2$)$_m$—X', wherein X' and m are as defined above; or c) reacting a compound of formula VI

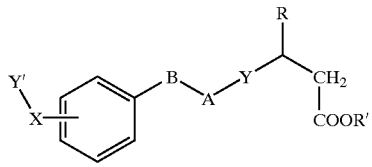

where X, B, A, Y, R, and R' are as defined above, and Y' is NH$_2$, with a suitable guanilating agent such as di-Boc-trifylguanidine, thus obtaining a compound of formula I where G is a guanidino group; or d) reacting a compound of formula VI where X, B, A, Y, R, R' and Y' are as defined above, with a benzyl cyanate or a cyanate salt, as e.g. a ammonium or sodium or potassium salt, thus obtaining a compound of formula I where G is an urea group; or e) reacting a compound of formula VI where X, B, A, Y, R, R' and Y' are as defined above, with an isocyanate of formula Q'NCO, where Q' is a group selected among C1–C6 alkyl, Phenyl, Phenyl-C1–C4-alkyl, thus obtaining a compound of formula I where G is a Q'NH(CO)NH— group, in which Q' is a group selected among C1–C6 alkyl, Phenyl, Phenyl-C1–C4-alkyl;

f) reacting a compound of formula VII

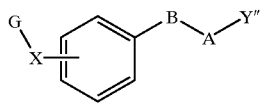

wherein G, X, B and A, are as defined above and Y" is a thiol group, with a compound of formula VIII,

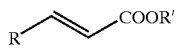

wherein R and R' are as defined above, thus obtaining a compound of formula (I) wherein Y is —S—; or g) reacting a compound of formula IX

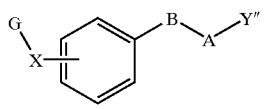

wherein G, X, B, A, are as defined above and Y" is a group Y—H with a compound of formula X,

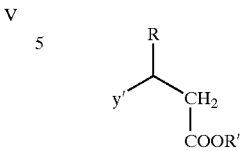

wherein R, R' and y' are as defined above, thus obtaining a compound of formula I;

h) hydrolyzing, preferably in acidic conditions, a carboxylic ester compound of formula I wherein G, X, B, A, Y, R are as defined above and R' is different from hydrogen, thus obtaining a compound of formula I wherein R' is hydrogen;

i) oxidizing with a suitable agent such as NaIO$_4$ or oxone or H$_2$O$_2$, a compound of formula I wherein G, X, B, A, R and R' are as defined above and Y is sulfur, thus obtaining a compound of formula I wherein G, X, B, A, R and R' are as defined above and Y is S(O)$_n$ wherein n is 1 or 2, i.e. Y is a sulfoxide or sulfone group;

l) cleaving a compound of formula I, wherein G, X, B, A, Y and R are as defined above and the group R' is represented by Wang (p-bezyloxybenzylalcohol) resin, with TFA in CH$_2$Cl$_2$, thus obtaining a compound of formula I wherein R' is hydrogen; and, if desired, salifying a compound of formula (I) and/or, if desired, converting a salt of a compound of formula (I) into a free compound and/or, if desired, separating a mixture of isomers of a compound of formula (I) into the single isomers.

Process-variants a) to l), respectively, can for instance be carried out at follows:

a) In a typical procedure the acid was added to a large excess of thionyl chloride (25 equivalents) kept under stirring at about 0° C. under nitrogen atmosphere, the mixture heated at about 60° C. for 1 hour, brought to room temperature and thoroughly evaporated in vacuo. The acid chloride II was dissolved in DMF and added to a mixture of the intermediate required (III) (1 equivalent) and triethylamine (1 equivalent) in DMF or pyridine. The mixture was stirred at room temperature for 48–72 hours, the solvent removed, the residue taken with brine and extracted with dichloromethane. The compounds thus obtained were purified by silica gel flash chromatography eluting with CH$_2$Cl$_2$/MeOH 9:1.

b) In a typical procedure compounds of formula IV were added to a solution of V in solvents like DMF, acetone, in presence of a base (NaH, K$_2$CO$_3$, KHMSA) the temperature varying between room temperature and reflux, the time of reaction varying between 24–72 hours. The mixture filtered the solvent evaporated and the residue taken with brine and extracted with dichloromethane or ethyl acetate. The compounds were purified by silica gel flash chromatography eluting with CH$_2$Cl$_2$/MeOH 9:1 or Petroleum ether 40–60/Ethyl acetate 1:1.

c) In a typical procedure the amino derivatives of formula VI reacted with the guanilating agent, such as di-Boc-triflylguanidine, in dichloromethane in presence of stechiometric amounts of base such as triethylamine or diusopropylethylamine, the time of reaction varying between 24–72 hours. The compounds thus obtained did not request further purification. (FEICHTINGER, K.; ZAPF, C.; SINGS, H. L.; GOODMAN, M.; J Org 1998, 63 (12), 3804–3805). The protection groups were removed according to standard procedures, with TFA.

d) In a typical procedure the amino derivatives of formula VI reacted with a cyanate salt, as e.g. a ammonium or sodium or potassium salt, in solvent such as AcOH, H₂O (Org. Synth. 1963, IV, 49) PNAS 1993, 90, 6909–6913) the temperature varying between 50–100° C., the time of reaction varying e) In a typical procedure the amino derivatives of formula VI reacted with isocyanates in presence of triethylamine refuxing in solvents such as dichloromethane, acetonitrile, toluene or dioxane (JMC 1996, 39 (22) 4382–4395; Eur J Med Chem 1997, 32 (10), 795–804.) to give the subtituted ureas, the temperature varying between room temperature and reflux, the time of reaction varying between 8–24 hours.

f) In a typical procedure to a stirred solution of the acids VIII (cinnamic or trans-3-(3-pyridyl)acrylic) as ethyl esters or polymer supported, in dichloromethane kept under vigorous stirring in nitrogen atmosphere, the amiothiophenols VII (2 eq) and DBU(0.1 equivalent) were added, the mixture was stirred at room temperature for about 24 hours, the solvent evaporated and the residue purified by silica gel flash chromatography eluting with petroleum ether 40–60/ethyl acetate 1:1, to give the intermediates required.

g) In a typical procedure compounds of formula X were added to a solution of IX in solvents like DMF, acetone, in presence of a base (K₂CO₃, NaH, KHMSA) the temperature varying between room temperature and reflux, time of reaction varying between 8–24 hours h) The ester compounds of formula I, were hydrolysed by treatment with a mixture of HCl 4N and ethanol overnight. Solvents were evaporated and the final compounds, obtained as hydrochlorides, purified by crystallisation with methanol and ether.

i) The sulfur functions of formula I were oxidised to solfones with 30% aq H₂O₂ (RAVIKUMAR, K. S.; BEGUE, J.-P.; BONNET-DELPON, D.; Tetrahedron Lett 1998, 39 (20), 3141–3144.) or with NaIO₄, in water and methanol, or acetone and water, according to a standard procedure (BEIER, C.; SCHAUMANN, E.; Synthesis 1997, (11), 1296–1300; LE MERRER, Y.; FUZIER, M.; DOSBAA, I.; FOGLIETTI, M.-J.; DEPEZAY, J.-C.; Tetrahedron 1997, 53 (49), 16731–16746.). The sulfur functions were oxidised to solfoxides according to a standard procedure by reacting with oxone in a mixture methanol/water as a solvent (HINTERBERGER, S.; HOFER, O.; GREGER, H.; Tetrahedron 1998, 54 (3), 487–496.)

l) Compounds of formula I linked to the Wang resin were cleaved as a final step with a mixture trifluoroacetic acid/dichloromethane, the time of reaction varying between 15–30 minutes.

Also the optional salification of a compound of formula (I) as well as the conversion of a salt into the free compound and the separation of a mixture of isomers into the single isomers may be carried our by conventional methods. For example, the separation of optical isomers may be carried out by salification with an optically active base or acid and by subsequent fractional crystallization of the diastereoisomeric salts, followed by recovering of the optically active isomeric-acids or, respectively, bases.

When in the compound of formula (I), and in the intermediate products thereof, groups are present which need to be protected before submitting them to the here-above illustrated reactions, they may be protected before the reactions take place and then deprotected, according to well known methods in organic chemistry.

The compounds of formulae (I) and the pharmaceutically acceptable salts thereof are herein defined as the "compounds of the present invention", the "compounds of the invention" and/or the "active principles of the pharmaceutical compositions of the invention".

For instance, according to process variant a) above, and according the indications herein provided, the compound 3-({4-[(3-{[amino(imino)methyl]amino}benzoyl)amino]-phenyl}sulfanyl)-3-(3-pyridinyl)propanoic acid (internal code PNU 277362F) can be provided. In particular compound PNU 277362F can be synthesized as bis-trifluoroacetate salt, as depicted in scheme 1, according to the procedures reported.

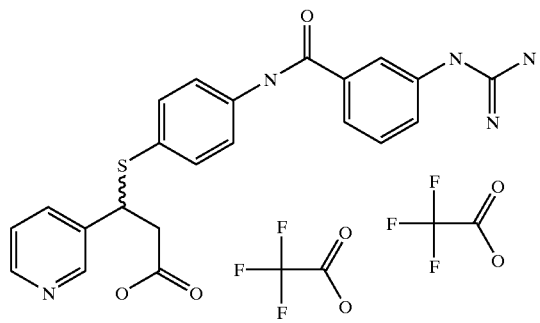

3-{4-[(3-{[amino(imino)methyl]amino}benzoyl)amino]phenyl}sulfanyl)}-3-(3-pyridinyl)propanoic acid bis-trifluoroacetate (PNU 277362F).

¹H-NMR (DMSO-d₆): 10.3 (s, 1H); 9.8 (s, 1H); 8.5 (m, 2H); 7.85 (m, 2H); 7.78 (m, 1H); 7.7 (d, 2H) 7.6–7.4 (m, 5H); 7.3 (d, 2H), 4.8 (t, 1H); 2.9 (m, 2H);

Elemental analysis:

Theoretic: C, 47.06%; H, 3.49%; F, 17.18%; N, 10.55%; S, 4.83%;

Found: C, 44.32%; H, 3.49%; F, 16.70%; N, 9.95%; S, 4.44%.

Scheme 1

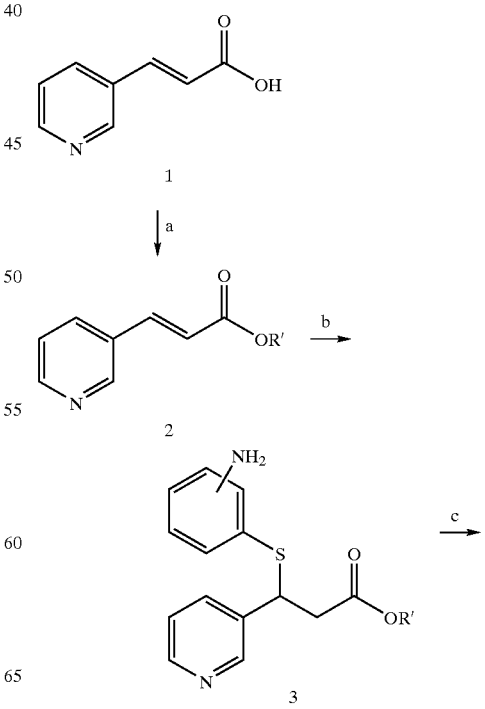

-continued

[Structure 4: Aryl carbamate with thioether linker to pyridyl propanoate ester, labeled "4"]

[Arrow labeled "d"]

[Structure 5: Corresponding carboxylic acid, labeled "5"]

if R' = Wang resin: (a) Pol—CH₂—OH, DIC, DMAP, CH2Cl2

(b) o-, m-, p-aminothiophenol, DBUcat, DMF, r.t.;
(c) ZCOCl, PYR or DMF, r.t.;
(d) EtOH/3N HCl, r.t. overnight or TFA/CH2Cl2, r.t.

Z is H₂N–C(=NH)–NH–(4-methylphenyl)

wherein
Pol=polymer of Wang resin; DIC=diisopropylcarbodiimide; DMAP=4-dimethylminopyridine; DBUcat=1,8-diazabicyclo[5,4,0]undec-7-ene in catalytic amount; DMF=dimethylformamide; TFA=trifluoro acetic acid.

Analogously, according to process variant d) above, the compound 3-{[4-({3-[(aminocarbonyl)amino]benzoyl}amino)phenyl]sulfanyl}-3-(3-pyridinyl) propanoic acid (internal code PNU 515440) is provided.

[Structure of PNU 515440]

3-{[4-({3-[(aminocarbonyl)amino]benzoyl}amino)phenyl]sulfanyl}-3-(3-pyridinyl) propanoic acid (PNU 515440)
MS: m/z 437 (M+H$^+$).
$^1$H-NMR (400 MHz), δ (DMSO-d$_6$): 2.82 (m, 2H, CH$_2$), 4.65 (m, 1H, CHS), 5.91 (s, 2H, CONH$_2$), 7.20–7.70 (m, 9H, ArH), 7.85 (m, 1H, ArH), 8.38 (m, 2H, pyridine hydrogens), 8.77 (s, 1H, NHCO), 10.24 (s, 1H, NHCO).

According to process variant e) above, the compound 3-{[4-({3-[(benzylamino)carbonyl])amino}benzoyl)amino]phenyl}sulfanyl)-3-(3-pyridinyl) propanoic acid (internal code PHA 515442E) is provided. The compound PNU 515442E can be synthesized as trifluoroacetate salts.

[Structure of PHA 515442E with CF$_3$COOH]

3-{[4-({3-[(benzylamino)carbonyl])amino}benzoyl)amino]phenyl}sulfanyl)-3-(3-pyridinyl) propanoic acid (PHA 515442E)
MS: m/z 527 (M+H$^+$).
$^1$H-NMR (400 MHz), δ (DMSO-d$_6$): 2.97 (m, 2H, CH$_2$), 4.29 (d, 2H, J=5.7, CH$_2$NH), 4.71 (m, 1H, CHS), 7.20–7.70 (m, 14H, ArH), 7.88 (m, 1H, ArH), 8.53 (m, 2H, pyridine hydrogens), 8.77 (s, 1H, NHCO), 10.27 (s, 1H, NHCO).

In analogy to process variants a) to l), the following compounds can be obtained:

3-({2-[(3-{[amino(imino)methyl]amino}benzoyl)amino]phenyl}sulfanyl)-3-(3-pyridinyl)propanoic acid;
3-({3-[(3-{[amino(imino)methyl]amino}benzoyl)amino]phenyl}sulfanyl)-3-(3-pyridinyl)propanoic acid;
3-({2-[(3-{[(benzylamino)(imino)methyl]amino}benzoyl)amino]phenyl}sulfanyl)-3-(3-pyridinyl)propanoic acid;
3-({3-[(3-{[(benzylamino)(imino)methyl]amino}benzoyl)amino]phenyl}sulfanyl)-3-(3-pyridinyl)propanoic acid;
3-{[2-({3-[(aminocarbonyl)amino]benzoyl}amino)phenyl]sulfanyl}-3-(3-pyridinyl)propanoic acid;
3-{[3-({3-[(aminocarbonyl)amino]benzoyl}amino)phenyl]sulfanyl}-3-(3-pyridinyl)propanoic acid;
3-({2-[(3-{[(benzylamino)carbonyl]amino}benzoyl)amino]phenyl}sulfanyl)-3-(3-pyridinyl)propanoic acid;
3-({3-[(3-{[(benzylamino)carbonyl]amino}benzoyl)amino]phenyl}sulfanyl)-3-(3-pyridinyl)propanoic acid;
3-({4-[(3-{[(benzylamino)carbonyl]amino}benzoyl)amino]phenyl}sulfanyl)-3-(3-pyridinyl)propanoic acid;
3-[(2-{[3-(4,5-dihydro-1H-imidazol-2-ylamino)benzoyl]amino}phenyl)sulfanyl]-3-(3-pyridinyl)propanoic acid;
3-[(3-{[3-(4,5-dihydro-1H-imidazol-2-ylamino)benzoyl]amino}phenyl)sulfanyl]-3-(3-pyridinyl)propanoic acid;
3-[(4-{[3-(4,5-dihydro-1H-imidazol-2-ylamino)benzoyl]amino}phenyl)sulfanyl]-3-(3-pyridinyl)propanoic acid;
3-[(2-{[3-(1H-imidazol-2-ylamino)benzoyl]amino}phenyl)sulfanyl]-3-(3-pyridinyl)propanoic acid;
3-[(3-{[3-(1H-imidazol-2-ylamino)benzoyl]amino}phenyl)sulfanyl]-3-(3-pyridinyl)propanoic acid;
3-[(4-{[3-(1H-imidazol-2-ylamino)benzoyl]amino}phenyl)sulfanyl]-3-(3-pyridinyl)propanoic acid;
3-(3-pyridinyl)-3-[(2-{[3-(2-pyridinylamino)benzoyl]amino}phenyl)sulfanyl]propanoic acid;
3-(3-pyridinyl)-3-[(3-{[3-(2-pyridinylamino)benzoyl]amino}phenyl)sulfanyl]propanoic acid;
3-(3-pyridinyl)-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-(3-pyridinyl)propanoic acid;
3-({3-[(4-{[amino(imino)methyl]amino}benzoyl)amino]phenyl}sulfanyl)-3-(3-pyridinyl)propanoic acid;

3-({4-[(4-{[amino(imino)methyl]amino}benzoyl)amino]phenyl}sulfanyl)-3-(3-pyridinyl)propanoic acid;
3-({2-[(4-{[(benzylamino)(imino)methyl]amino}benzoyl)amino]phenyl}sulfanyl)-3-(3-pyridinyl)propanoic acid;
3-({3-[(4-{[(benzylamino)(imino)methyl]amino}benzoyl)amino]phenyl}sulfanyl)-3-(3-pyridinyl)propanoic acid;
3-({4-[(4-{[(benzylamino)(imino)methyl]amino}benzoyl)amino]phenyl}sulfanyl)-3-(3-pyridinyl)propanoic acid;
3-{[2-({4-[(aminocarbonyl)amino]benzoyl}amino)phenyl]sulfanyl}-3-(3-pyridinyl)propanoic acid;
3-{[3-({4-[(aminocarbonyl)amino]benzoyl}amino)phenyl]sulfanyl}-3-(3-pyridinyl)propanoic acid;
3-{[4-({4-[(aminocarbonyl)amino]benzoyl}amino)phenyl]sulfanyl}-3-(3-pyridinyl)propanoic acid;
3-({2-[(4-{[(benzylamino)carbonyl]amino}benzoyl)amino]phenyl}sulfanyl)-3-(3-pyridinyl)propanoic acid;
3-({3-[(4-{[(benzylamino)carbonyl]amino}benzoyl)amino]phenyl}sulfanyl)-3-(3-pyridinyl)propanoic acid;
3-({4-[(4-{[(benzylamino)carbonyl]amino}benzoyl)amino]phenyl}sulfanyl)-3-(3-pyridinyl)propanoic acid;
3-[(2-{[4-(4,5-dihydro-1H-imidazol-2-ylamino)benzoyl]amino}phenyl)sulfanyl]-3-(3-pyridinyl)propanoic acid;
3-[(3-{[4-(4,5-dihydro-1H-imidazol-2-ylamino)benzoyl]amino}phenyl)sulfanyl]-3-(3-pyridinyl)propanoic acid;
3-[(4-{[4-(4,5-dihydro-1H-imidazol-2-ylamino)benzoyl]amino}phenyl)sulfanyl]-3-(3-pyridinyl)propanoic acid;
3-[(2-{[4-(1H-imidazol-2-ylamino)benzoyl]amino}phenyl)sulfanyl]-3-(3-pyridinyl)propanoic acid;
3-[(3-{[4-(1H-imidazol-2-ylamino)benzoyl]amino}phenyl)sulfanyl]-3-(3-pyridinyl)propanoic acid;
3-[(4-{[4-(1H-imidazol-2-ylamino)benzoyl]amino}phenyl)sulfanyl]-3-(3-pyridinyl)propanoic acid;
3-(3-pyridinyl)-3-[(2-{[4-(2-pyridinylamino)benzoyl]amino}phenyl)sulfanyl]propanoic acid;
3-(3-pyridinyl)-3-[(3-{[4-(2-pyridinylamino)benzoyl]amino}phenyl)sulfanyl]propanoic acid;
3-(3-pyridinyl)-3-[(4-{[4-(2-pyridinylamino)benzoyl]amino}phenyl)sulfanyl]propanoic acid;
3-({3-[(3-{[amino(imino)methyl]amino}benzoyl)amino]phenyl}sulfanyl)-3-phenylpropanoic acid;
3-({2-[(3-{[amino(imino)methyl]amino}benzoyl)amino]phenyl}sulfanyl)-3-phenylpropanoic acid;
3-({4-[(3-{[amino(imino)methyl]amino}benzoyl)amino]phenyl}sulfanyl)-3phenylpropanoic acid;
3-({2-[(3-{[(benzylamino)(imino)methyl]amino}benzoyl)amino]phenyl}sulfanyl)-3-phenylpropanoic acid;
3-({3-[(3-{[(benzylamino)(imino)methyl]amino}benzoyl)amino]phenyl}sulfanyl)-3-phenylpropanoic acid;
3-({4-[(3-{[(benzylamino)(imino)methyl]amino}benzoyl)amino]phenyl}sulfanyl)-3-phenylpropanoic acid;
3-{[2-({3-[(aminocarbonyl)amino]benzoyl}amino)phenyl]sulfanyl}-3-phenylpropanoic acid;
3-{[3-({3-[(aminocarbonyl)amino]benzoyl}amino)phenyl]sulfanyl}-3-phenylpropanoic acid;
3-{[4-({3-[(aminocarbonyl)amino]benzoyl}amino)phenyl]sulfanyl}-3-phenylpropanoic acid;
3-({2-[(3-{[(benzylamino)carbonyl]amino}benzoyl)amino]phenyl}sulfanyl)-3-phenylpropanoic acid;
3-({3-[(3-{[(benzylamino)carbonyl]amino}benzoyl)amino]phenyl}sulfanyl)-3-phenylpropanoic acid;
3-({4-[(3-{[(benzylamino)carbonyl]amino}benzoyl)amino]phenyl}sulfanyl)-3-phenylpropanoic acid;
3-[(2-{[3-(4,5-dihydro-1H-imidazol-2-ylamino)benzoyl]amino}phenyl)sulfanyl]-3-phenylpropanoic acid;
3-[(3-{[3-(4,5-dihydro-1H-imidazol-2-ylamino)benzoyl]amino}phenyl)sulfanyl]-3-phenylpropanoic acid;
3-[(4-{[3-(4,5-dihydro-1H-imidazol-2-ylamino)benzoyl]amino}phenyl)sulfanyl]-3-phenylpropanoic acid;
3-[(2-{[3-(1H-imidazol-2-ylamino)benzoyl]amino}phenyl)sulfanyl]-3-phenylpropanoic acid;
3-[(3-{[3-(1H-imidazol-2-ylamino)benzoyl]amino}phenyl)sulfanyl]-3-phenylpropanoic acid;
3-[(4-{[3-(1H-imidazol-2-ylamino)benzoyl]amino}phenyl)sulfanyl]-3-phenylpropanoic acid;
3-phenyl-3-[(2-{[3-(2-pyridinylamino)benzoyl]amino}phenyl)sulfanyl]propanoic acid;
3-phenyl-3-[(3-{[3-(2-pyridinylamino)benzoyl]amino}phenyl)sulfanyl]propanoic acid;
3-phenyl-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-phenylpropanoic acid;
3-({3-[(4-{[amino(imino)methyl]amino}benzoyl)amino]phenyl}sulfanyl)-3-phenylpropanoic acid;
3-({4-[(4-{[amino(imino)methyl]amino}benzoyl)amino]phenyl}sulfanyl)-3-phenylpropanoic acid;
3-({2-[(4-{[(benzylamino)(imino)methyl]amino}benzoyl)amino]phenyl}sulfanyl)-3-phenylpropanoic acid;
3-({3-[(4-{[(benzylamino)(imino)methyl]amino}benzoyl)amino]phenyl}sulfanyl)-3-phenylpropanoic acid;
3-({4-[(4-{[(benzylamino)(imino)methyl]amino}benzoyl)amino]phenyl}sulfanyl)-3-phenylpropanoic acid;
3-{[2-({4-[(aminocarbonyl)amino]benzoyl}amino)phenyl]sulfanyl}-3-phenylpropanoic acid;
3-{[3-({4-[(aminocarbonyl)amino]benzoyl}amino)phenyl]sulfanyl}-3-phenylpropanoic acid;
3-{[4-({4-[(aminocarbonyl)amino]benzoyl}amino)phenyl]sulfanyl}-3-phenylpropanoic acid;
3-({2-[(4-{[(benzylamino)carbonyl]amino}benzoyl)amino]phenyl}sulfanyl)-3-phenylpropanoic acid;
3-({3-[(4-{[(benzylamino)carbonyl]amino}benzoyl)amino]phenyl}sulfanyl)-3-phenylpropanoic acid;
3-({4-[(4-{[(benzylamino)carbonyl]amino}benzoyl)amino]phenyl}sulfanyl)-3-phenylpropanoic acid;
3-[(2-{[4-(4,5-dihydro-1H-imidazol-2-ylamino)benzoyl]amino}phenyl)sulfanyl]-3-phenylpropanoic acid;
3-[(3-{[4-(4,5-dihydro-1H-imidazol-2-ylamino)benzoyl]amino}phenyl)sulfanyl]-3-phenylpropanoic acid;
3-[(4-{[4-(4,5-dihydro-1H-imidazol-2-ylamino)benzoyl]amino}phenyl)sulfanyl]-3-phenylpropanoic acid;
3-[(2-{[4-(1H-imidazol-2-ylamino)benzoyl]amino}phenyl)sulfanyl]-3-phenylpropanoic acid;
3-[(3-{[4-(1H-imidazol-2-ylamino)benzoyl]amino}phenyl)sulfanyl]-3-phenylpropanoic acid;
3-[(4-{[4-(1H-imidazol-2-ylamino)benzoyl]amino}phenyl)sulfanyl]-3-phenylpropanoic acid;
3-phenyl-3-[(2-{[4-(2-pyridinylamino)benzoyl]amino}phenyl)sulfanyl]propanoic acid;
3-phenyl-3-[(3-{[4-(2-pyridinylamino)benzoyl]amino}phenyl)sulfanyl]propanoic acid;
3-phenyl-3-[(4-{[4-(2-pyridinylamino)benzoyl]amino}phenyl)sulfanyl]propanoic acid;
3-{2-[(4-{[amino(imino)methyl]amino}benzoyl)amino]phenoxy}-3-(3-pyridinyl)propanoic acid;
3-{3-[(4-{[amino(imino)methyl]amino}benzoyl)amino]phenoxy}-3-(3-pyridinyl)propanoic acid;
3-{4-[(4-{[amino(imino)methyl]amino}benzoyl)amino]phenoxy}-3-(3-pyridinyl)propanoic acid;
3-{2-[(4-{[(benzylamino)(imino)methyl]amino}benzoyl)amino]phenoxy}-3-(3-pyridinyl)propanoic acid;
3-{3-[(4-{[(benzylamino)(imino)methyl]amino}benzoyl)amino]phenoxy}-3-(3-pyridinyl)propanoic acid;
3-{4-[(4-{[(benzylamino)(imino)methyl]amino}benzoyl)amino]phenoxy}-3-(3-pyridinyl)propanoic acid;
3-[2-({4-[(aminocarbonyl)amino]benzoyl}amino)phenoxy]-3-(3-pyridinyl)propanoic acid;

3-[3-({4-[(aminocarbonyl)amino]benzoyl}amino)
phenoxy]-3-(3-pyridinyl)propanoic acid;
3-[4-({4-[(aminocarbonyl)amino]benzoyl}amino)
phenoxy]-3-(3-pyridinyl)propanoic acid;
3-{2-[(4-{[(benzylamino)carbonyl]amino}benzoyl)amino]
phenoxy}-3-(3-pyridinyl)propanoic acid;
3-{3-[(4-{[(benzylamino)carbonyl]amino}benzoyl)amino]
phenoxy}-3-(3-pyridinyl)propanoic acid;
3-{4-[(4-{[(benzylamino)carbonyl]amino}benzoyl)amino]
phenoxy}-3-(3-pyridinyl)propanoic acid;
3-(2-{[4-(4,5-dihydro-1H-imidazol-2-ylamino)benzoyl]
amino}phenoxy)-3-(3-pyridinyl)propanoic acid;
3-(3-{[4-(4,5-dihydro-1H-imidazol-2-ylamino)benzoyl]
amino}phenoxy)-3-(3-pyridinyl)propanoic acid;
3-(4-{[4-(4,5-dihydro-1H-imidazol-2-ylamino)benzoyl]
amino}phenoxy)-3-(3-pyridinyl)propanoic acid;
3-(2-{[4-(1H-imidazol-2-ylamino)benzoyl]
amino}phenoxy)-3-(3-pyridinyl)propanoic acid;
3-(3-{[4-(1H-imidazol-2-ylamino)benzoyl]
amino}phenoxy)-3-(3-pyridinyl)propanoic acid;
3-(4-{[4-(1H-imidazol-2-ylamino)benzoyl]
amino}phenoxy)-3-(3-pyridinyl)propanoic acid;
3-(3-pyridinyl)-3-(2-{[4-(2-pyridinylamino)benzoyl]
amino}phenoxy)propanoic acid;
3-(3-pyridinyl)-3-(3-{[4-(2-pyridinylamino)benzoyl]
amino}phenoxy)propanoic acid;
3-(3-pyridinyl)-3-(4-{[4-(2-pyridinylamino)benzoyl]
amino}phenoxy)propanoic acid;
3-{2-[(3-{[amino(imino)methyl]amino}benzoyl)amino]
phenoxy}-3-(3-pyridinyl)propanoic acid;
3-{3-[(3-{[amino(imino)methyl]amino}benzoyl)amino]
phenoxy}-3-(3-pyridinyl)propanoic acid;
3-{4-[(3-{[amino(imino)methyl]amino}benzoyl)amino]
phenoxy}-3-(3-pyridinyl)propanoic acid;
3-{2-[(3-{[(benzylamino)(imino)methyl]amino}benzoyl)
amino]phenoxy}-3-(3-pyridinyl)propanoic acid;
3-{3-[(3-{[(benzylamino)(imino)methyl]amino}benzoyl)
amino]phenoxy}-3-(3-pyridinyl)propanoic acid;
3-{4-[(3-{[(benzylamino)(imino)methyl]amino}benzoyl)
amino]phenoxy}-3-(3-pyridinyl)propanoic acid;
3-[2-({3-[(aminocarbonyl)amino]benzoyl}amino)
phenoxy]-3-(3-pyridinyl)propanoic acid;
3-[3-({3-[(aminocarbonyl)amino]benzoyl}amino)
phenoxy]-3-(3-pyridinyl)propanoic acid;
3-[4-({3-[(aminocarbonyl)amino]benzoyl}amino)
phenoxy]-3-(3-pyridinyl)propanoic acid;
3-{2-[(3-{[(benzylamino)carbonyl]amino}benzoyl)amino]
phenoxy}-3-(3-pyridinyl)propanoic acid;
3-{3-[(3-{[(benzylamino)carbonyl]amino}benzoyl)amino]
phenoxy}-3-(3-pyridinyl)propanoic acid;
3-{4-[(3-{[(benzylamino)carbonyl]amino}benzoyl)amino]
phenoxy}-3-(3-pyridinyl)propanoic acid;
3-(2-{[3-(4,5-dihydro-1H-imidazol-2-ylamino)benzoyl]
amino}phenoxy)-3-(3-pyridinyl)propanoic acid;
3-(3-{[3-(4,5-dihydro-1H-imidazol-2-ylamino)benzoyl]
amino}phenoxy)-3-(3-pyridinyl)propanoic acid;
3-(4-{[3-(4,5-dihydro-1H-imidazol-2-ylamino)benzoyl]
amino}phenoxy)-3-(3-pyridinyl)propanoic acid;
3-(2-{[3-(1H-imidazol-2-ylamino)benzoyl]
amino}phenoxy)-3-(3-pyridinyl)propanoic acid;
3-(3-{[3-(1H-imidazol-2-ylamino)benzoyl]
amino}phenoxy)-3-(3-pyridinyl)propanoic acid;
3-(4-{[3-(1H-imidazol-2-ylamino)benzoyl]
amino}phenoxy)-3-(3-pyridinyl)propanoic acid;
3-(3-pyridinyl)-3-(2-{[3-(2-pyridinylamino)benzoyl]
amino}phenoxy)propanoic acid;
3-(3-pyridinyl)-3-(3-{[3-(2-pyridinylamino)benzoyl]
amino}phenoxy)propanoic acid;
3-(3-pyridinyl)-3-(4-{[3-(2-pyridinylamino)benzoyl]
amino}phenoxy)propanoic acid;
3-{2-[(3-{[amino(imino)methyl]amino}benzoyl)amino]
phenoxy}-3-phenylpropanoic acid;
3-{3-[(3-{[amino(imino)methyl]amino}benzoyl)amino]
phenoxy}-3-phenylpropanoic acid;
3-{4-[(3-{[amino(imino)methyl]amino}benzoyl)amino]
phenoxy}-3-phenylpropanoic acid;
3-{2-[(3-{[(benzylamino)(imino)methyl]amino}benzoyl)
amino]phenoxy}-3-phenylpropanoic acid;
3-{3-[(3-{[(benzylamino)(imino)methyl]amino}benzoyl)
amino]phenoxy}-3-phenylpropanoic acid;
3-{4-[(3-{[(benzylamino)(imino)methyl]amino}benzoyl)
amino]phenoxy}-3-phenylpropanoic acid;
3-[2-({3-[(aminocarbonyl)amino]benzoyl}amino)
phenoxy]-3-phenylpropanoic acid;
3-[3-({3-[(aminocarbonyl)amino]benzoyl}amino)
phenoxy]-3-phenylpropanoic acid;
3-[4-({3-[(aminocarbonyl)amino]benzoyl}amino)
phenoxy]-3-phenylpropanoic acid;
3-{2-[(3-{[(benzylamino)carbonyl]amino}benzoyl)amino]
phenoxy}-3-phenylpropanoic acid;
3-{3-[(3-{[(benzylamino)carbonyl]amino}benzoyl)amino]
phenoxy}-3-phenylpropanoic acid;
3-{4-[(3-{[(benzylamino)carbonyl]amino}benzoyl)amino]
phenoxy}-3-phenylpropanoic acid;
3-(2-{[3-(4,5-dihydro-1H-imidazol-2-ylamino)benzoyl]
amino}phenoxy)-3-phenylpropanoic acid;
3-(3-{[3-(4,5-dihydro-1H-imidazol-2-ylamino)benzoyl]
amino}phenoxy)-3-phenylpropanoic acid;
3-(4-{[3-(4,5-dihydro-1H-imidazol-2-ylamino)benzoyl]
amino}phenoxy)-3-phenylpropanoic acid;
3-(2-{[3-(1H-imidazol-2-ylamino)benzoyl]
amino}phenoxy)-3-phenylpropanoic acid;
3-(3-{[3-(1H-imidazol-2-ylamino)benzoyl]
amino}phenoxy)-3-phenylpropanoic acid;
3-(4-{[3-(1H-imidazol-2-ylamino)benzoyl]
amino}phenoxy)-3-phenylpropanoic acid;
3-phenyl-3-(2-{[3-(2-pyridinylamino)benzoyl]
amino}phenoxy)propanoic acid;
3-phenyl-3-(3-{[3-(2-pyridinylamino)benzoyl]
amino}phenoxy)propanoic acid;
3-phenyl-3-(4-{[3-(2-pyridinylamino)benzoyl]
amino}phenoxy)propanoic acid;
3-{2-[(4-{[amino(imino)methyl]amino}benzoyl)amino]
phenoxy}-3-phenylpropanoic acid;
3-{3-[(4-{[amino(imino)methyl]amino}benzoyl)amino]
phenoxy}-3-phenylpropanoic acid;
3-{4-[(4-{[amino(imino)methyl]amino}benzoyl)amino]
phenoxy}-3-phenylpropanoic acid;
3-{2-[(4-{[(benzylamino)(imino)methyl]amino}benzoyl)
amino]phenoxy}-3-phenylpropanoic acid;
3-{3-[(4-{[(benzylamino)(imino)methyl]amino}benzoyl)
amino]phenoxy}-3-phenylpropanoic acid;
3-{4-[(4-{[(benzylamino)(imino)methyl]amino}benzoyl)
amino]phenoxy}-3-phenylpropanoic acid;
3-[2-({4-[(aminocarbonyl)amino]benzoyl}amino)
phenoxy]-3-phenylpropanoic acid;
3-[3-({4-[(aminocarbonyl)amino]benzoyl}amino)
phenoxy]-3-phenylpropanoic acid;
3-[4-({4-[(aminocarbonyl)amino]benzoyl}amino)
phenoxy]-3-phenylpropanoic acid;
3-{2-[(4-{[(benzylamino)carbonyl]amino}benzoyl)amino]
phenoxy}-3-phenylpropanoic acid;
3-{3-[(4-{[(benzylamino)carbonyl]amino}benzoyl)amino]
phenoxy}-3-phenylpropanoic acid;
3-{4-[(4-{[(benzylamino)carbonyl]amino}benzoyl)amino]
phenoxy}-3-phenylpropanoic acid;

3-(2-{[4-(4,5-dihydro-1H-imidazol-2-ylamino)benzoyl]
amino}phenoxy)-3-phenylpropanoic acid;
3-(3-{[4-(4,5-dihydro-1H-imidazol-2-ylamino)benzoyl]
amino}phenoxy)-3-phenylpropanoic acid;
3-(4-{[4-(4,5-dihydro-1H-imidazol-2-ylamino)benzoyl]
amino}phenoxy)-3-phenylpropanoic acid;
3-(2-{[4-(1H-imidazol-2-ylamino)benzoyl]
amino}phenoxy)-3-phenylpropanoic acid;
3-(3-{[4-(1H-imidazol-2-ylamino)benzoyl]
amino}phenoxy)-3-phenylpropanoic acid;
3-(4-{[4-(1H-imidazol-2-ylamino)benzoyl]
amino}phenoxy)-3-phenylpropanoic acid;
3-phenyl-3-(2-{[4-(2-pyridinylamino)benzoyl]
amino}phenoxy)propanoic acid;
3-phenyl-3-(3-{[4-(2-pyridinylamino)benzoyl]
amino}phenoxy)propanoic acid;
3-phenyl-3-(4-{[4-(2-pyridinylamino)benzoyl]
amino}phenoxy)propanoic acid;
3-({2-[(3-{[amino(imino)methyl]amino}benzoyl)amino]
phenyl}sulfinyl)-3-(3-pyridinyl)propanoic acid;
3-[({3-[(3-{[amino(imino)methyl]amino}benzoyl)amino]
phenyl}sulfinyl)-3-(3-pyridinyl)propanoic acid;
3-[({4-[(3-{[amino(imino)methyl]amino}benzoyl)amino]
phenyl}sulfinyl)-3-(3-pyridinyl)propanoic acid;
3-({2-[(3-{[(benzylamino)(imino)methyl]amino}benzoyl)
amino]phenyl}sulfinyl)-3-(3-pyridinyl)propanoic acid;
3-({3-[(3-{[(benzylamino)(imino)methyl]amino}benzoyl)
amino]phenyl}sulfinyl)-3-(3-pyridinyl)propanoic acid;
3-({4-[(3-{[(benzylamino)(imino)methyl]amino}benzoyl)
amino]phenyl}sulfinyl)-3-(3-pyridinyl)propanoic acid;
3-{[2-({3-[(aminocarbonyl)amino]benzoyl}amino)phenyl]
sulfinyl}-3-(3-pyridinyl)propanoic acid;
3-{[3-({3-[(aminocarbonyl)amino]benzoyl}amino)phenyl]
sulfinyl}-3-(3-pyridinyl)propanoic acid;
3-{[4-({3-[(aminocarbonyl)amino]benzoyl}amino)phenyl]
sulfinyl}-3-(3-pyridinyl)propanoic acid;
3-({2-[(3-{[(benzylamino)carbonyl]amino}benzoyl)amino]
phenyl}sulfinyl)-3-(3-pyridinyl)propanoic acid;
3-({3-[(3-{[(benzylamino)carbonyl]amino}benzoyl)amino]
phenyl}sulfinyl)-3-(3-pyridinyl)propanoic acid;
3-({4-[(3-{[(benzylamino)carbonyl]amino}benzoyl)amino]
phenyl}sulfinyl)-3-(3-pyridinyl)propanoic acid;
3-[(2-{[3-(4,5-dihydro-1H-imidazol-2-ylamino)benzoyl]
amino}phenyl)sulfinyl]-3-(3-pyridinyl)propanoic acid;
3-[(3-{[3-(4,5-dihydro-1H-imidazol-2-ylamino)benzoyl]
amino}phenyl)sulfinyl]-3-(3-pyridinyl)propanoic acid;
3-[(4-{[3-(4,5-dihydro-1H-imidazol-2-ylamino)benzoyl]
amino}phenyl)sulfinyl]-3-(3-pyridinyl)propanoic acid;
3-[(2-{[3-(1H-imidazol-2-ylamino)benzoyl]amino}phenyl)
sulfinyl]-3-(3-pyridinyl)propanoic acid;
3-[(3-{[3-(1H-imidazol-2-ylamino)benzoyl]amino}phenyl)
sulfinyl]-3-(3-pyridinyl)propanoic acid;
3-[(4-{[3-(1H-imidazol-2-ylamino)benzoyl]amino}phenyl)
sulfinyl]-3-(3-pyridinyl)propanoic acid;
3-(3-pyridinyl)-3-[(2-{[3-(2-pyridinylamino)benzoyl]
amino}phenyl)sulfinyl]propanoic acid;
3-(3-pyridinyl)-3-[(3-{[3-(2-pyridinylamino)benzoyl]
amino}phenyl)sulfinyl]propanoic acid;
3-(3-pyridinyl)-3-[(4-{[3-(2-pyridinylamino)benzoyl]
amino}phenyl)sulfinyl]propanoic acid;
3-({2-[(4-{[amino(imino)methyl]amino}benzoyl)amino]
phenyl}sulfinyl)-3-(3-pyridinyl)propanoic acid;
3-({3-[(4-{[amino(imino)methyl]amino}benzoyl)amino]
phenyl}sulfinyl)-3-(3-pyridinyl)propanoic acid;
3-({4-[(4-{[amino(imino)methyl]amino}benzoyl)amino]
phenyl}sulfinyl)-3-(3-pyridinyl)propanoic acid;
3-({2-[(4-{[(benzylamino)(imino)methyl]amino}benzoyl)
amino]phenyl}sulfinyl)-3-(3-pyridinyl)propanoic acid;

3-({3-[(4-{[(benzylamino)(imino)methyl]amino}benzoyl)
amino]phenyl}sulfinyl)-3-(3-pyridinyl)propanoic acid;
3-({4-[(4-{[(benzylamino)(imino)methyl]amino}benzoyl)
amino]phenyl}sulfinyl)-3-(3-pyridinyl)propanoic acid;
3-{[2-({4-[(aminocarbonyl)amino]benzoyl}amino)phenyl]
sulfinyl}-3-(3-pyridinyl)propanoic acid;
3-{[3-({4-[(aminocarbonyl)amino]benzoyl}amino)phenyl]
sulfinyl}-3-(3-pyridinyl)propanoic acid;
3-{[4-({4-[(aminocarbonyl)amino]benzoyl}amino)phenyl]
sulfinyl}-3-(3-pyridinyl)propanoic acid;
3-({2-[(4-{[(benzylamino)carbonyl]amino}benzoyl)amino]
phenyl}sulfinyl)-3-(3-pyridinyl)propanoic acid;
3-({3-[(4-{[(benzylamino)carbonyl]amino}benzoyl)amino]
phenyl}sulfinyl)-3-(3-pyridinyl)propanoic acid;
3-({4-[(4-{[(benzylamino)carbonyl]amino}benzoyl)amino]
phenyl}sulfinyl)-3-(3-pyridinyl)propanoic acid:
3-[(2-{[4-(4,5-dihydro-1H-imidazol-2-ylamino)benzoyl]
amino}phenyl)sulfinyl]-3-(3-pyridinyl)propanoic acid;
3-[(3-{[4-(4,5-dihydro-1H-imidazol-2-ylamino)benzoyl]
amino}phenyl)sulfinyl]-3-(3-pyridinyl)propanoic acid;
3-[(4-{[4-(4,5-dihydro-1H-imidazol-2-ylamino)benzoyl]
amino}phenyl)sulfinyl]-3-(3-pyridinyl)propanoic acid;
3-[(2-{[4-(1H-imidazol-2-ylamino)benzoyl]amino}phenyl)
sulfinyl]-3-(3-pyridinyl)propanoic acid;
3-(3-{[4-(1H-imidazol-2-ylamino)benzoyl]amino}phenyl)
sulfinyl]-3-(3-pyridinyl)propanoic acid;
3-[(4-{[4-(1H-imidazol-2-ylamino)benzoyl]amino}phenyl)
sulfinyl]-3-(3-pyridinyl)propanoic acid;
3-(3-pyridinyl)-3-[(2-{[4-(2-pyridinylamino)benzoyl]
amino}phenyl)sulfinyl]propanoic acid;
3-(3-pyridinyl)-3-[(3-{[4-(2-pyridinylamino)benzoyl]
amino}phenyl)sulfinyl]propanoic acid;
3-(3-pyridinyl)-3-[(4-{[4-(2-pyridinylamino)benzoyl]
amino}phenyl)sulfinyl]propanoic acid;
3-({2-[(3-{[amino(imino)methyl]amino}benzoyl)amino]
phenyl}sulfonyl)-3-(3-pyridinyl)propanoic acid;
3-({3-[(3-{[amino(imino)methyl]amino}benzoyl)amino]
phenyl}sulfonyl)-3-(3-pyridinyl)propanoic acid;
3-({4-[(3-{[amino(imino)methyl]amino}benzoyl)amino]
phenyl}sulfonyl)-3-(3-pyridinyl)propanoic acid;
3-({2-[(3-{[(benzylamino)(imino)methyl]amino}benzoyl)
amino]phenyl}sulfonyl)-3-(3-pyridinyl)propanoic acid;
3-({3-[(3-{[(benzylamino)(imino)methyl]amino}benzoyl)
amino]phenyl}sulfonyl)-3-(3-pyridinyl)propanoic acid;
3-({4-[(3-{[(benzylamino)(imino)methyl]amino}benzoyl)
amino]phenyl}sulfonyl)-3-(3-pyridinyl)propanoic acid;
3-{[2-({3-[(aminocarbonyl)amino]benzoyl}amino)phenyl]
sulfonyl}-3-(3-pyridinyl)propanoic acid;
3-{[3-({3-[(aminocarbonyl)amino]benzoyl}amino)phenyl]
sulfonyl}-3-(3-pyridinyl)propanoic acid;
3-{[4-({3-[(aminocarbonyl)amino]benzoyl}amino)phenyl]
sulfonyl}-3-(3-pyridinyl)propanoic acid;
3-({2-[(3-{[(benzylamino)carbonyl]amino}benzoyl)amino]
phenyl}sulfonyl)-3-(3-pyridinyl)propanoic acid;
3-({3-[(3-{[(benzylamino)carbonyl]amino}benzoyl)amino]
phenyl}sulfonyl)-3-(3-pyridinyl)propanoic acid;
3-({4-[(3-{[(benzylamino)carbonyl]amino}benzoyl)amino]
phenyl}sulfonyl)-3-(3-pyridinyl)propanoic acid;
3-[(2-{[3-(4,5-dihydro-1H-imidazol-2-ylamino)benzoyl]
amino}phenyl)sulfonyl]-3-(3-pyridinyl)propanoic acid;
3-[(3-{[3-(4,5-dihydro-1H-imidazol-2-ylamino)benzoyl]
amino}phenyl)sulfonyl]-3-(3-pyridinyl)propanoic acid;
3-[(4-{[3-(4,5-dihydro-1H-imidazol-2-ylamino)benzoyl]
amino}phenyl)sulfonyl]-3-(3-pyridinyl)propanoic acid;
3-[(2-{[3-(1H-imidazol-2-ylamino)benzoyl]amino}phenyl)
sulfonyl]-3-(3-pyridinyl)propanoic acid;
3-[(3-{[3-(1H-imidazol-2-ylamino)benzoyl]amino}phenyl)
sulfonyl]-3-(3-pyridinyl)propanoic acid;

3-[(4-{[3-(1H-imidazol-2-ylamino)benzoyl]amino}phenyl)sulfonyl]-3-(3-pyridinyl)propanoic acid;
3-(3-pyridinyl)-3-[(2-{[3-(2-pyridinylamino)benzoyl]amino}phenyl)sulfonyl]propanoic acid;
3-(3-pyridinyl)-3-[(3-{[3-(2-pyridinylamino)benzoyl]amino}phenyl)sulfonyl]propanoic acid;
3-(3-pyridinyl)-3-[(4-{[3-(2-pyridinylamino)benzoyl]amino}phenyl)sulfonyl]propanoic acid;
3-({2-[(4-{[amino(imino)methyl]amino}benzoyl)amino]phenyl}sulfonyl)-3-(3-pyridinyl)propanoic acid;
3-({3-[(4-{[amino(imino)methyl]amino}benzoyl)amino]phenyl}sulfonyl)-3-(3-pyridinyl)propanoic acid;
3-({4-[(4-{[amino(imino)methyl]amino}benzoyl)amino]phenyl}sulfonyl)-3-(3-pyridinyl)propanoic acid;
3-({2-[(4-{[(benzylamino)(imino)methyl]amino}benzoyl)amino]phenyl}sulfonyl)-3-(3-pyridinyl)propanoic acid;
3-({3-[(4-{[(benzylamino)(imino)methyl]amino}benzoyl)amino]phenyl}sulfonyl)-3-(3-pyridinyl)propanoic acid;
3-({4-[(4-{[(benzylamino)(imino)methyl]amino}benzoyl)amino]phenyl}sulfonyl)-3-(3-pyridinyl)propanoic acid;
3-{[2-({4-[(aminocarbonyl)amino]benzoyl}amino)phenyl]sulfonyl}-3-(3-pyridinyl)propanoic acid;
3-{[3-({4-[(aminocarbonyl)amino]benzoyl}amino)phenyl]sulfonyl}-3-(3-pyridinyl)propanoic acid;
3-{[4-({4-[(aminocarbonyl)amino]benzoyl}amino)phenyl]sulfonyl}-3-(3-pyridinyl)propanoic acid;
3-({2-[(4-{[(benzylamino)carbonyl]amino}benzoyl)amino]phenyl}sulfonyl)-3-(3-pyridinyl)propanoic acid;
3-({3-[(4-{[(benzylamino)carbonyl]amino}benzoyl)amino]phenyl}sulfonyl)-3-(3-pyridinyl)propanoic acid;
3-({4-[(4-{[(benzylamino)carbonyl]amino}benzoyl)amino]phenyl}sulfonyl)-3-(3-pyridinyl)propanoic acid;
3-[(2-{[4-(4,5-dihydro-1H-imidazol-2-ylamino)benzoyl]amino}phenyl)sulfonyl]-3-(3-pyridinyl)propanoic acid;
3-[(3-{[4-(4,5-dihydro-1H-imidazol-2-ylamino)benzoyl]amino}phenyl)sulfonyl]-3-(3-pyridinyl)propanoic acid;
3-[(4-{[4-(4,5-dihydro-1H-imidazol-2-ylamino)benzoyl]amino}phenyl)sulfonyl]-3-(3-pyridinyl)propanoic acid;
3-[(2-{[4-(1H-imidazol-2-ylamino)benzoyl]amino}phenyl)sulfonyl]-3-(3-pyridinyl)propanoic acid;
3-[(3-{[4-(1H-imidazol-2-ylamino)benzoyl]amino}phenyl)sulfonyl]-3-(3-pyridinyl)propanoic acid;
3-[(4-{[4-(1H-imidazol-2-ylamino)benzoyl]amino}phenyl)sulfonyl]-3-(3-pyridinyl)propanoic acid;
3-(3-pyridinyl)-3-[(2-{[4-(2-pyridinylamino)benzoyl]amino}phenyl)sulfonyl]propanoic acid;
3-(3-pyridinyl)-3-[(3-{[4-(2-pyridinylamino)benzoyl]amino}phenyl)sulfonyl]propanoic acid;
3-(3-pyridinyl)-3-[(4-{[4-(2-pyridinylamino)benzoyl]amino}phenyl)sulfonyl]propanoic acid;
3-({3-[(3-{[amino(imino)methyl]amino}benzoyl)amino]phenyl}sulfinyl)-3-phenylpropanoic acid;
3-({2-[(3-{[amino(imino)methyl]amino}benzoyl)amino]phenyl}sulfinyl)-3-phenylpropanoic acid;
3-({4-[(3-{[amino(imino)methyl]amino}benzoyl)amino]phenyl}sulfinyl)-3phenylpropanoic acid;
3-({2-[(3-{[(benzylamino)(imino)methyl]amino}benzoyl)amino]phenyl}sulfinyl)-3-phenylpropanoic acid;
3-({3-[(3-{[(benzylamino)(imino)methyl]amino}benzoyl)amino]phenyl}sulfinyl)-3-phenylpropanoic acid;
3-({4-[(3-{[(benzylamino)(imino)methyl]amino}benzoyl)amino]phenyl}sulfinyl)-3-phenylpropanoic acid;
3-{[2-({3-[(aminocarbonyl)amino]benzoyl}amino)phenyl]sulfinyl}-3-phenylpropanoic acid;
3-{[3-({3-[(aminocarbonyl)amino]benzoyl}amino)phenyl]sulfinyl}-3-phenylpropanoic acid;
3-{[4-({3-[(aminocarbonyl)amino]benzoyl}amino)phenyl]sulfinyl}-3-phenylpropanoic acid;
3-({2-[(3-{[(benzylamino)carbonyl]amino}benzoyl)amino]phenyl}sulfinyl)-3-phenylpropanoic acid;
3-({3-[(3-{[(benzylamino)carbonyl]amino}benzoyl)amino]phenyl}sulfinyl)-3-phenylpropanoic acid;
3-({4-[(3-{[(benzylamino)carbonyl]amino}benzoyl)amino]phenyl}sulfinyl)-3-phenylpropanoic acid;
3-[(2-{[3-(4,5-dihydro-1H-imidazol-2-ylamino)benzoyl]amino}phenyl)sulfinyl]-3-phenylpropanoic acid;
3-[(3-{[3-(4,5-dihydro-1H-imidazol-2-ylamino)benzoyl]amino}phenyl)sulfinyl]-3-phenylpropanoic acid;
3-[(4-{[3-(4,5-dihydro-1H-imidazol-2-ylamino)benzoyl]amino}phenyl)sulfinyl]-3-phenylpropanoic acid;
3-[(2-{[3-(1H-imidazol-2-ylamino)benzoyl]amino}phenyl)sulfinyl]-3-phenylpropanoic acid;
3-[(3-{[3-(1H-imidazol-2-ylamino)benzoyl]amino}phenyl)sulfinyl]-3-phenylpropanoic acid;
3-[(4-{[3-(1H-imidazol-2-ylamino)benzoyl]amino}phenyl)sulfinyl]-3-phenylpropanoic acid;
3-phenyl-3-[(2-{[3-(2-pyridinylamino)benzoyl]amino}phenyl)sulfinyl]propanoic acid;
3-phenyl-3-[(3-{[3-(2-pyridinylamino)benzoyl]amino}phenyl)sulfinyl]propanoic acid;
3-phenyl-3-[(4-{[3-(2-pyridinylamino)benzoyl]amino}phenyl)sulfinyl]propanoic acid;
3-({2-[(4-{[amino(imino)methyl]amino}benzoyl)amino]phenyl}sulfinyl)-3-phenylpropanoic acid;
3-({3-[(4-{[amino(imino)methyl]amino}benzoyl)amino]phenyl}sulfinyl)-3-phenylpropanoic acid;
3-({4-[(4-{[amino(imino)methyl]amino}benzoyl)amino]phenyl}sulfinyl)-3-phenylpropanoic acid;
3-({2-[(4-{[(benzylamino)(imino)methyl]amino}benzoyl)amino]phenyl}sulfinyl)-3-phenylpropanoic acid;
3-({3-[(4-{[(benzylamino)(imino)methyl]amino}benzoyl)amino]phenyl}sulfinyl)-3-phenylpropanoic acid;
3-({4-[(4-{[(benzylamino)(imino)methyl]amino}benzoyl)amino]phenyl}sulfinyl)-3-phenylpropanoic acid;
3-{[2-({4-[(aminocarbonyl)amino]benzoyl}amino)phenyl]sulfinyl}-3-phenylpropanoic acid;
3-{[3-({4-[(aminocarbonyl)amino]benzoyl}amino)phenyl]sulfinyl}-3-phenylpropanoic acid;
3-{[4-({4-[(aminocarbonyl)amino]benzoyl}amino)phenyl]sulfinyl}-3-phenylpropanoic acid;
3-({2-[(4-{[(benzylamino)carbonyl]amino}benzoyl)amino]phenyl}sulfinyl)-3-phenylpropanoic acid;
3-({3-[(4-{[(benzylamino)carbonyl]amino}benzoyl)amino]phenyl}sulfinyl)-3-phenylpropanoic acid;
3-({4-[(4-{[(benzylamino)carbonyl]amino}benzoyl)amino]phenyl}sulfinyl)-3-phenylpropanoic acid;
3-[(2-{[4-(4,5-dihydro-1H-imidazol-2-ylamino)benzoyl]amino}phenyl)sulfinyl]-3-phenylpropanoic acid;
3-[(3-{[4-(4,5-dihydro-1H-imidazol-2-ylamino)benzoyl]amino}phenyl)sulfinyl]-3-phenylpropanoic acid;
3-[(4-{[4-(4,5-dihydro-1H-imidazol-2-ylamino)benzoyl]amino}phenyl)sulfinyl]-3-phenylpropanoic acid;
3-[(2-{[4-(1H-imidazol-2-ylamino)benzoyl]amino}phenyl)sulfinyl]-3-phenylpropanoic acid;
3-[(3-{[4-(1H-imidazol-2-ylamino)benzoyl]amino}phenyl)sulfinyl]-3-phenylpropanoic acid;
3-[(4-{[4-(1H-imidazol-2-ylamino)benzoyl]amino}phenyl)sulfinyl]-3-phenylpropanoic acid;
3-phenyl-3-[(2-{[4-(2-pyridinylamino)benzoyl]amino}phenyl)sulfinyl]propanoic acid;
3-phenyl-3-[(3-{[4-(2-pyridinylamino)benzoyl]amino}phenyl)sulfinyl]propanoic acid;
3-phenyl-3-[(4-{[4-(2-pyridinylamino)benzoyl]amino}phenyl)sulfinyl]propanoic acid;
3-({3-[(3-{[amino(imino)methyl]amino}benzoyl)amino]phenyl}sulfonyl)-3-phenylpropanoic acid;

3-({2-[(3-{[amino(imino)methyl]amino}benzoyl)amino]phenyl}sulfonyl)-3-phenylpropanoic acid;
3-({4-[(3-{[amino(imino)methyl]amino}benzoyl)amino]phenyl}sulfonyl)-3-phenylpropanoic acid;
3-({2-[(3-{[(benzylamino)(imino)methyl]amino}benzoyl)amino]phenyl}sulfonyl)-3-phenylpropanoic acid;
3-({3-[(3-{[(benzylamino)(imino)methyl]amino}benzoyl)amino]phenyl}sulfonyl)-3-phenylpropanoic acid;
3-({4-[(3-{[(benzylamino)(imino)methyl]amino}benzoyl)amino]phenyl}sulfonyl)-3-phenylpropanoic acid;
3-{[2-({3-[(aminocarbonyl)amino]benzoyl}amino)phenyl]sulfonyl}-3-phenylpropanoic acid;
3-{[3-({3-[(aminocarbonyl)amino]benzoyl}amino)phenyl]sulfonyl}-3-phenylpropanoic acid;
3-{[4-({3-[(aminocarbonyl)amino]benzoyl}amino)phenyl]sulfonyl}-3-phenylpropanoic acid;
3-({2-[(3-{[(benzylamino)carbonyl]amino}benzoyl)amino]phenyl}sulfonyl)-3-phenylpropanoic acid;
3-({3-[(3-{[(benzylamino)carbonyl]amino}benzoyl)amino]phenyl}sulfonyl)-3-phenylpropanoic acid;
3-({4-[(3-{[(benzylamino)carbonyl]amino}benzoyl)amino]phenyl}sulfonyl)-3-phenylpropanoic acid;
3-[(2-{[3-(4,5-dihydro-1H-imidazol-2-ylamino)benzoyl]amino}phenyl)sulfonyl]-3-phenylpropanoic acid;
3-[(3-{[3-(4,5-dihydro-1H-imidazol-2-ylamino)benzoyl]amino}phenyl)sulfonyl]-3-phenylpropanoic acid;
3-[(4-{[3-(4,5-dihydro-1H-imidazol-2-ylamino)benzoyl]amino}phenyl)sulfonyl]-3-phenylpropanoic acid;
3-[(2-{[3-(1H-imidazol-2-ylamino)benzoyl]amino}phenyl)sulfonyl]-3-phenylpropanoic acid;
3-[(3-{[3-(1H-imidazol-2-ylamino)benzoyl]amino}phenyl)sulfonyl]-3-phenylpropanoic acid;
3-[(4-{[3-(1H-imidazol-2-ylamino)benzoyl]amino}phenyl)sulfonyl]-3-phenylpropanoic acid;
3-phenyl-3-[(2-{[3-(2-pyridinylamino)benzoyl]amino}phenyl)sulfonyl]propanoic acid;
3-phenyl-3-[(3-{[3-(2-pyridinylamino)benzoyl]amino}phenyl)sulfonyl]propanoic acid;
3-phenyl-3-[(4-{[3-(2-pyridinylamino)benzoyl]amino}phenyl)sulfonyl]propanoic acid;
3-({2-[(4-{[amino(imino)methyl]amino}benzoyl)amino]phenyl}sulfonyl)-3-phenylpropanoic acid;
3-({3-[(4-{[amino(imino)methyl]amino}benzoyl)amino]phenyl}sulfonyl)-3-phenylpropanoic acid;
3-({4-[(4-{[amino(imino)methyl]amino}benzoyl)amino]phenyl}sulfonyl)-3-phenylpropanoic acid;
3-({2-[(4-{[(benzylamino)(imino)methyl]amino}benzoyl)amino]phenyl}sulfonyl)-3-phenylpropanoic acid;
3-({3-[(4-{[(benzylamino)(imino)methyl]amino}benzoyl)amino]phenyl}sulfonyl)-3-phenylpropanoic acid;
3-({4-[(4-{[(benzylamino)(imino)methyl]amino}benzoyl)amino]phenyl}sulfonyl)-3-phenylpropanoic acid;
3-{[2-({4-[(aminocarbonyl)amino]benzoyl}amino)phenyl]sulfonyl}-3-phenylpropanoic acid;
3-{[3-({4-[(aminocarbonyl)amino]benzoyl}amino)phenyl]sulfonyl}-3-phenylpropanoic acid;
3-{[4-({4-[(aminocarbonyl)amino]benzoyl}amino)phenyl]sulfonyl}-3-phenylpropanoic acid;
3-({2-[(4-{[(benzylamino)carbonyl]amino}benzoyl)amino]phenyl}sulfonyl)-3-phenylpropanoic acid;
3-({3-[(4-{[(benzylamino)carbonyl]amino}benzoyl)amino]phenyl}sulfonyl)-3-phenylpropanoic acid;
3-({4-[(4-{[(benzylamino)carbonyl]amino}benzoyl)amino]phenyl}sulfonyl)-3-phenylpropanoic acid;
3-[(2-{[4-(4,5-dihydro-1H-imidazol-2-ylamino)benzoyl]amino}phenyl)sulfonyl]-3-phenylpropanoic acid;
3-[(3-{[4-(4,5-dihydro-1H-imidazol-2-ylamino)benzoyl]amino}phenyl)sulfonyl]-3-phenylpropanoic acid;
3-[(4-{[4-(4,5-dihydro-1H-imidazol-2-ylamino)benzoyl]amino}phenyl)sulfonyl]-3-phenylpropanoic acid;
3-[(2-{[4-(1H-imidazol-2-ylamino)benzoyl]amino}phenyl)sulfonyl]-3-phenylpropanoic acid;
3-[(3-{[4-(1H-imidazol-2-ylamino)benzoyl]amino}phenyl)sulfonyl]-3-phenylpropanoic acid;
3-[(4-{[4-(1H-imidazol-2-ylamino)benzoyl]amino}phenyl)sulfonyl]-3-phenylpropanoic acid;
3-phenyl-3-[(2-{[4-(2-pyridinylamino)benzoyl]amino}phenyl)sulfonyl]propanoic acid;
3-phenyl-3-[(3-{[4-(2-pyridinylamino)benzoyl]amino}phenyl)sulfonyl]propanoic acid;
3-phenyl-3-[(4-{[4-(2-pyridinylamino)benzoyl]amino}phenyl)sulfonyl]propanoic acid;
3-phenyl-3-[(2-{[4-(2-pyridinylamino)benzoyl]amino}phenyl)sulfonyl]propanoic acid;
3-phenyl-3-[(3-{[4-(2-pyridinylamino)benzoyl]amino}phenyl)sulfonyl]propanoic acid;
3-phenyl-3-[(4-{[4-(2-pyridinylamino)benzoyl]amino}phenyl)sulfonyl]propanoic acid;
3-(3-pyridinyl)-3-(2-{[3-(1,4,5,6-tetrahydro-2-pyrimidinylamino)benzoyl]amino}phenoxy)propanoic acid;
3-(3-pyridinyl)-3-(3-{[3-(1,4,5,6-tetrahydro-2-pyrimidinylamino)benzoyl]amino}phenoxy)propanoic acid;
3-(3-pyridinyl)-3-(4-{[3-(1,4,5,6-tetrahydro-2-pyrimidinylamino)benzoyl]amino}phenoxy)propanoic acid;
3-(3-pyridinyl)-3-(2-{[4-(1,4,5,6-tetrahydro-2-pyrimidinylamino)benzoyl]amino}phenoxy)propanoic acid;
3-(3-pyridinyl)-3-(3-{[4-(1,4,5,6-tetrahydro-2-pyrimidinylamino)benzoyl]amino}phenoxy)propanoic acid;
3-(3-pyridinyl)-3-(4-{[4-(1,4,5,6-tetrahydro-2-pyrimidinylamino)benzoyl]amino}phenoxy)propanoic acid;
3-phenyl-3-(2-{[3-(1,4,5,6-tetrahydro-2-pyrimidinylamino)benzoyl]amino}phenoxy)propanoic acid;
3-phenyl-3-(3-{[3-(1,4,5,6-tetrahydro-2-pyrimidinylamino)benzoyl]amino}phenoxy)propanoic acid;
3-phenyl-3-(4-{[3-(1,4,5,6-tetrahydro-2-pyrimidinylamino)benzoyl]amino}phenoxy)propanoic acid;
3-phenyl-3-(2-{[4-(1,4,5,6-tetrahydro-2-pyrimidinylamino)benzoyl]amino}phenoxy)propanoic acid;
3-phenyl-3-(3-{[4-(1,4,5,6-tetrahydro-2-pyrimidinylamino)benzoyl]amino}phenoxy)propanoic acid;
3-phenyl-3-(4-{[4-(1,4,5,6-tetrahydro-2-pyrimidinylamino)benzoyl]amino}phenoxy)propanoic acid;
3-(3-pyridinyl)-3-[(2-{[3-(1,4,5,6-tetrahydro-2-pyrimidinylamino)benzoyl]amino}phenyl)sulfanyl]propanoic acid;
3-(3-pyridinyl)-3-[(3-{[3-(1,4,5,6-tetrahydro-2-pyrimidinylamino)benzoyl]amino}phenyl)sulfanyl]propanoic acid;
3-(3-pyridinyl)-3-[(4-{[3-(1,4,5,6-tetrahydro-2-pyrimidinylamino)benzoyl]amino}phenyl)sulfanyl]propanoic acid;
3-(3-pyridinyl)-3-[(2-{[4-(1,4,5,6-tetrahydro-2-pyrimidinylamino)benzoyl]amino}phenyl)sulfanyl]propanoic acid;
3-(3-pyridinyl)-3-[(3-{[4-(1,4,5,6-tetrahydro-2-pyrimidinylamino)benzoyl]amino}phenyl)sulfanyl]propanoic acid;
3-(3-pyridinyl)-3-[(4-{[4-(1,4,5,6-tetrahydro-2-pyrimidinylamino)benzoyl]amino}phenyl)sulfanyl]propanoic acid;

3-phenyl-3-[(2-{[3-(1,4,5,6-tetrahydro-2-pyrimidinylamino)benzoyl]amino}phenyl)sulfanyl]propanoic acid;
3-phenyl-3-[(3-{[3-(1,4,5,6-tetrahydro-2-pyrimidinylamino)benzoyl]amino}phenyl)sulfanyl]propanoic acid;
3-phenyl-3-[(4-{[3-(1,4,5,6-tetrahydro-2-pyrimidinylamino)benzoyl]amino}phenyl)sulfanyl]propanoic acid;
3-phenyl-3-[(2-{[4-(1,4,5,6-tetrahydro-2-pyrimidinylamino)benzoyl]amino}phenyl)sulfanyl]propanoic acid;
3-phenyl-3-[(3-{[4-(1,4,5,6-tetrahydro-2-pyrimidinylamino)benzoyl]amino}phenyl)sulfanyl]propanoic acid;
3-phenyl-3-[(4-{[4-(1,4,5,6-tetrahydro-2-pyrimidinylamino)benzoyl]amino}phenyl)sulfanyl]propanoic acid;
3-(3-pyridinyl)-3-[(2-{[3-(1,4,5,6-tetrahydro-2-pyrimidinylamino)benzoyl]amino}phenyl)sulfinyl]propanoic acid;
3-(3-pyridinyl)-3-[(3-{[3-(1,4,5,6-tetrahydro-2-pyrimidinylamino)benzoyl]amino}phenyl)sulfinyl]propanoic acid;
3-(3-pyridinyl)-3-[(4-{[3-(1,4,5,6-tetrahydro-2-pyrimidinylamino)benzoyl]amino}phenyl)sulfinyl]propanoic acid;
3-(3-pyridinyl)-3-[(2-{[4-(1,4,5,6-tetrahydro-2-pyrimidinylamino)benzoyl]amino}phenyl)sulfinyl]propanoic acid;
3-(3-pyridinyl)-3-[(3-{[4-(1,4,5,6-tetrahydro-2-pyrimidinylamino)benzoyl]amino}phenyl)sulfinyl]propanoic acid;
3-(3-pyridinyl)-3-[(4-{[4-(1,4,5,6-tetrahydro-2-pyrimidinylamino)benzoyl]amino}phenyl)sulfinyl]propanoic acid;
3-phenyl-3-[(2-{[3-(1,4,5,6-tetrahydro-2-pyrimidinylamino)benzoyl]amino}phenyl)sulfinyl]propanoic acid;
3-phenyl-3-[(3-{[3-(1,4,5,6-tetrahydro-2-pyrimidinylamino)benzoyl]amino}phenyl)sulfinyl]propanoic acid;
3-phenyl-3-[(4-{[3-(1,4,5,6-tetrahydro-2-pyrimidinylamino)benzoyl]amino}phenyl)sulfinyl]propanoic acid;
3-phenyl-3-[(2-{[4-(1,4,5,6-tetrahydro-2-pyrimidinylamino)benzoyl]amino}phenyl)sulfinyl]propanoic acid;
3-phenyl-3-[(3-{[4-(1,4,5,6-tetrahydro-2-pyrimidinylamino)benzoyl]amino}phenyl)sulfinyl]propanoic acid;
3-phenyl-3-[(4-{[4-(1,4,5,6-tetrahydro-2-pyrimidinylamino)benzoyl]amino}phenyl)sulfinyl]propanoic acid;
3-(3-pyridinyl)-3-[(2-{[3-(1,4,5,6-tetrahydro-2-pyrimidinylamino)benzoyl]amino}phenyl)sulfonyl]propanoic acid;
3-(3-pyridinyl)-3-[(3-{[3-(1,4,5,6-tetrahydro-2-pyrimidinylamino)benzoyl]amino}phenyl)sulfonyl]propanoic acid;
3-(3-pyridinyl)-3-[(4-{[3-(1,4,5,6-tetrahydro-2-pyrimidinylamino)benzoyl]amino}phenyl)sulfonyl]propanoic acid;
3-(3-pyridinyl)-3-[(2-{[4-(1,4,5,6-tetrahydro-2-pyrimidinylamino)benzoyl]amino}phenyl)sulfonyl]propanoic acid;
3-(3-pyridinyl)-3-[(3-{[4-(1,4,5,6-tetrahydro-2-pyrimidinylamino)benzoyl]amino}phenyl)sulfonyl]propanoic acid;
3-(3-pyridinyl)-3-[(4-{[4-(1,4,5,6-tetrahydro-2-pyrimidinylamino)benzoyl]amino}phenyl)sulfonyl]propanoic acid;
3-phenyl-3-[(2-{[3-(1,4,5,6-tetrahydro-2-pyrimidinylamino)benzoyl]amino}phenyl)sulfonyl]propanoic acid;
3-phenyl-3-[(3-{[3-(1,4,5,6-tetrahydro-2-pyrimidinylamino)benzoyl]amino}phenyl)sulfonyl]propanoic acid;
3-phenyl-3-[(4-{[3-(1,4,5,6-tetrahydro-2-pyrimidinylamino)benzoyl]amino}phenyl)sulfonyl]propanoic acid;
3-phenyl-3-[(2-{[4-(1,4,5,6-tetrahydro-2-pyrimidinylamino)benzoyl]amino}phenyl)sulfonyl]propanoic acid;
3-phenyl-3-[(3-{[4-(1,4,5,6-tetrahydro-2-pyrimidinylamino)benzoyl]amino}phenyl)sulfonyl]propanoic acid;
3-phenyl-3-[(4-{[4-(1,4,5,6-tetrahydro-2-pyrimidinylamino)benzoyl]amino}phenyl)sulfonyl]propanoic acid;
either as a free acid or a salt thereof, in particular the hydrochloride or the trifluoroacetate.

Pharmacology

The compounds of the invention are selective integrin receptor inhibitors or antagonists, in particular of the αvβ3 integrin receptors. The specific inhibiting or antagonist activity of the compounds of the invention is shown for instance by the fact that they are active in in vitro solid phase αvβ3-vitronectin binding assay, as described below.

αvβ3-vitronectin Binding Assay

A solid phase assay for the study of αvβ3-vitronectin binding was set up on the basis of already published methods (Wong et al, Molecular Pharmacology 50: 529–537, 1996; Brooks et al., Cell 85: 683–693, 1996). The human αvβ3 integrin was diluted into coating buffer (CB) containing 150 mM NaCl, 1 mM $CaCl_2$, 1 mM $MgCl_2$, 1 mM $MnCl_2$, 20 mM TRIS, pH 7.4 at a concentration of 1.5 μg/ml. Into 96-well plates, 50 μl of the diluted integrin were added and allowed to bind to the plate walls overnight at 4° C. Next day, the assay plates were emptied and 100 μl of blocking buffer (CB buffer with 3% BSA) were added to each well for 45 min at 37° C. After the incubation, the plates were washed three times with 100 μl assay buffer (AB, CB buffer with 0.1% BSA); serial 1:1 dilution (25 μl/well) of the test compounds were added to the plates, starting from 10 mM solutions in 100% DMSO diluted to 100 μM in AB. The binding reaction was started by addition (25 μl/well) of 10 nM biotinylated vitronectin (final concentration: 5 nM), and lasted 30 min at 37° C. The concentration range of the tested compounds spanned from 50 to 0.0005 μM. At the end of the co-incubation, the assay plates were washed as before and 70 μl of a 1:1000 AB dilution of peroxydase-conjugated streptavidin were added per well and were allowed to react for 45 min at 37° C. Then, the plates were washed as described and 50 μl of ready to use Turbo-TMB substrate for peroxydase were added to each well. After 30 minutes incubation at room temperature, the color development was stopped with 50 μl sulphuric acid 0.38 M and the plates were read at a wavelength of 450 nm with a Packard plate reader. The values obtained were analyzed by four parameters curve fit in the computer program GraphPad Prism, after normalization by a maximum binding control (Bmax) detected in wells where no competitor was added, and a minimum binding control (NSB) detected in wells where no integrin was coated. Under standard assay conditions, $A_{450}$ was never under 1.0 for Bmax, and around 0.15 for NSB. The computerized algorithm gave the concentration of compound needed to inhibit the maximum binding by 50% ($IC_{50}$ value): for those compounds that did not inhibit this binding by 50% at the highest concentration tested, $IC_{50}$ value was reported as being greater then the highest concentration tested. As a positive control, increasing doses of a peptide containing the RGD sequence was added to each plate: $IC_{50}$ value of this molecule was 120 nM.

Materials

Human vitronectin receptor (αvβ3) was purified from human placenta (Pytela et al, Methods in Enzymology, 144: 475–489, 1987). Turbo-TMB was from PIERCE (34022). BSA (A4503), Vitronectin (V8379), RGD peptide (G4144) and all generic reagents were from SIGMA. Vitronectin was biotinylated according to the procedure indicated in the NHS biotinylation kit from PIERCE (21420). Horseradish peroxydase-streptavidin was from Amersham (RPN1231). 96-well plates were from Costar (#3690, EIA/RIA plate, 1/2 area flat bottom, high binding).

αIIbβ3-fibrinogen Binding Assay

A solid phase assay for the study of αIIbβ3-fibrinogen binding was set up on according to the method described for αvβ3. αIIbβ3 integrin was diluted into coating buffer (CB) containing 150 mM NaCl, 1 mM $CaCl_2$, 1 mM $MgCl_2$, 1 mM $MnCl_2$, 20 mM TRIS, pH 7.4 at a concentration of 3 μg/ml. Into 96-well plates, 50 μl of the diluted integrin were added and allowed to bind to the plate walls overnight at 4° C. Next day, the assay plates were emptied and 100 μl of blocking buffer (CB buffer with 3% BSA) were added to each well for 45 min at 37° C. After the incubation, the plates were washed three times with 100 μl assay buffer (AB, CB buffer with 0.1% BSA); serial 1:1 dilution (25 μl/well) of the test compounds were added to the plates, starting from 10 mM solutions in 100% DMSO diluted to 100 μM in AB. The binding reaction was started by addition (25 μl/well) of 20 nM biotinylated fibrinogen (final concentration: 10 nM), and lasted 30 min at 37° C. The concentration range of the tested compounds spanned from 50 to 0.0005 μM. At the end of the co-incubation, the assay plates were washed as before and 70 μl of a 1:1000 AB dilution of peroxydase-conjugated streptavidin were added per well and were allowed to react for 45 min at 37° C. Then, the plates were washed as described and 50 μl of ready to use Turbo-TMB substrate for peroxydase were added to each well. After 30 minutes incubation at room temperature, the color development was stopped with 50 μl sulphuric acid 0.38 M and the plates were read at a wavelength of 450 nm with a Packard plate reader. The values obtained were analyzed by four parameters curve fit with the computer program Graph-Pad Prism, after normalization by a maximum binding control (Bmax) detected in wells where no competitor was added, and a minimum binding control (NSB) detected in wells where no integrin was coated. Under standard assay conditions, $A_{450}$ was never under 0.8 for Bmax, and around 0.15 for NSB. The computerized algorithm gave the concentration of compound needed to inhibit the maximum binding by 50% ($IC_{50}$ value): for those compounds that did not inhibit this binding by 50% at the highest concentration tested, $IC_{50}$ value was reported as being greater then the highest concentration tested. As a positive control, increasing doses of a peptide containing the RGD sequence was added to each plate: $IC_{50}$ value of this molecule was 2.3 μM for αIIbβ3-fibrinogen binding.

Materials

Human fibrinogen receptor (αIIbβ3) was purified from human platelets ((Pytela et al, Methods in Enzymology, 144: 475–489, 1987). Turbo-TMB was from PIERCE (34022). BSA (A4503), fibrinogen (F4883), RGD peptide (G4144) and all generic reagents were from SIGMA. Fibrinogen was biotinylated according to the procedure indicated in the NHS biotinylation kit from PIERCE (21420). Horseradish peroxydase-streptavidin was from Amersham (RPN1231). 96-well plates were from Costar (#3690, EIA/RIA plate, 1/2 area flat bottom, high binding).

Cell Based Assay

Cell Line

Adhesion assay to vitronectin is performed using CEM (human leukemia cell line) stably transfected with cDNAs encoding human $α_v$ and $β_3$ integrin subunits. The CEM D9 clone, expressing high levels of $α_vβ_3$ integrin as confirmed by western blotting, was selected for the assay. The binding of CEM D9 to vitronectin is completely inhibited by anti-$α_vβ_3$ monoclonal antibody LM609.

Coating Plate

Vitronectin (Sigma) is diluted to 10 μl/ml in DPBS (Dulbecco's phosphate buffered saline), dispensed 50 μl/well in 96 well high binding RIA/EIA plates (Costar) and allowed to coat overnight at 4° C. For blank 50 μl/well of heat denatured 3% BSA solution (bovine serum albumin), is dispensed. Plates are washed once with DBPS and saturated with 200 μl/well of 3% BSA, for 2 h at 37° C. At the end of incubation, each well is washed once with DBPS.

Adhesion Assay

For the assay, cells in log phase of growth are used. The cellular suspension is centrifuged at 1500 rpm for 8 min., washed with 10 ml of HBSS, resuspended in fresh complete medium and activated with 1 ng/ml PMA (Phorbol Miristate Acetate) for 1 h at 37° C. After incubation, cells are washed, counted, and diluted to a density of $1.6 \times 10^6$ cells/ml in adhesion medium (0.1% heat denaturated BSA in HBSS+1 mM $MnCl_2$).

10 μl of adhesion medium containing inhibitors at suitable concentrations are added to test wells. 90 μl/well of cell suspension is plated and incubated for 1 h at 37° C. Following adhesion, plates are gently washed twice with 200 μl of DPBSS and cells are fixed with 50 μl TCA 50% (tricloroacetic acid) for 1 hour at 4° C. Evaluation of cell adhesion is performed by staining with sulforhodamine B (1).

Parameters of Evaluation

The percentage of relative adhesion (RA %) is calculated using the following formula:

$$\% = \frac{\text{average of O.D. (570 nm) of treated cells} - \text{average of O.D. of blank}}{\text{average of O.D. (570 nm) of control cells} - \text{average of O.D. of blank}} \times 100$$

Where O.D. is the optical density of wells at 570 nm, using a EL 340 plate reader. $IC_{50}$ is the dose inhibiting 50% of cell adhesion.

For example, compound 3-({4-[(3-{[amino(imino)methyl]amino}benzoyl)amino]-phenyl}sulfanyl)-3-(3-pyridinyl)propanoic acid (company code PNU 277362F), when tested in αvβ3-vitronectin and αIIbβ3-fibrinogen biding assays, gave the following activity data:

αvβ3($IC_{50}$ μmol)=0.016±0.009
αIIbβ3($IC_{50}$ μmol)=9.8±4.8

These test data show that compound 3-({4-[(3-{[amino(imino)methyl]amino}-benzoyl)amino]-phenyl}sulfanyl)-3-(3-pyridinyl)propanoic acid is endowed with high selective αvβ3 inhibiting activity. In fact, the ratio between αIIbβ3 and αvβ3 inhibiting activity is about 600.

In view of their high selective αvβ3 inhibiting or antagonizing activity, the compounds of the invention can be used in medicine in treating conditions mediated by the αvβ3 integrin. Accordingly, the compounds of the invention are useful for instance for treating various conditions or disease states including osteoporosis, humoral hypercalcemia of malignancy, Paget's disease, tumor metastasis, solid tumor growth (neoplasia), angiogenesis including tumor angiogenesis, retinopathy including diabetic retinopathy, arthritis including rheumatoid arthritis, psoriasis, periodontal disease, smooth muscle cell migration and restenosis in a mammal in need of such treatment. Additionally, such pharmaceutical agents are useful as antiviral agents, and antimicrobials.

According to a preferred object of the invention the αvβ3 inhibiting activity results in an anticancer therapy having increased effectiveness in controlling, i.e., slowing, interrupting, arresting, stopping or reversing, the neoplasm formation.

The compounds of the invention can be administered in a variety of dosage forms, e.g. suspensions; rectally, in the form of suppositories; parenterally, e.g. intramuscularly, or by intravenous injection of infusion; or topically.

The dosage regimen for the compounds and/or compositions containing the compounds is based on a variety of factors, including the type, age, weight, sex and medical condition of the patent; the severity of the condition; the route of administration; and the activity of the particular compound employed. Thus the dosage regime may vary widely. Dosage levels of the order from about 0.01 mg to about 1000 mg per kilogram of body weight per day are useful in the treatment of the above-indicated conditions and more preferably of the order from about 0.01 mg to about 100 mg/kg of body weight. For instance, the dosage adopted for oral administration to adult humans for compound PNU 277362F may range from about 0.01 mg to about 800 mg/kg of body weight per day and more preferably of the order from about 0.01 mg to about 750 mg/kg body weight.

When given parenterally a suitable daily dose for instance for compound PNU 277362F would typically be about 0.01 to 100 mg/kg body weight injected per day in multiple doses depending on the factors listed above and more preferably from about 0.01 mg to about 10 mg/kg body weight.

The invention includes pharmaceutical compositions comprising a compound of formula (I) or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions or pastes, can be prepared by admixing the active ingredient with a conventional oleaginous or emulsifying excipient.

The following formulation examples illustrate but do not limit the invention.

EXAMPLE 1

Capsules, each dosed at 0.200 g and containing 20 mg of the active substance can be prepared.

Composition for 500 capsules:

| | |
|---|---|
| 3-{4-[(3-{[amino(imino)methyl]amino}benzoyl)amino]phenyl}sulfanyl)}-3-(3-pyridinyl)propanoic acid (PNU 277362F) | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 2

Tablets, each weighing 0.150 g and containing 25 mg of the active substance, can be manufactured as follows.

Composition for 10,000 tablets:

| | |
|---|---|
| 3-{4-[(3-{[amino(imino)methyl]amino}benzoyl)amino]phenyl}sulfanyl)}-3-(3-pyridinyl)propanoic acid | 250 g |
| Lactose | 800 g |
| Corn starch | 415 g |
| Talc powder | 30 g |
| Magnesium stearate | 5 g |

The 3-{4-[(3-{[amino(imino)methyl]amino}benzoyl)amino]phenyl}sulfanyl)}-3-(3-pyridinyl)propanoic acid, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 3

Intravenous Infusion 1–10 mg/ml.

An intravenous infusion pharmaceutical preparation can be manufactured by dissolving 50 mg of 3-{4-[(3-{[amino(imino)methyl]amino}benzoyl)amino]phenyl}-sulfanyl)}-3-(3-pyridinyl)propanoic acid in water for injection (1000 ml) and sealing glass ampoules of 1–10 ml.

Prior to infusion, the obtained solution can be diluted according to the common practice, and stored and/or delivered in glass, polypropylene, polyolefin or polyethylene-lined equipment.

A further object of the present invention is a combined method of treatment of cancer or of controlling the growth of the neoplasm in mammals, including humans, suffering from cancer, said method comprising administering 1) a compound of the invention, or a pharmaceutically acceptable salt thereof, and
2) an additional antitumor agent, in amounts and close enough together in time sufficient to produce a therapeutically useful effect.

The present invention also provides a product containing a compound of the invention, or a pharmaceutically acceptable salt thereof, and an effective antineoplastic amount of additional antitumor agent as a combined preparation for simultaneous, separate or sequential use in anti-cancer therapy.

Object of the present invention is to provide the use of a compound of formula (I), as herein defined, or a pharmaceutically acceptable salt thereof, in the preparation of a medicament having $\alpha v \beta 3$ integrin inhibiting or antagonizing activity for controlling the growth of the neoplasm in a method additionally comprising the administration of an antitumor agent.

The combination preparation according to the invention can also include combination packs or compositions in which the constituents are placed side by side and can therefore be administered simultaneously, separately or sequentially to one and the same human being. Accordingly, the antineoplastic agent and a compound according to the present invention may be present within a single or distinct container means.

In the combined preparations, pharmaceutical compositions and methods of treating, according to the present invention, the antineoplastic agent may comprise 1 to 4, preferably 1, 2 or 3, antineoplastic drugs, in particular a single antineoplastic drug.

As used herein, "controlling the growth" of the neoplasm refers to slowing, interrupting, arresting or stopping its growth and it does not necessarily indicate a total elimination of the neoplasm. It is believed that prolonging the survivability of a patient, beyond being a significant advantageous effect in and of itself, also indicates that the condition is beneficially controlled to some extent.

The term "antineoplastic agent" is meant to comprise both a single antineoplastic cytotoxic drug and "cocktails", i.e. mixtures of such drugs, according to the clinical practice.

As used herein, the term "effective antineoplastic amount" refers to an amount which is effective, upon single or multiple dose administration to the patient, in controlling the growth of the neoplasm or in prolonging the survivability of the patient beyond that expected in the absence of such treatment.

An antineoplastic agent, according to the invention, is preferably selected from the group comprising: an antineoplastic topoisomerase II inhibitor, an antineoplastic antimicrotubule agent, an antineoplastic alkylating agent, an antineoplastic antimetabolite and an antineoplastic topoisomerase I inhibitor.

An antineoplastic topoisomerase II inhibitor is preferably:
a) an anthracycline compound e.g. doxorubicin (including liposomal formulations) daunomycin, methoxy-morpholino-doxorubicin, epirubicin (including liposomal formulation), idarubicin and nemorubicin; and
b) an anthraquinone compound e.g. mitoxantrone and losoxantrone; and
c) a podophillotoxine compound e.g. etoposide and teniposide.

An antimicrotubule agent is preferably:
a) a taxane compound e.g. paclitaxel (including liposomal formulations) and docetaxel; and
b) a vinca alkaloid e.g. vinblastine and vinorelbine.

An alkylating agent is preferably cyclophosphamide, ifosfamide, chlorambucil, melphalan and PNU 159548 (C. Geroni et al., Proc. Am. Assoc. Cancer Res 39, p 223, 1998 (Abstr. #1517).

An antineoplastic antimetabolite agent is e.g. 5-fluorouracil, capecitabine, gemcitabine, methotrexate and edatrexate.

An antineoplastic topoisomerase I inhibitor is e.g. topotecan, irinotecan, 9-nitrocamptothecin and PNU 166148 (Compound A1 in WO 99/17804).

An antineoplastic agent is in particular epirubicin, doxorubicin, liposome-encapsulated doxorubicin, docetaxel, paclitaxel and liposome-encapsulated paclitaxel.

Particularly preferred preparations, pharmaceutical compositions and methods of treating, according to the present invention, are those comprising a) 1, 2 or 3 antineoplastic agents selected from epirubicin, doxorubicin, idarubicin, paclitaxel, docetaxel, 5-fluorouracil, cyclophosphamide and vinorelbine, and b) a compound of the invention or a pharmaceutically acceptable salt thereof.

The effective antineoplastic amounts of the various antineoplastic agents are well known and appreciated in the art.

For example, an effective antineoplastic amount of vinblastine may vary from about 3 mg/m$^2$ to about 10 mg/m$^2$.

An effective antineoplastic amount of doxorubicin may vary from about 20 mg/m$^2$ to about 100 mg/m$^2$.

An effective antineoplastic amount of epirubicin may vary from about 20 mg/m$^2$ to about 200 mg/m$^2$.

An effective antineoplastic amount of idarubicin may vary from about 1 mg/m$^2$ to about 50 mg/m$^2$.

An effective antineoplastic amount of mitoxantrone may vary from about 10 mg/m$^2$ to about 20 mg/m$^2$.

An effective antineoplastic amount of paclitaxel may vary from about 100 mg/m$^2$ to about 300 mg/m$^2$.

An effective antineoplastic amount of docetaxel may vary from about 50 mg/m$^2$ to about 100 mg/m$^2$.

An effective antineoplastic amount of vinorelbine may vary from about 15 mg/m$^2$ to about 30 mg/m$^2$.

An effective antineoplastic amount of cyclophosphamide may vary from about 100 mg/m$^2$ to about 1500 mg/m$^2$.

An effective antineoplastic amount of melphalan may vary from about 1 gm/m$^2$ to about 10 mg/m$^2$.

An effective antineoplastic amount of 5-fluorouracil may vary from about 100 mg/m$^2$ to about 1000 mg/m$^2$.

An effective antineoplastic amount of capecitabine may vary from about 10 mg/m$^2$ to about 1000 mg/m$^2$.

An effective antineoplastic amount of methotrexate may vary from about 10 mg/m$^2$ to about 1000 mg/m$^2$.

An effective antineoplastic amount of topotecan may vary from about 1 gm/m$^2$ to about 5 mg/m$^2$.

An effective antineoplastic amount of irinotecan may vary from about 50 mg/m$^2$ to about 350 mg/m$^2$.

In effecting treatment of a patient afflicted with a disease state described above a compound of formula (I) of the invention can be administered in any form or mode which makes the compound bioavailable in effective amounts, including oral and parenteral routes. For example, it can be administered orally, subcutaneously, intraperitoneally, intramuscularly, intravenously, transdermally, and the like. Oral or intramuscular administration is generally preferred. One skilled in the art of preparing formulations can readily select the proper form and mode of administration depending upon the particular circumstances, including the disease state to be treated, the stage of the disease, the form of administration of the selected cytotoxic agent and the manner of co-administration selected.

The selected antineoplastic agent can be administered by the appropriate route and dosing schedule as is well known and accepted for the particular agent. For example, epirubicin, doxorubicin, idarubicin, paclitaxel, docetaxel, 5-fluorouracil, cyclophosphamide and vinblastine can be administered intravenously. Idarubicin and cyclophosphamide can also be given orally.

In the combined preparations, pharmaceutical compositions, method of treating and therapeutic uses, according to the present invention, speficic preferred compounds of the invention are the following:

3-({2-[(3-{[amino(imino)methyl]amino}benzoyl)amino]phenyl}sulfanyl)-3-(3-pyridinyl)propanoic acid;
3-({3-[(3-{[amino(imino)methyl]amino}benzoyl)amino]phenyl}sulfanyl)-3-(3-pyridinyl)propanoic acid;
3-({4-[(3-{[amino(imino)methyl]amino}benzoyl)amino]phenyl}sulfanyl)-3-(3-pyridinyl)propanoic acid;
3-({2-[(3-{[(benzylamino)(imino)methyl]amino}benzoyl)amino]phenyl}sulfanyl)-3-(3-(3-pyridinyl)propanoic acid;
3-({3-[(3-{[(benzylamino)(imino)methyl]amino}benzoyl)amino]phenyl}sulfanyl)-3-(3-(3-pyridinyl)propanoic acid;
3-({4-[(3-{[(benzylamino)(imino)methyl]amino}benzoyl)amino]phenyl}sulfanyl)-3-(3-(3-pyridinyl)propanoic acid;
3-{[2-({3-[(aminocarbonyl)amino]benzoyl}amino)phenyl]sulfanyl}-3-(3-pyridinyl)propanoic acid;
3-{[3-({3-[(aminocarbonyl)amino]benzoyl}amino)phenyl]sulfanyl}-3-(3-pyridinyl)propanoic acid;
3-{[4-({3-[(aminocarbonyl)amino]benzoyl}amino)phenyl]sulfanyl}-3-(3-pyridinyl)propanoic acid;
3-({2-[(3-{[(benzylamino)carbonyl]amino}benzoyl)amino]phenyl}sulfanyl)-3-(3-pyridinyl)propanoic acid;
3-({3-[(3-{[(benzylamino)carbonyl]amino}benzoyl)amino]phenyl}sulfanyl)-3-(3-pyridinyl)propanoic acid;
3-({4-[(3-{[(benzylamino)carbonyl]amino}benzoyl)amino]phenyl}sulfanyl)-3-(3-pyridinyl)propanoic acid;
3-[(2-{[3-(4,5-dihydro-1H-imidazol-2-ylamino)benzoyl]amino}phenyl)sulfanyl]-3-(3-pyridinyl)propanoic acid;
3-[(3-{[3-(4,5-dihydro-1H-imidazol-2-ylamino)benzoyl]amino}phenyl)sulfanyl]-3-(3-pyridinyl)propanoic acid;
3-[(4-{[3-(4,5-dihydro-1H-imidazol-2-ylamino)benzoyl]amino}phenyl)sulfanyl]-3-(3-pyridinyl)propanoic acid;
3-[(2-{[3-(1H-imidazol-2-ylamino)benzoyl]amino}phenyl)sulfanyl]-3-(3-pyridinyl)propanoic acid;
3-[(3-{[3-(1H-imidazol-2-ylamino)benzoyl]amino}phenyl)sulfanyl]-3-(3-pyridinyl)propanoic acid;
3-[(4-{[3-(1H-imidazol-2-ylamino)benzoyl]amino}phenyl)sulfanyl]-3-(3-pyridinyl)propanoic acid;
3-(3-pyridinyl)-3-[(2-{[3-(2-pyridinylamino)benzoyl]amino}phenyl)sulfanyl]propanoic acid;
3-(3-pyridinyl)-3-[(3-{[3-(2-pyridinylamino)benzoyl]amino}phenyl)sulfanyl]propanoic acid;
3-(3-pyridinyl)-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-(3-pyridinyl)propanoic acid;
3-({3-[(4-{[amino(imino)methyl]amino}benzoyl)amino]phenyl}sulfanyl)-3-(3-pyridinyl)propanoic acid;
3-({4-[(4-{[amino(imino)methyl]amino}benzoyl)amino]phenyl}sulfanyl)-3-(3-pyridinyl)propanoic acid;
3-({2-[(4-{[(benzylamino)(imino)methyl]amino}benzoyl)amino]phenyl}sulfanyl)-3-(3-pyridinyl)propanoic acid;
3-({3-[(4-{[(benzylamino)(imino)methyl]amino}benzoyl)amino]phenyl}sulfanyl)-3-(3-pyridinyl)propanoic acid;
3-({4-[(4-{[(benzylamino)(imino)methyl]amino}benzoyl)amino]phenyl}sulfanyl)-3-(3-pyridinyl)propanoic acid;
3-{[2-({4-[(aminocarbonyl)amino]benzoyl}amino)phenyl]sulfanyl}-3-(3-pyridinyl)propanoic acid;
3-{[3-({4-[(aminocarbonyl)amino]benzoyl}amino)phenyl]sulfanyl}-3-(3-pyridinyl)propanoic acid;
3-{[4-({4-[(aminocarbonyl)amino]benzoyl}amino)phenyl]sulfanyl}-3-(3-pyridinyl)propanoic acid;
3-({2-[(4-{[(benzylamino)carbonyl]amino}benzoyl)amino]phenyl}sulfanyl)-3-(3-pyridinyl)propanoic acid;
3-({3-[(4-{[(benzylamino)carbonyl]amino}benzoyl)amino]phenyl}sulfanyl)-3-(3-pyridinyl)propanoic acid;
3-({4-[(4-{[(benzylamino)carbonyl]amino}benzoyl)amino]phenyl}sulfanyl)-3-(3-pyridinyl)propanoic acid;
3-[(2-{[4-(4,5-dihydro-1H-imidazol-2-ylamino)benzoyl]amino}phenyl)sulfanyl]-3-(3-pyridinyl)propanoic acid;
3-[(3-{[4-(4,5-dihydro-1H-imidazol-2-ylamino)benzoyl]amino}phenyl)sulfanyl]-3-(3-pyridinyl)propanoic acid;
3-[(4-{[4-(4,5-dihydro-1H-imidazol-2-ylamino)benzoyl]amino}phenyl)sulfanyl]-3-(3-pyridinyl)propanoic acid;
3-[(2-{[4-(1H-imidazol-2-ylamino)benzoyl]amino}phenyl)sulfanyl]-3-(3-pyridinyl)propanoic acid;
3-[(3-{[4-(1H-imidazol-2-ylamino)benzoyl]amino}phenyl)sulfanyl]-3-(3-pyridinyl)propanoic acid;
3-[(4-{[4-(1H-imidazol-2-ylamino)benzoyl]amino}phenyl)sulfanyl]-3-(3-pyridinyl)propanoic acid;
3-(3-pyridinyl)-3-[(2-{[4-(2-pyridinylamino)benzoyl]amino}phenyl)sulfanyl]propanoic acid;
3-(3-pyridinyl)-3-[(3-{[4-(2-pyridinylamino)benzoyl]amino}phenyl)sulfanyl]propanoic acid;
3-(3-pyridinyl)-3-[(4-{[4-(2-pyridinylamino)benzoyl]amino}phenyl)sulfanyl]propanoic acid;
3-({3-[(3-{[amino(imino)methyl]amino}benzoyl)amino]phenyl}sulfanyl)-3-phenylpropanoic acid;
3-({2-[(3-{[amino(imino)methyl]amino}benzoyl)amino]phenyl}sulfanyl)-3-phenylpropanoic acid;
3-({4-[(3-{[amino(imino)methyl]amino}benzoyl)amino]phenyl}sulfanyl)-3-phenylpropanoic acid;
3-({2-[(3-{[(benzylamino)(imino)methyl]amino}benzoyl)amino]phenyl}sulfanyl)-3-phenylpropanoic acid;
3-({3-[(3-{[(benzylamino)(imino)methyl]amino}benzoyl)amino]phenyl}sulfanyl)-3-phenylpropanoic acid;
3-({4-[(3-{[(benzylamino)(imino)methyl]amino}benzoyl)amino]phenyl}sulfanyl)-3-phenylpropanoic acid;
3-{[2-({3-[(aminocarbonyl)amino]benzoyl}amino)phenyl]sulfanyl}-3-phenylpropanoic acid;
3-{[3-({3-[(aminocarbonyl)amino]benzoyl}amino)phenyl]sulfanyl}-3-phenylpropanoic acid;
3-{[4-({3-[(aminocarbonyl)amino]benzoyl}amino)phenyl]sulfanyl}-3-phenylpropanoic acid;
3-({2-[(3-{[(benzylamino)carbonyl]amino}benzoyl)amino]phenyl}sulfanyl)-3-phenylpropanoic acid;
3-({3-[(3-{[(benzylamino)carbonyl]amino}benzoyl)amino]phenyl}sulfanyl)-3-phenylpropanoic acid;
3-({4-[(3-{[(benzylamino)carbonyl]amino}benzoyl)amino]phenyl}sulfanyl)-3-phenylpropanoic acid;

3-[(2-{[3-(4,5-dihydro-1H-imidazol-2-ylamino)benzoyl]amino}phenyl)sulfanyl]-3-phenylpropanoic acid;
3-[(3-{[3-(4,5-dihydro-1H-imidazol-2-ylamino)benzoyl]amino}phenyl)sulfanyl]-3-phenylpropanoic acid;
3-[(4-{[3-(4,5-dihydro-1H-imidazol-2-ylamino)benzoyl]amino}phenyl)sulfanyl]-3-phenylpropanoic acid;
3-[(2-{[3-(1H-imidazol-2-ylamino)benzoyl]amino}phenyl)sulfanyl]-3-phenylpropanoic acid;
3-[(3-{[3-(1H-imidazol-2-ylamino)benzoyl]amino}phenyl)sulfanyl]-3-phenylpropanoic acid;
3-[(4-{[3-(1H-imidazol-2-ylamino)benzoyl]amino}phenyl)sulfanyl]-3-phenylpropanoic acid;
3-phenyl-3-[(2-{[3-(2-pyridinylamino)benzoyl]amino}phenyl)sulfanyl]propanoic acid;
3-phenyl-3-[(3-{[3-(2-pyridinylamino)benzoyl]amino}phenyl)sulfanyl]propanoic acid;
3-phenyl-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-phenylpropanoic acid;
3-({3-[(4-{[amino(imino)methyl]amino}benzoyl)amino]phenyl}sulfanyl)-3-phenylpropanoic acid;
3-({4-[(4-{[amino(imino)methyl]amino}benzoyl)amino]phenyl}sulfanyl)-3-phenylpropanoic acid;
3-({2-[(4-{[(benzylamino)(imino)methyl]amino}benzoyl)amino]phenyl}sulfanyl)-3-phenylpropanoic acid;
3-({3-[(4-{[(benzylamino)(imino)methyl]amino}benzoyl)amino]phenyl}sulfanyl)-3-phenylpropanoic acid;
3-({4-[(4-{[(benzylamino)(imino)methyl]amino}benzoyl)amino]phenyl}sulfanyl)-3-phenylpropanoic acid;
3-{[2-({4-[(aminocarbonyl)amino]benzoyl}amino)phenyl]sulfanyl}-3-phenylpropanoic acid;
3-{[3-({4-[(aminocarbonyl)amino]benzoyl}amino)phenyl]sulfanyl}-3-phenylpropanoic acid;
3-{[4-({4-[(aminocarbonyl)amino]benzoyl}amino)phenyl]sulfanyl}-3-phenylpropanoic acid;
3-({2-[(4-{[(benzylamino)carbonyl]amino}benzoyl)amino]phenyl}sulfanyl)-3-phenylpropanoic acid;
3-({3-[(4-{[(benzylamino)carbonyl]amino}benzoyl)amino]phenyl}sulfanyl)-3-phenylpropanoic acid;
3-({4-[(4-{[(benzylamino)carbonyl]amino}benzoyl)amino]phenyl}sulfanyl)-3-phenylpropanoic acid;
3-[(2-{[4-(4,5-dihydro-1H-imidazol-2-ylamino)benzoyl]amino}phenyl)sulfanyl]-3-phenylpropanoic acid;
3-[(3-{[4-(4,5-dihydro-1H-imidazol-2-ylamino)benzoyl]amino}phenyl)sulfanyl]-3-phenylpropanoic acid;
3-[(4-{[4-(4,5-dihydro-1H-imidazol-2-ylamino)benzoyl]amino}phenyl)sulfanyl]-3-phenylpropanoic acid;
3-[(2-{[4-(1H-imidazol-2-ylamino)benzoyl]amino}phenyl)sulfanyl]-3-phenylpropanoic acid;
3-[(3-{[4-(1H-imidazol-2-ylamino)benzoyl]amino}phenyl)sulfanyl]-3-phenylpropanoic acid;
3-[(4-{[4-(1H-imidazol-2-ylamino)benzoyl]amino}phenyl)sulfanyl]-3-phenylpropanoic acid;
3-phenyl-3-[(2-{[4-(2-pyridinylamino)benzoyl]amino}phenyl)sulfanyl]propanoic acid;
3-phenyl-3-[(3-{[4-(2-pyridinylamino)benzoyl]amino}phenyl)sulfanyl]propanoic acid;
3-phenyl-3-[(4-{[4-(2-pyridinylamino)benzoyl]amino}phenyl)sulfanyl]propanoic acid;
3-{2-[(4-{[amino(imino)methyl]amino}benzoyl)amino]phenoxy}-3-(3-pyridinyl)propanoic acid;
3-{3-[(4-{[amino(imino)methyl]amino}benzoyl)amino]phenoxy}-3-(3-pyridinyl)propanoic acid;
3-{4-[(4-{[amino(imino)methyl]amino}benzoyl)amino]phenoxy}-3-(3-pyridinyl)propanoic acid;
3-{2-[(4-{[(benzylamino)(imino)methyl]amino}benzoyl)amino]phenoxy}-3-(3-pyridinyl)propanoic acid;
3-{3-[(4-{[(benzylamino)(imino)methyl]amino}benzoyl)amino]phenoxy}-3-(3-pyridinyl)propanoic acid;
3-{4-[(4-{[(benzylamino)(imino)methyl]amino}benzoyl)amino]phenoxy}-3-(3-pyridinyl)propanoic acid;
3-[2-({4-[(aminocarbonyl)amino]benzoyl}amino)phenoxy]-3-(3-pyridinyl)propanoic acid;
3-[3-({4-[(aminocarbonyl)amino]benzoyl}amino)phenoxy]-3-(3-pyridinyl)propanoic acid;
3-[4-({4-[(aminocarbonyl)amino]benzoyl}amino)phenoxy]-3-(3-pyridinyl)propanoic acid;
3-{2-[(4-{[(benzylamino)carbonyl]amino}benzoyl)amino]phenoxy}-3-(3-pyridinyl)propanoic acid;
3-{3-[(4-{[(benzylamino)carbonyl]amino}benzoyl)amino]phenoxy}-3-(3-pyridinyl)propanoic acid;
3-{4-[(4-{[(benzylamino)carbonyl]amino}benzoyl)amino]phenoxy}-3-(3-pyridinyl)propanoic acid;
3-(2-{[4-(4,5-dihydro-1H-imidazol-2-ylamino)benzoyl]amino}phenoxy)-3-(3-pyridinyl)propanoic acid;
3-(3-{[4-(4,5-dihydro-1H-imidazol-2-ylamino)benzoyl]amino}phenoxy)-3-(3-pyridinyl)propanoic acid;
3-(4-{[4-(4,5-dihydro-1H-imidazol-2-ylamino)benzoyl]amino}phenoxy)-3-(3-pyridinyl)propanoic acid;
3-(2-{[4-(1H-imidazol-2-ylamino)benzoyl]amino}phenoxy)-3-(3-pyridinyl)propanoic acid;
3-(3-{[4-(1H-imidazol-2-ylamino)benzoyl]amino}phenoxy)-3-(3-pyridinyl)propanoic acid;
3-(4-{[4-(1H-imidazol-2-ylamino)benzoyl]amino}phenoxy)-3-(3-pyridinyl)propanoic acid;
3-(3-pyridinyl)-3-(2-{[4-(2-pyridinylamino)benzoyl]amino}phenoxy)propanoic acid;
3-(3-pyridinyl)-3-(3-{[4-(2-pyridinylamino)benzoyl]amino}phenoxy)propanoic acid;
3-(3-pyridinyl)-3-(4-{[4-(2-pyridinylamino)benzoyl]amino}phenoxy)propanoic acid;
3-{2-[(3-{[amino(imino)methyl]amino}benzoyl)amino]phenoxy}-3-(3-pyridinyl)propanoic acid;
3-{3-[(3-{[amino(imino)methyl]amino}benzoyl)amino]phenoxy}-3-(3-pyridinyl)propanoic acid;
3-{4-[(3-{[amino(imino)methyl]amino}benzoyl)amino]phenoxy}-3-(3-pyridinyl)propanoic acid;
3-{2-[(3-{[(benzylamino)(imino)methyl]amino}benzoyl)amino]phenoxy}-3-(3-pyridinyl)propanoic acid;
3-{3-[(3-{[(benzylamino)(imino)methyl]amino}benzoyl)amino]phenoxy}-3-(3-pyridinyl)propanoic acid;
3-{4-[(3-{[(benzylamino)(imino)methyl]amino}benzoyl)amino]phenoxy}-3-(3-pyridinyl)propanoic acid;
3-[2-({3-[(aminocarbonyl)amino]benzoyl}amino)phenoxy]-3-(3-pyridinyl)propanoic acid;
3-[3-({3-[(aminocarbonyl)amino]benzoyl}amino)phenoxy]-3-(3-pyridinyl)propanoic acid;
3-[4-({3-[(aminocarbonyl)amino]benzoyl}amino)phenoxy]-3-(3-pyridinyl)propanoic acid;
3-{2-[(3-{[(benzylamino)carbonyl]amino}benzoyl)amino]phenoxy}-3-(3-pyridinyl)propanoic acid;
3-{3-[(3-{[(benzylamino)carbonyl]amino}benzoyl)amino]phenoxy}-3-(3-pyridinyl)propanoic acid;
3-{4-[(3-{[(benzylamino)carbonyl]amino}benzoyl)amino]phenoxy}-3-(3-pyridinyl)propanoic acid;
3-(2-{[3-(4,5-dihydro-1H-imidazol-2-ylamino)benzoyl]amino}phenoxy)-3-(3-pyridinyl)propanoic acid;
3-(3-{[3-(4,5-dihydro-1H-imidazol-2-ylamino)benzoyl]amino}phenoxy)-3-(3-pyridinyl)propanoic acid;
3-(4-{[3-(4,5-dihydro-1H-imidazol-2-ylamino)benzoyl]amino}phenoxy)-3-(3-pyridinyl)propanoic acid;
3-(2-{[3-(1H-imidazol-2-ylamino)benzoyl]amino}phenoxy)-3-(3-pyridinyl)propanoic acid;
3-(3-{[3-(1H-imidazol-2-ylamino)benzoyl]amino}phenoxy)-3-(3-pyridinyl)propanoic acid;

3-(4-{[3-(1H-imidazol-2-ylamino)benzoyl]amino}phenoxy)-3-(3-pyridinyl)propanoic acid;
3-(3-pyridinyl)-3-(2-{[3-(2-pyridinylamino)benzoyl]amino}phenoxy)propanoic acid;
3-(3-pyridinyl)-3-(3-{[3-(2-pyridinylamino)benzoyl]amino}phenoxy)propanoic acid;
3-(3-pyridinyl)-3-(4-{[3-(2-pyridinylamino)benzoyl]amino}phenoxy)propanoic acid;
3-{2-[(3-{[amino(imino)methyl]amino}benzoyl)amino]phenoxy}-3-phenylpropanoic acid;
3-{3-[(3-{[amino(imino)methyl]amino}benzoyl)amino]phenoxy}-3-phenylpropanoic acid;
3-{4-[(3-{[amino(imino)methyl]amino}benzoyl)amino]phenoxy}-3-phenylpropanoic acid;
3-{2-[(3-{[(benzylamino)(imino)methyl]amino}benzoyl)amino]phenoxy}-3-phenylpropanoic acid;
3-{3-[(3-{[(benzylamino)(imino)methyl]amino}benzoyl)amino]phenoxy}-3-phenylpropanoic acid;
3-{4-[(3-{[(benzylamino)(imino)methyl]amino}benzoyl)amino]phenoxy}-3-phenylpropanoic acid;
3-[2-({3-[(aminocarbonyl)amino]benzoyl}amino)phenoxy]-3-phenylpropanoic acid;
3-[3-({3-[(aminocarbonyl)amino]benzoyl}amino)phenoxy]-3-phenylpropanoic acid;
3-[4-({3-[(aminocarbonyl)amino]benzoyl}amino)phenoxy]-3-phenylpropanoic acid;
3-{2-[(3-{[(benzylamino)carbonyl]amino}benzoyl)amino]phenoxy}-3-phenylpropanoic acid;
3-{3-[(3-{[(benzylamino)carbonyl]amino}benzoyl)amino]phenoxy}-3-phenylpropanoic acid;
3-{4-[(3-{[(benzylamino)carbonyl]amino}benzoyl)amino]phenoxy}-3-phenylpropanoic acid;
3-(2-{[3-(4,5-dihydro-1H-imidazol-2-ylamino)benzoyl]amino}phenoxy)-3-phenylpropanoic acid;
3-(3-{[3-(4,5-dihydro-1H-imidazol-2-ylamino)benzoyl]amino}phenoxy)-3-phenylpropanoic acid;
3-(4-{[3-(4,5-dihydro-1H-imidazol-2-ylamino)benzoyl]amino}phenoxy)-3-phenylpropanoic acid;
3-(2-{[3-(1H-imidazol-2-ylamino)benzoyl]amino}phenoxy)-3-phenylpropanoic acid;
3-(3-{[3-(1H-imidazol-2-ylamino)benzoyl]amino}phenoxy)-3-phenylpropanoic acid;
3-(4-{[3-(1H-imidazol-2-ylamino)benzoyl]amino}phenoxy)-3-phenylpropanoic acid;
3-phenyl-3-(2-{[3-(2-pyridinylamino)benzoyl]amino}phenoxy)propanoic acid;
3-phenyl-3-(3-{[3-(2-pyridinylamino)benzoyl]amino}phenoxy)propanoic acid;
3-phenyl-3-(4-{[3-(2-pyridinylamino)benzoyl]amino}phenoxy)propanoic acid;
3-{2-[(4-{[amino(imino)methyl]amino}benzoyl)amino]phenoxy}-3-phenylpropanoic acid;
3-{3-[(4-{[amino(imino)methyl]amino}benzoyl)amino]phenoxy}-3-phenylpropanoic acid;
3-{4-[(4-{[amino(imino)methyl]amino}benzoyl)amino]phenoxy}-3-phenylpropanoic acid;
3-{2-[(4-{[(benzylamino)(imino)methyl]amino}benzoyl)amino]phenoxy}-3-phenylpropanoic acid;
3-{3-[(4-{[(benzylamino)(imino)methyl]amino}benzoyl)amino]phenoxy}-3-phenylpropanoic acid;
3-{4-[(4-{[(benzylamino)(imino)methyl]amino}benzoyl)amino]phenoxy}-3-phenylpropanoic acid;
3-[2-({4-[(aminocarbonyl)amino]benzoyl}amino)phenoxy]-3-phenylpropanoic acid;
3-[3-({4-[(aminocarbonyl)amino]benzoyl}amino)phenoxy]-3-phenylpropanoic acid;
3-[4-({4-[(aminocarbonyl)amino]benzoyl}amino)phenoxy]-3-phenylpropanoic acid;
3-{2-[(4-{[(benzylamino)carbonyl]amino}benzoyl)amino]phenoxy}-3-phenylpropanoic acid;
3-{3-[(4-{[(benzylamino)carbonyl]amino}benzoyl)amino]phenoxy}-3-phenylpropanoic acid;
3-{4-[(4-{[(benzylamino)carbonyl]amino}benzoyl)amino]phenoxy}-3-phenylpropanoic acid;
3-(2-{[4-(4,5-dihydro-1H-imidazol-2-ylamino)benzoyl]amino}phenoxy)-3-phenylpropanoic acid;
3-(3-{[4-(4,5-dihydro-1H-imidazol-2-ylamino)benzoyl]amino}phenoxy)-3-phenylpropanoic acid;
3-(4-{[4-(4,5-dihydro-1H-imidazol-2-ylamino)benzoyl]amino}phenoxy)-3-phenylpropanoic acid;
3-(2-{[4-(1H-imidazol-2-ylamino)benzoyl]amino}phenoxy)-3-phenylpropanoic acid;
3-(3-{[4-(1H-imidazol-2-ylamino)benzoyl]amino}phenoxy)-3-phenylpropanoic acid;
3-(4-{[4-(1H-imidazol-2-ylamino)benzoyl]amino}phenoxy)-3-phenylpropanoic acid;
3-phenyl-3-(2-{[4-(2-pyridinylamino)benzoyl]amino}phenoxy)propanoic acid;
3-phenyl-3-(3-{[4-(2-pyridinylamino)benzoyl]amino}phenoxy)propanoic acid;
3-phenyl-3-(4-{[4-(2-pyridinylamino)benzoyl]amino}phenoxy)propanoic acid;
3-({2-[(3-{[amino(imino)methyl]amino}benzoyl)amino]phenyl}sulfinyl)-3-(3-pyridinyl)propanoic acid;
3-({3-[(3-{[amino(imino)methyl]amino}benzoyl)amino]phenyl}sulfinyl)-3-(3-pyridinyl)propanoic acid;
3-({4-[(3-{[amino(imino)methyl]amino}benzoyl)amino]phenyl}sulfinyl)-3-(3-pyridinyl)propanoic acid;
3-({2-[(3-{[(benzylamino)(imino)methyl]amino}benzoyl)amino]phenyl}sulfinyl)-3-(3-pyridinyl)propanoic acid;
3-({3-[(3-{[(benzylamino)(imino)methyl]amino}benzoyl)amino]phenyl}sulfinyl)-3-(3-pyridinyl)propanoic acid;
3-({4-[(3-{[(benzylamino)(imino)methyl]amino}benzoyl)amino]phenyl}sulfinyl)-3-(3-pyridinyl)propanoic acid;
3-{[2-({3-[(aminocarbonyl)amino]benzoyl}amino)phenyl]sulfinyl}-3-(3-pyridinyl)propanoic acid;
3-{[3-({3-[(aminocarbonyl)amino]benzoyl}amino)phenyl]sulfinyl}-3-(3-pyridinyl)propanoic acid;
3-{[4-({3-[(aminocarbonyl)amino]benzoyl}amino)phenyl]sulfinyl}-3-(3-pyridinyl)propanoic acid;
3-({2-[(3-{[(benzylamino)carbonyl]amino}benzoyl)amino]phenyl}sulfinyl)-3-(3-pyridinyl)propanoic acid;
3-({3-[(3-{[(benzylamino)carbonyl]amino}benzoyl)amino]phenyl}sulfinyl)-3-(3-pyridinyl)propanoic acid;
3-({4-[(3-{[(benzylamino)carbonyl]amino}benzoyl)amino]phenyl}sulfinyl)-3-(3-pyridinyl)propanoic acid;
3-[(2-{[3-(4,5-dihydro-1H-imidazol-2-ylamino)benzoyl]amino}phenyl)sulfinyl]-3-(3-pyridinyl)propanoic acid;
3-[(3-{[3-(4,5-dihydro-1H-imidazol-2-ylamino)benzoyl]amino}phenyl)sulfinyl]-3-(3-pyridinyl)propanoic acid;
3-[(4-{[3-(4,5-dihydro-1H-imidazol-2-ylamino)benzoyl]amino}phenyl)sulfinyl]-3-(3-pyridinyl)propanoic acid;
3-[(2-{[3-(1H-imidazol-2-ylamino)benzoyl]amino}phenyl)sulfinyl]-3-(3-pyridinyl)propanoic acid;
3-[(3-{[3-(1H-imidazol-2-ylamino)benzoyl]amino}phenyl)sulfinyl]-3-(3-pyridinyl)propanoic acid;
3-[(4-{[3-(1H-imidazol-2-ylamino)benzoyl]amino}phenyl)sulfinyl]-3-(3-pyridinyl)propanoic acid;
3-(3-pyridinyl)-3-[(2-{[3-(2-pyridinylamino)benzoyl]amino}phenyl)sulfinyl]propanoic acid;
3-(3-pyridinyl)-3-[(3-{[3-(2-pyridinylamino)benzoyl]amino}phenyl)sulfinyl]propanoic acid;
3-(3-pyridinyl)-3-[(4-{[3-(2-pyridinylamino)benzoyl]amino}phenyl)sulfinyl]propanoic acid;
3-({2-[(4-{[amino(imino)methyl]amino}benzoyl)amino]phenyl}sulfinyl)-3-(3-pyridinyl)propanoic acid;

3-({3-[(4-{[amino(imino)methyl]amino}benzoyl)amino]phenyl}sulfinyl)-3-(3-pyridinyl)propanoic acid;
3-({4-[(4-{[amino(imino)methyl]amino}benzoyl)amino]phenyl}sulfinyl)-3-(3-pyridinyl)propanoic acid;
3-({2-[(4-{[(benzylamino)(imino)methyl]amino}benzoyl)amino]phenyl}sulfinyl)-3-(3-pyridinyl)propanoic acid;
3-({3-[(4-{[(benzylamino)(imino)methyl]amino}benzoyl)amino]phenyl}sulfinyl)-3-(3-pyridinyl)propanoic acid;
3-({4-[(4-{[(benzylamino)(imino)methyl]amino}benzoyl)amino]phenyl}sulfinyl)-3-(3-pyridinyl)propanoic acid;
3-{[2-({4-[(aminocarbonyl)amino]benzoyl}amino)phenyl]sulfinyl}-3-(3-pyridinyl)propanoic acid;
3-{[3-({4-[(aminocarbonyl)amino]benzoyl}amino)phenyl]sulfinyl}-3-(3-pyridinyl)propanoic acid;
3-{[4-({4-[(aminocarbonyl)amino]benzoyl}amino)phenyl]sulfinyl}-3-(3-pyridinyl)propanoic acid;
3-({2-[(4-{[(benzylamino)carbonyl]amino}benzoyl)amino]phenyl}sulfinyl)-3-(3-pyridinyl)propanoic acid;
3-({3-[(4-{[(benzylamino)carbonyl]amino}benzoyl)amino]phenyl}sulfinyl)-3-(3-pyridinyl)propanoic acid;
3-({4-[(4-{[(benzylamino)carbonyl]amino}benzoyl)amino]phenyl}sulfinyl)-3-(3-pyridinyl)propanoic acid;
3-[(2-{[4-(4,5-dihydro-1H-imidazol-2-ylamino)benzoyl]amino}phenyl)sulfinyl]-3-(3-pyridinyl)propanoic acid;
3-[(3-{[4-(4,5-dihydro-1H-imidazol-2-ylamino)benzoyl]amino}phenyl)sulfinyl]-3-(3-pyridinyl)propanoic acid;
3-[(4-{[4-(4,5-dihydro-1H-imidazol-2-ylamino)benzoyl]amino}phenyl)sulfinyl]-3-(3-pyridinyl)propanoic acid;
3-[{(2-[4-(1H-imidazol-2-ylamino)benzoyl]amino}phenyl)sulfinyl]-3-(3-pyridinyl)propanoic acid;
3-[(3-{[4-(1H-imidazol-2-ylamino)benzoyl]amino}phenyl)sulfinyl]-3-(3-pyridinyl)propanoic acid;
3-[(4-{[4-(1H-imidazol-2-ylamino)benzoyl]amino}phenyl)sulfinyl]-3-(3-pyridinyl)propanoic acid;
3-(3-pyridinyl)-3-[(2-{[4-(2-pyridinylamino)benzoyl]amino}phenyl)sulfinyl]propanoic acid;
3-(3-pyridinyl)-3-[(3-{[4-(2-pyridinylamino)benzoyl]amino}phenyl)sulfinyl]propanoic acid;
3-(3-pyridinyl)-3-[(4-{[4-(2-pyridinylamino)benzoyl]amino}phenyl)sulfinyl]propanoic acid;
3-({2-[(3-{[amino(imino)methyl]amino}benzoyl)amino]phenyl}sulfonyl)-3-(3-pyridinyl)propanoic acid;
3-({3-[(3-{[amino(imino)methyl]amino}benzoyl)amino]phenyl}sulfonyl)-3-(3-pyridinyl)propanoic acid;
3-({4-[(3-{[amino(imino)methyl]amino}benzoyl)amino]phenyl}sulfonyl)-3-(3-pyridinyl)propanoic acid;
3-({2-[(3-{[(benzylamino)(imino)methyl]amino}benzoyl)amino]phenyl}sulfonyl)-3-(3-pyridinyl)propanoic acid;
3-({3-[(3-{[(benzylamino)(imino)methyl]amino}benzoyl)amino]phenyl}sulfonyl)-3-(3-pyridinyl)propanoic acid;
3-({4-[(3-{[(benzylamino)(imino)methyl]amino}benzoyl)amino]phenyl}sulfonyl)-3-(3-pyridinyl)propanoic acid;
3-{[2-({3-[(aminocarbonyl)amino]benzoyl}amino)phenyl]sulfonyl}-3-(3-pyridinyl)propanoic acid;
3-{[3-({3-[(aminocarbonyl)amino]benzoyl}amino)phenyl]sulfonyl}-3-(3-pyridinyl)propanoic acid;
3-{[4-({3-[(aminocarbonyl)amino]benzoyl}amino)phenyl]sulfonyl}-3-(3-pyridinyl)propanoic acid;
3-({2-[(3-{[(benzylamino)carbonyl]amino}benzoyl)amino]phenyl}sulfonyl)-3-(3-pyridinyl)propanoic acid;
3-({3-[(3-{[(benzylamino)carbonyl]amino}benzoyl)amino]phenyl}sulfonyl)-3-(3-pyridinyl)propanoic acid;
3-({4-[(3-{[(benzylamino)carbonyl]amino}benzoyl)amino]phenyl}sulfonyl)-3-(3-pyridinyl)propanoic acid;
3-[(2-{[3-(4,5-dihydro-1H-imidazol-2-ylamino)benzoyl]amino}phenyl)sulfonyl]-3-(3-pyridinyl)propanoic acid;
3-[(3-{[3-(4,5-dihydro-1H-imidazol-2-ylamino)benzoyl]amino}phenyl)sulfonyl]-3-(3-pyridinyl)propanoic acid;
3-[(4-{[3-(4,5-dihydro-1H-imidazol-2-ylamino)benzoyl]amino}phenyl)sulfonyl]-3-(3-pyridinyl)propanoic acid;
3-[(2-{[3-(1H-imidazol-2-ylamino)benzoyl]amino}phenyl)sulfonyl]-3-(3-pyridinyl)propanoic acid;
3-[(3-{[3-(1H-imidazol-2-ylamino)benzoyl]amino}phenyl)sulfonyl]-3-(3-pyridinyl)propanoic acid;
3-[(4-{[3-(1H-imidazol-2-ylamino)benzoyl]amino}phenyl)sulfonyl]-3-(3-pyridinyl)propanoic acid;
3-(3-pyridinyl)-3-[(2-{[3-(2-pyridinylamino)benzoyl]amino}phenyl)sulfonyl]propanoic acid;
3-(3-pyridinyl)-3-[(3-{[3-(2-pyridinylamino)benzoyl]amino}phenyl)sulfonyl]propanoic acid;
3-(3-pyridinyl)-3-[(4-{[3-(2-pyridinylamino)benzoyl]amino}phenyl)sulfonyl]propanoic acid;
3-({2-[(4-{[amino(imino)methyl]amino}benzoyl)amino]phenyl}sulfonyl)-3-(3-pyridinyl)propanoic acid;
3-({3-[(4-{[amino(imino)methyl]amino}benzoyl)amino]phenyl}sulfonyl)-3-(3-pyridinyl)propanoic acid;
3-({4-[(4-{[amino(imino)methyl]amino}benzoyl)amino]phenyl}sulfonyl)-3-(3-pyridinyl)propanoic acid;
3-({2-[(4-{[(benzylamino)(imino)methyl]amino}benzoyl)amino]phenyl}sulfonyl)-3-(3-pyridinyl)propanoic acid;
3-({3-[(4-{[(benzylamino)(imino)methyl]amino}benzoyl)amino]phenyl}sulfonyl)-3-(3-pyridinyl)propanoic acid;
3-({4-[(4-{[(benzylamino)(imino)methyl]amino}benzoyl)amino]phenyl}sulfonyl)-3-(3-pyridinyl)propanoic acid;
3-{[2-({4-[(aminocarbonyl)amino]benzoyl}amino)phenyl]sulfonyl}-3-(3-pyridinyl)propanoic acid;
3-{[3-({4-[(aminocarbonyl)amino]benzoyl}amino)phenyl]sulfonyl}-3-(3-pyridinyl)propanoic acid;
3-{[4-({4-[(aminocarbonyl)amino]benzoyl}amino)phenyl]sulfonyl}-3-(3-pyridinyl)propanoic acid;
3-({2-[(4-{[(benzylamino)carbonyl]amino}benzoyl)amino]phenyl}sulfonyl)-3-(3-pyridinyl)propanoic acid;
3-({3-[(4-{[(benzylamino)carbonyl]amino}benzoyl)amino]phenyl}sulfonyl)-3-(3-pyridinyl)propanoic acid;
3-({4-[(4-{[(benzylamino)carbonyl]amino}benzoyl)amino]phenyl}sulfonyl)-3-(3-pyridinyl)propanoic acid;
3-[(2-{[4-(4,5-dihydro-1H-imidazol-2-ylamino)benzoyl]amino}phenyl)sulfonyl]-3-(3-pyridinyl)propanoic acid;
3-[(3-{[4-(4,5-dihydro-1H-imidazol-2-ylamino)benzoyl]amino}phenyl)sulfonyl]-3-(3-pyridinyl)propanoic acid;
3-[(4-{[4-(4,5-dihydro-1H-imidazol-2-ylamino)benzoyl]amino}phenyl)sulfonyl]-3-(3-pyridinyl)propanoic acid;
3-[(2-{[4-(1H-imidazol-2-ylamino)benzoyl]amino}phenyl)sulfonyl]-3-(3-pyridinyl)propanoic acid;
3-[(3-{[4-(1H-imidazol-2-ylamino)benzoyl]amino}phenyl)sulfonyl]-3-(3-pyridinyl)propanoic acid;
3-[(4-{[4-(1H-imidazol-2-ylamino)benzoyl]amino}phenyl)sulfonyl]-3-(3-pyridinyl)propanoic acid;
3-(3-pyridinyl)-3-[(2-{[4-(2-pyridinylamino)benzoyl]amino}phenyl)sulfonyl]propanoic acid;
3-(3-pyridinyl)-3-[(3-{[4-(2-pyridinylamino)benzoyl]amino}phenyl)sulfonyl]propanoic acid;
3-(3-pyridinyl)-3-[(4-{[4-(2-pyridinylamino)benzoyl]amino}phenyl)sulfonyl]propanoic acid;
3-({3-[(3-{[amino(imino)methyl]amino}benzoyl)amino]phenyl sulfinyl}-3-phenylpropanoic acid;
3-({2-[(3-{[amino(imino)methyl]amino}benzoyl)amino]phenyl}sulfinyl)-3-phenylpropanoic acid;
3-({4-[(3-{[amino(imino)methyl]amino}benzoyl)amino]phenyl}sulfinyl)-3phenylpropanoic acid;
3-({2-[(3-{[(benzylamino)(imino)methyl]amino}benzoyl)amino]phenyl}sulfinyl)-3-phenylpropanoic acid;
3-({3-[(3-{[(benzylamino)(imino)methyl]amino}benzoyl)amino]phenyl}sulfinyl)-3-phenylpropanoic acid;
3-({4-[(3-{[(benzylamino)(imino)methyl]amino}benzoyl)amino]phenyl}sulfinyl)-3-phenylpropanoic acid;

3-{[2-({3-[(aminocarbonyl)amino]benzoyl}amino)phenyl]sulfinyl}-3-phenylpropanoic acid;
3-{[3-({3-[(aminocarbonyl)amino]benzoyl}amino)phenyl]sulfinyl}-3-phenylpropanoic acid;
3-{[4-({3-[(aminocarbonyl)amino]benzoyl}amino)phenyl]sulfinyl}-3-phenylpropanoic acid;
3-({2-[(3-{[(benzylamino)carbonyl]amino}benzoyl)amino]phenyl}sulfinyl)-3-phenylpropanoic acid;
3-({3-[(3-{[(benzylamino)carbonyl]amino}benzoyl)amino]phenyl}sulfinyl)-3-phenylpropanoic acid;
3-({4-[(3-{[(benzylamino)carbonyl]amino}benzoyl)amino]phenyl}sulfinyl)-3-phenylpropanoic acid;
3-[(2-{[3-(4,5-dihydro-1H-imidazol-2-ylamino)benzoyl]amino}phenyl)sulfinyl]-3-phenylpropanoic acid;
3-[(3-{[3-(4,5-dihydro-1H-imidazol-2-ylamino)benzoyl]amino}phenyl)sulfinyl]-3-phenylpropanoic acid;
3-[(4-{[3-(4,5-dihydro-1H-imidazol-2-ylamino)benzoyl]amino}phenyl)sulfinyl]-3-phenylpropanoic acid;
3-[(2-{[3-(1H-imidazol-2-ylamino)benzoyl]amino}phenyl)sulfinyl]-3-phenylpropanoic acid;
3-[(3-{[3-(1H-imidazol-2-ylamino)benzoyl]amino}phenyl)sulfinyl]-3-phenylpropanoic acid;
3-[(4-{[3-(1H-imidazol-2-ylamino)benzoyl]amino}phenyl)sulfinyl]-3-phenylpropanoic acid;
3-phenyl-3-[(2-{[3-(2-pyridinylamino)benzoyl]amino}phenyl)sulfinyl]propanoic acid;
3-phenyl-3-[(3-{[3-(2-pyridinylamino)benzoyl]amino}phenyl)sulfinyl]propanoic acid;
3-phenyl-3-[(4-{[3-(2-pyridinylamino)benzoyl]amino}phenyl)sulfinyl]propanoic acid;
3-({2-[(4-{[amino(imino)methyl]amino}benzoyl)amino]phenyl}sulfinyl)-3-phenylpropanoic acid;
3-({3-[(4-{[amino(imino)methyl]amino}benzoyl)amino]phenyl}sulfinyl)-3-phenylpropanoic acid;
3-({4-[(4-{[amino(imino)methyl]amino}benzoyl)amino]phenyl}sulfinyl)-3-phenylpropanoic acid;
3-({2-[(4-{[(benzylamino)(imino)methyl]amino}benzoyl)amino]phenyl}sulfinyl)-3-phenylpropanoic acid;
3-({3-[(4-{[(benzylamino)(imino)methyl]amino}benzoyl)amino]phenyl}sulfinyl)-3-phenylpropanoic acid;
3-({4-[(4-{[(benzylamino)(imino)methyl]amino}benzoyl)amino]phenyl}sulfinyl)-3-phenylpropanoic acid;
3-{[2-({4-[(aminocarbonyl)amino]benzoyl}amino)phenyl]sulfinyl}-3-phenylpropanoic acid;
3-{[3-({4-[(aminocarbonyl)amino]benzoyl}amino)phenyl]sulfinyl}-3-phenylpropanoic acid;
3-{[4-({4-[(aminocarbonyl)amino]benzoyl}amino)phenyl]sulfinyl}-3-phenylpropanoic acid;
3-({2-[(4-{[(benzylamino)carbonyl]amino}benzoyl)amino]phenyl}sulfinyl)-3-phenylpropanoic acid;
3-({3-[(4-{[(benzylamino)carbonyl]amino}benzoyl)amino]phenyl}sulfinyl)-3-phenylpropanoic acid;
3-({4-[(4-{[(benzylamino)carbonyl]amino}benzoyl)amino]phenyl}sulfinyl)-3-phenylpropanoic acid;
3-[(2-{[4-(4,5-dihydro-1H-imidazol-2-ylamino)benzoyl]amino}phenyl)sulfinyl]-3-phenylpropanoic acid;
3-[(3-{[4-(4,5-dihydro-1H-imidazol-2-ylamino)benzoyl]amino}phenyl)sulfinyl]-3-phenylpropanoic acid;
3-[(4-{[4-(4,5-dihydro-1H-imidazol-2-ylamino)benzoyl]amino}phenyl)sulfinyl]-3-phenylpropanoic acid;
3-[(2-{[4-(1H-imidazol-2-ylamino)benzoyl]amino}phenyl)sulfinyl]-3-phenylpropanoic acid;
3-[(3-{[4-(1H-imidazol-2-ylamino)benzoyl]amino}phenyl)sulfinyl]-3-phenylpropanoic acid;
3-[(4-{[4-(1H-imidazol-2-ylamino)benzoyl]amino}phenyl)sulfinyl]-3-phenylpropanoic acid;
3-phenyl-3-[(2-{[4-(2-pyridinylamino)benzoyl]amino}phenyl)sulfinyl]propanoic acid;
3-phenyl-3-[(3-{[4-(2-pyridinylamino)benzoyl]amino}phenyl)sulfinyl]propanoic acid;
3-phenyl-3-[(4-{[4-(2-pyridinylamino)benzoyl]amino}phenyl)sulfinyl]propanoic acid;
3-({3-[(3-{[amino(imino)methyl]amino}benzoyl)amino]phenyl}sulfonyl)-3-phenylpropanoic acid;
3-({2-[(3-{[amino(imino)methyl]amino}benzoyl)amino]phenyl}sulfonyl)-3-phenylpropanoic acid;
3-({4-[(3-{[amino(imino)methyl]amino}benzoyl)amino]phenyl}sulfonyl)-3phenylpropanoic acid;
3-({2-[(3-{[(benzylamino)(imino)methyl]amino}benzoyl)amino]phenyl}sulfonyl)-3-phenylpropanoic acid;
3-({3-[(3-{[(benzylamino)(imino)methyl]amino}benzoyl)amino]phenyl}sulfonyl)-3-phenylpropanoic acid;
3-({4-[(3-{[(benzylamino)(imino)methyl]amino}benzoyl)amino]phenyl}sulfonyl)-3-phenylpropanoic acid;
3-{[2-({3-[(aminocarbonyl)amino]benzoyl}amino)phenyl]sulfonyl}-3-phenylpropanoic acid;
3-{[3-({3-[(aminocarbonyl)amino]benzoyl}amino)phenyl]sulfonyl}-3-phenylpropanoic acid;
3-{[4-({3-[(aminocarbonyl)amino]benzoyl}amino)phenyl]sulfonyl}-3-phenylpropanoic acid;
3-({2-[(3-{[(benzylamino)carbonyl]amino}benzoyl)amino]phenyl}sulfonyl)-3-phenylpropanoic acid;
3-({3-[(3-{[(benzylamino)carbonyl]amino}benzoyl)amino]phenyl}sulfonyl)-3-phenylpropanoic acid;
3-({4-[(3-{[(benzylamino)carbonyl]amino}benzoyl)amino]phenyl}sulfonyl)-3-phenylpropanoic acid;
3-[(2-{[3-(4,5-dihydro-1H-imidazol-2-ylamino)benzoyl]amino}phenyl)sulfonyl]-3-phenylpropanoic acid;
3-[(3-{[3-(4,5-dihydro-1H-imidazol-2-ylamino)benzoyl]amino}phenyl)sulfonyl]-3-phenylpropanoic acid;
3-[(4-{[3-(4,5-dihydro-1H-imidazol-2-ylamino)benzoyl]amino}phenyl)sulfonyl]-3-phenylpropanoic acid;
3-[(2-{[3-(1H-imidazol-2-ylamino)benzoyl]amino}phenyl)sulfonyl]-3-phenylpropanoic acid;
3-[(3-{[3-(1H-imidazol-2-ylamino)benzoyl]amino}phenyl)sulfonyl]-3-phenylpropanoic acid;
3-[(4-{[3-(1H-imidazol-2-ylamino)benzoyl]amino}phenyl)sulfonyl]-3-phenylpropanoic acid;
3-phenyl-3-[(2-{[3-(2-pyridinylamino)benzoyl]amino}phenyl)sulfonyl]propanoic acid;
3-phenyl-3-[(3-{[3-(2-pyridinylamino)benzoyl]amino}phenyl)sulfonyl]propanoic acid;
3-phenyl-3-[(4-{[3-(2-pyridinylamino)benzoyl]amino}phenyl)sulfonyl]propanoic acid;
3-({2-[(4-{[amino(imino)methyl]amino}benzoyl)amino]phenyl}sulfonyl)-3-phenylpropanoic acid;
3-({3-[(4-{[amino(imino)methyl]amino}benzoyl)amino]phenyl}sulfonyl)-3-phenylpropanoic acid;
3-({4-[(4-{[amino(imino)methyl]amino}benzoyl)amino]phenyl}sulfonyl)-3-phenylpropanoic acid;
3-({2-[(4-{[(benzylamino)(imino)methyl]amino}benzoyl)amino]phenyl}sulfonyl)-3-phenylpropanoic acid;
3-({3-[(4-{[(benzylamino)(imino)methyl]amino}benzoyl)amino]phenyl}sulfonyl)-3-phenylpropanoic acid;
3-({4-[(4-{[(benzylamino)(imino)methyl]amino}benzoyl)amino]phenyl}sulfonyl)-3-phenylpropanoic acid;
3-{[2-({4-[(aminocarbonyl)amino]benzoyl}amino)phenyl]sulfonyl}-3-phenylpropanoic acid;
3-{[3-({4-[(aminocarbonyl)amino]benzoyl}amino)phenyl]sulfonyl}-3-phenylpropanoic acid;
3-{[4-({4-[(aminocarbonyl)amino]benzoyl}amino)phenyl]sulfonyl}-3-phenylpropanoic acid;
3-({2-[(4-{[(benzylamino)carbonyl]amino}benzoyl)amino]phenyl}sulfonyl)-3-phenylpropanoic acid;
3-({3-[(4-{[(benzylamino)carbonyl]amino}benzoyl)amino]phenyl}sulfonyl)-3-phenylpropanoic acid;

3-({4-[(4-{[(benzylamino)carbonyl]amino}benzoyl)amino]phenyl}sulfonyl)-3-phenylpropanoic acid;
3-[(2-{[4-(4,5-dihydro-1H-imidazol-2-ylamino)benzoyl]amino}phenyl)sulfonyl]-3-phenylpropanoic acid;
3-[(3-{[4-(4,5-dihydro-1H-imidazol-2-ylamino)benzoyl]amino}phenyl)sulfonyl]-3-phenylpropanoic acid;
3-[(4-{[4-(4,5-dihydro-1H-imidazol-2-ylamino)benzoyl]amino}phenyl)sulfonyl]-3-phenylpropanoic acid;
3-[(2-{[4-(1H-imidazol-2-ylamino)benzoyl]amino}phenyl)sulfonyl]-3-phenylpropanoic acid;
3-[(3-{[4-(1H-imidazol-2-ylamino)benzoyl]amino}phenyl)sulfonyl]-3-phenylpropanoic acid;
3-[(4-{[4-(1H-imidazol-2-ylamino)benzoyl]amino}phenyl)sulfonyl]-3-phenylpropanoic acid;
3-phenyl-3-[(2-{[4-(2-pyridinylamino)benzoyl]amino}phenyl)sulfonyl]propanoic acid;
3-phenyl-3-[(3-{[4-(2-pyridinylamino)benzoyl]amino}phenyl)sulfonyl]propanoic acid;
3-phenyl-3-[(4-{[4-(2-pyridinylamino)benzoyl]amino}phenyl)sulfonyl]propanoic acid;
3-phenyl-3-[(2-{[4-(2-pyridinylamino)benzoyl]amino}phenyl)sulfonyl]propanoic acid;
3-phenyl-3-[(3-{[4-(2-pyridinylamino)benzoyl]amino}phenyl)sulfonyl]propanoic acid;
3-phenyl-3-[(4-{[4-(2-pyridinylamino)benzoyl]amino}phenyl)sulfonyl]propanoic acid;
3-(3-pyridinyl)-3-(2-{[3-(1,4,5,6-tetrahydro-2-pyrimidinylamino)benzoyl]amino}phenoxy)propanoic acid;
3-(3-pyridinyl)-3-(3-{[3-(1,4,5,6-tetrahydro-2-pyrimidinylamino)benzoyl]amino}phenoxy)propanoic acid;
3-(3-pyridinyl)-3-(4-{[3-(1,4,5,6-tetrahydro-2-pyrimidinylamino)benzoyl]amino}phenoxy)propanoic acid;
3-(3-pyridinyl)-3-(2-{[4-(1,4,5,6-tetrahydro-2-pyrimidinylamino)benzoyl]amino}phenoxy)propanoic acid;
3-(3-pyridinyl)-3-(3-{[4-(1,4,5,6-tetrahydro-2-pyrimidinylamino)benzoyl]amino}phenoxy)propanoic acid;
3-(3-pyridinyl)-3-(4-{[4-(1,4,5,6-tetrahydro-2-pyrimidinylamino)benzoyl]amino}phenoxy)propanoic acid;
3-phenyl-3-(2-{[3-(1,4,5,6-tetrahydro-2-pyrimidinylamino)benzoyl]amino}phenoxy)propanoic acid;
3-phenyl-3-(3-{[3-(1,4,5,6-tetrahydro-2-pyrimidinylamino)benzoyl]amino}phenoxy)propanoic acid;
3-phenyl-3-(4-{[3-(1,4,5,6-tetrahydro-2-pyrimidinylamino)benzoyl]amino}phenoxy)propanoic acid;
3-phenyl-3-(2-{[4-(1,4,5,6-tetrahydro-2-pyrimidinylamino)benzoyl]amino}phenoxy)propanoic acid;
3-phenyl-3-(3-{[4-(1,4,5,6-tetrahydro-2-pyrimidinylamino)benzoyl]amino}phenoxy)propanoic acid;
3-phenyl-3-(4-{[4-(1,4,5,6-tetrahydro-2-pyrimidinylamino)benzoyl]amino}phenoxy)propanoic acid;
3-(3-pyridinyl)-3-[(2-{[3-(1,4,5,6-tetrahydro-2-pyrimidinylamino)benzoyl]amino}phenyl)sulfanyl]propanoic acid;
3-(3-pyridinyl)-3-[(3-{[3-(1,4,5,6-tetrahydro-2-pyrimidinylamino)benzoyl]amino}phenyl)sulfanyl]propanoic acid;
3-(3-pyridinyl)-3-[(4-{[3-(1,4,5,6-tetrahydro-2-pyrimidinylamino)benzoyl]amino}phenyl)sulfanyl]propanoic acid;
3-(3-pyridinyl)-3-[(2-{[4-(1,4,5,6-tetrahydro-2-pyrimidinylamino)benzoyl]amino}phenyl)sulfanyl]propanoic acid;
3-(3-pyridinyl)-3-[(3-{[4-(1,4,5,6-tetrahydro-2-pyrimidinylamino)benzoyl]amino}phenyl)sulfanyl]propanoic acid;
3-(3-pyridinyl)-3-[(4-{[4-(1,4,5,6-tetrahydro-2-pyrimidinylamino)benzoyl]amino}phenyl)sulfanyl]propanoic acid;
3-phenyl-3-[(2-{[3-(1,4,5,6-tetrahydro-2-pyrimidinylamino)benzoyl]amino}phenyl)sulfanyl]propanoic acid;
3-phenyl-3-[(3-{[3-(1,4,5,6-tetrahydro-2-pyrimidinylamino)benzoyl]amino}phenyl)sulfanyl]propanoic acid;
3-phenyl-3-[(4-{[3-(1,4,5,6-tetrahydro-2-pyrimidinylamino)benzoyl]amino}phenyl)sulfanyl]propanoic acid;
3-phenyl-3-[(2-{[4-(1,4,5,6-tetrahydro-2-pyrimidinylamino)benzoyl]amino}phenyl)sulfanyl]propanoic acid;
3-phenyl-3-[(3-{[4-(1,4,5,6-tetrahydro-2-pyrimidinylamino)benzoyl]amino}phenyl)sulfanyl]propanoic acid;
3-phenyl-3-[(4-{[4-(1,4,5,6-tetrahydro-2-pyrimidinylamino)benzoyl]amino}phenyl)sulfanyl]propanoic acid;
3-(3-pyridinyl)-3-[(2-{[3-(1,4,5,6-tetrahydro-2-pyrimidinylamino)benzoyl]amino}phenyl)sulfinyl]propanoic acid;
3-(3-pyridinyl)-3-[(3-{[3-(1,4,5,6-tetrahydro-2-pyrimidinylamino)benzoyl]amino}phenyl)sulfinyl]propanoic acid;
3-(3-pyridinyl)-3-[(4-{[3-(1,4,5,6-tetrahydro-2-pyrimidinylamino)benzoyl]amino}phenyl)sulfinyl]propanoic acid;
3-(3-pyridinyl)-3-[(2-{[4-(1,4,5,6-tetrahydro-2-pyrimidinylamino)benzoyl]amino}phenyl)sulfinyl]propanoic acid;
3-(3-pyridinyl)-3-[(3-{[4-(1,4,5,6-tetrahydro-2-pyrimidinylamino)benzoyl]amino}phenyl)sulfinyl]propanoic acid;
3-(3-pyridinyl)-3-[(4-{[4-(1,4,5,6-tetrahydro-2-pyrimidinylamino)benzoyl]amino}phenyl)sulfinyl]propanoic acid;
3-phenyl-3-[(2-{[3-(1,4,5,6-tetrahydro-2-pyrimidinylamino)benzoyl]amino}phenyl)sulfinyl]propanoic acid;
3-phenyl-3-[(3-{[3-(1,4,5,6-tetrahydro-2-pyrimidinylamino)benzoyl]amino}phenyl)sulfinyl]propanoic acid;
3-phenyl-3-[(4-{[3-(1,4,5,6-tetrahydro-2-pyrimidinylamino)benzoyl]amino}phenyl)sulfinyl]propanoic acid;
3-phenyl-3-[(2-{[4-(1,4,5,6-tetrahydro-2-pyrimidinylamino)benzoyl]amino}phenyl)sulfinyl]propanoic acid;
3-phenyl-3-[(3-{[4-(1,4,5,6-tetrahydro-2-pyrimidinylamino)benzoyl]amino}phenyl)sulfinyl]propanoic acid;
3-phenyl-3-[(4-{[4-(1,4,5,6-tetrahydro-2-pyrimidinylamino)benzoyl]amino}phenyl)sulfinyl]propanoic acid;
3-(3-pyridinyl)-3-[(2-{[3-(1,4,5,6-tetrahydro-2-pyrimidinylamino)benzoyl]amino}phenyl)sulfonyl]propanoic acid;
3-(3-pyridinyl)-3-[(3-{[3-(1,4,5,6-tetrahydro-2-pyrimidinylamino)benzoyl]amino}phenyl)sulfonyl]propanoic acid;
3-(3-pyridinyl)-3-[(4-{[3-(1,4,5,6-tetrahydro-2-pyrimidinylamino)benzoyl]amino}phenyl)sulfonyl]propanoic acid;

3-(3-pyridinyl)-3-[(2-{[4-(1,4,5,6-tetrahydro-2-pyrimidinylamino)benzoyl]amino}phenyl)sulfonyl]propanoic acid;
3-(3-pyridinyl)-3-[(3-{[4-(1,4,5,6-tetrahydro-2-pyrimidinylamino)benzoyl]amino}phenyl)sulfonyl]propanoic acid;
3-(3-pyridinyl)-3-[(4-{[4-(1,4,5,6-tetrahydro-2-pyrimidinylamino)benzoyl]amino}phenyl)sulfonyl]propanoic acid;
3-phenyl-3-[(2-{[3-(1,4,5,6-tetrahydro-2-pyrimidinylamino)benzoyl]amino}phenyl)sulfonyl]propanoic acid;
3-phenyl-3-[(3-{[3-(1,4,5,6-tetrahydro-2-pyrimidinylamino)benzoyl]amino}phenyl)sulfonyl]propanoic acid;
3-phenyl-3-[(4-{[3-(1,4,5,6-tetrahydro-2-pyrimidinylamino)benzoyl]amino}phenyl)sulfonyl]propanoic acid;
3-phenyl-3-[(2-{[4-(1,4,5,6-tetrahydro-2-pyrimidinylamino)benzoyl]amino}phenyl)sulfonyl]propanoic acid;
3-phenyl-3-[(3-{[4-(1,4,5,6-tetrahydro-2-pyrimidinylamino)benzoyl]amino}phenyl)sulfonyl]propanoic acid; and
3-phenyl-3-[(4-{[4-(1,4,5,6-tetrahydro-2-pyrimidinylamino)benzoyl]amino}phenyl)sulfonyl]propanoic acid;
either as a single isomer or as a mixture thereof, or a pharmaceutically acceptable salt thereof, in particular the hydrochloride or the trifluoroacetate.

What is claimed is:

1. A compound which is a non-peptide of the following formula (I)

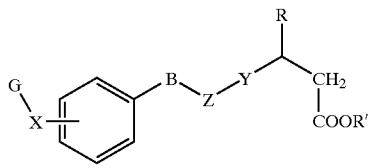

wherein:
G is

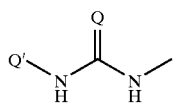

wherein Q is NH or O and Q' is H, $C_1$–$C_6$ alkyl, phenyl, or phenyl-$C_1$–$C_4$-alkyl;
X is a direct linkage, $CH_2$—CONH, —$(CH_2)_m$— or $(CH_2)_m$—X' wherein X' is O, S or NH and m is an integer of 1 to 4;
B is CONH, $CH_2$—CONH, a $C_2$–$C_4$ alkylene or $C_2$–$C_4$ alkenylene chain or —$(CH_2)_m$—X', wherein X' and m are as defined above;
A is a phenyl or pyridine ring, unsubstituted or substituted by one to three substituents chosen independently from halogen, $CF_3$, $C_1$–$C_4$ alkyl, OH and $C_1$–$C_4$ alkoxy;
Y is selected from O or $S(O)_n$ wherein n is zero, 1 or 2;
R is phenyl or $C_5$–$C_7$ monocyclic heteroaryl ring containing one to three heteroatoms chosen from O, S, and N, unsubstituted or substituted by one to three substituents chosen independently from halogen, $CF_3$, $C_1$–$C_4$ alkyl, hydroxy and $C_1$–$C_4$ alkoxy; and R' is hydrogen, $C_1$–$C_6$ alkyl, $C_2$–$C_4$ alkenyl, $C_2$–$C_4$ alkynyl, aryl or aryl-$C_1$–$C_4$ alkyl;
or a pharmaceutically acceptable salt thereof.

2. A compound according to claim 1, wherein
G is as defined above;
X is a direct linkage or $(CH_2)_m$—X', in which X' is as defined above;
B is CONH or CH=CH or $CH_2$—X', wherein X' is as defined above;
A is a phenyl ring unsubstituted or substituted, by one or two substituents selected from halogen, $CF_3$, $C_1$–$C_4$ alkyl, OH and $C_1$–$C_4$ alkoxy;
Y is as defined above;
R is a phenyl, pyridine, pyrazine, pyridazine, pyrimidine, thiophene, pyrrole, pyrazole, imidazole, oxazole or isoxazole ring, unsubstituted or substituted by one or two substituents selected from halogen, $CF_3$, $C_1$–$C_4$ alkyl, OH and $C_1$–$C_4$ alkoxy; and
R' is hydrogen, $C_1$–$C_6$ alkyl.

3. A compound according to claim 1, wherein
G and Y are as defined above;
X is $CH_2$—CONH or $(CH_2)_m$—X', in which m and X' are as defined above;
A is a phenyl or pyridine ring, unsubstituted or substituted by one to three substituents chosen independently from halogen, $CF_3$, $C_1$–$C_4$ alkyl, OH and $C_1$–$C_4$ alkoxy;
B is CONH or $CH_2$—CONH;
R is a phenyl, pyridine, pyrazine, pyridazine, pyrimidine, thiophene, pyrrole, pyrazole, imidazole, oxazole or isoxazole ring, unsubstituded or substituted by one or two substituents selected from halogen, $CF_3$, $C_1$–$C_4$ alkyl, OH and $C_1$–$C_4$ alkoxy; and
R' is hydrogen, $C_1$–$C_6$ alkyl.

4. A compound according to claim 1, wherein
G and Y are as defined above;
X is a direct linkage or $(CH_2)_m$—X', in which m is 1 or 2 and X' is as defined above;
B is CONH or CH=CH or $CH_2$—X', wherein X' is as defined above;
A is a phenyl ring unsubstituted or substituted by one or two substituents selected from halogen, $CF_3$, $C_1$–$C_4$ alkyl, OH and $C_1$–$C_4$ alkoxy;
R is a phenyl or pyridine ring, unsubstituded or substituted by one or two substituents selected from halogen, $CF_3$, $C_1$–$C_4$ alkyl, OH and $C_1$–$C_4$ alkoxy; and R' is hydrogen, $C_1$–$C_6$ alkyl.

5. A method for treating arthritis, comprising administering to a mammal in need thereof an effective αvβ3 inhibiting or antagonizing amount of a compound which is a nonpeptide of formula (I)

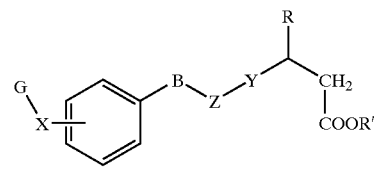

wherein:

G is

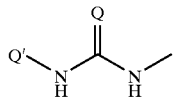

wherein Q is NH or O and Q' is H, $C_1$–$C_6$ alkyl, phenyl, or phenyl-$C_1$–$C_4$-alkyl;

X is a direct linkage, $CH_2$—CONH, —$(CH_2)_m$ or $(CH2)_m$X', wherein X' is O, S or NH and m is an integer of 1 to 4;

B is CONH, $CH_2$—CONH, a $C_2$–$C_4$ alkylene or $C_2$–$C_4$ alkenylene chain or —$(CH_2)_m$—X', wherein X' and m are as defined above;

A is a phenyl or pyridine ring, unsubstituted or substituted by one to three substituents chosen independently from halogen, $CF_3$, $C_1$–$C_4$ alkyl, OH and $C_1$–$C_4$ alkoxy;

Y is selected from O or $S(O)_n$ wherein n is zero, 1 or 2;

R is phenyl or $C_5$–$C_7$ monocyclic heteroaryl ring containing one to three heteroatoms chosen from O, S, and N, unsubstituted or substituted by one to three substituents chosen independently from halogen, $CF_3$, $C_1$–$C_4$ alkyl, hydroxy and $C_1$–$C_4$ alkoxy; and R' is hydrogen, $C_1$–$C_6$ alkyl, $C_2$–$C_4$ alkenyl, $C_2$–$C_4$ alkynyl, aryl or aryl-$C_1$–$C_4$ alkyl; or a phqrmaceutically acceptable salt thereof.

6. A product containing a compound which is a non-peptide of formula (I)

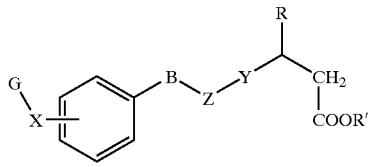

wherein:

G is

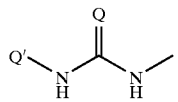

wherein Q is NH or o and Q' is H, $C_1$–$C_6$ alkyl, phenyl, or phenyl-$C_1$–$C_4$-alkyl;

X is a direct linkage, $CH_2$—CONH, $(CH_2)_m$— or $(CH_2)_m$—X', wherein X' is O, S or NH and m is an integer of 1 to 4;

B is CONH, $CH_2$—CONH, a $C_2$–$C_4$ alkylene or $C_2$–$C_4$ alkenylene chain or —$(CH_2)_m$—X', wherein X' and m are as defined above;

A is a phenyl or pyridine ring, unsubstituted or substituted by one to three substituents chosen independently from halogen, $CF_3$, $C_1$–$C_4$ alkyl, OH and $C_1$–$C_4$ alkoxy;

Y is selected from O or SO), wherein n is zero, 1 or 2;

R is phenyl or $C_5$–$C_7$ monocyclic heteroaryl ring containing one to three heteroatoms chosen from O, S, and N, unsubstituted or substituted by one to three substituents chosen independently from halogen, $CF_3$, $C_1$–$C_4$ alkyl, hydroxy and $C_1$–$C_4$ alkoxy;

R' is hydrogen, $C_1$–$C_6$ alkyl, $C_2$–$C_4$ alkenyl, $C_2$–$C_4$ alkynyl, aryl or aryl-$C_1$–$C_4$ alkyl;

or a pharmaceutically acceptable salt thereof, and an effective antineoplastic amount of additional antitumor agent as a combined preparation for simultaneous, separate or sequential use in anti-cancer therapy.

7. The product according to claim 6, wherein the additional antitumor agent is selected from an antineoplastic topoisomerase II inhibitor, an antineoplastic antimicrotubule agent, an antineoplastic alkylating agent, an antineoplastic antimetabolite and an antineoplastic topoisomerase I inhibitor.

\* \* \* \* \*